US012404221B2

(12) United States Patent
Gunnoe et al.

(10) Patent No.: US 12,404,221 B2
(45) Date of Patent: *Sep. 2, 2025

(54) METHODS OF ARENE ALKENYLATION

(71) Applicant: University of Virginia Patent Foundation, Charlottesville, VA (US)

(72) Inventors: Thomas Brent Gunnoe, Palmyra, VA (US); Xiaofan Jia, Hamden, CT (US); Lucas Isaac Frye, Monmouth Junction, NJ (US)

(73) Assignee: University of Virginia Patent Foundation, Charlottesville, VA (US)

( * ) Notice: Subject to any disclaimer, the term of this patent is extended or adjusted under 35 U.S.C. 154(b) by 278 days.

This patent is subject to a terminal disclaimer.

(21) Appl. No.: 17/999,273

(22) PCT Filed: May 19, 2021

(86) PCT No.: PCT/US2021/033149
§ 371 (c)(1),
(2) Date: Nov. 18, 2022

(87) PCT Pub. No.: WO2021/236764
PCT Pub. Date: Nov. 25, 2021

(65) Prior Publication Data
US 2023/0234900 A1    Jul. 27, 2023

Related U.S. Application Data

(60) Provisional application No. 63/027,132, filed on May 19, 2020.

(51) Int. Cl.
C07C 2/84 (2006.01)
B01J 31/22 (2006.01)
C07C 17/266 (2006.01)
C07C 41/30 (2006.01)
C07C 201/12 (2006.01)
C07C 253/30 (2006.01)
C07D 307/36 (2006.01)

(52) U.S. Cl.
CPC ............. C07C 2/84 (2013.01); B01J 31/2213 (2013.01); B01J 31/2291 (2013.01); C07C 17/266 (2013.01); C07C 41/30 (2013.01); C07C 201/12 (2013.01); C07C 253/30 (2013.01); C07D 307/36 (2013.01); *B01J 2231/4261* (2013.01); *B01J 2531/0208* (2013.01); *B01J 2531/822* (2013.01); *C07C 2523/46* (2013.01)

(58) Field of Classification Search
CPC ......... C07C 2/84; C07C 17/266; C07C 41/30; B01J 31/2213; B01J 2531/0208
See application file for complete search history.

(56) References Cited

U.S. PATENT DOCUMENTS 6,127,590 A * 10/2000 Taube .................... C07B 37/00
585/435
10,967,364 B2    4/2021 Gunnoe et al.

FOREIGN PATENT DOCUMENTS

WO    2018/183916 A1    10/2018

OTHER PUBLICATIONS

Chen et al. Catalytic Synthesis of Superlinear Alkenyl Arenes Using a Rh(I) Catalyst Supported by a "Capping Arene Ligand": Access to Aerobic Catalysis. Journal of the American Chemical Society, vol. 140, 17007-17018. (Year: 2018).*
International Search Report and Written Opinion, PCT/US2021/033149, mailed Sep. 8, 2021.
Jin, Weiwei, et al., "Efficient Rh(I)-Catalyzed Direct Arylation and Alkenylation of Arene C#H Bonds via Decarbonylation of Benzoic and Cinnamic Anhydrides," Organic Letters, vol. 11, No. 6 (2009), pp. 1317-1320.
Berman, Ashley M., et al., "Rh(I)-Catalyzed Direct Arylation of Pyridines and Quinolines," Journal of American Chemical Society, vol. 130 (2008), pp. 14926-14927.

* cited by examiner

Primary Examiner — Sikarl A Witherspoon
(74) Attorney, Agent, or Firm — THOMAS | HORSTEMEYER, LLP

(57) ABSTRACT

The present disclosure provides for a rhodium-catalyzed oxidative arene alkenylation from arenes and styrenes to prepare stilbene and stilbene derivatives. For example, the present disclosure provides for method of making arenes or substituted arenes, in particular stilbene and stilbene derivatives, from a reaction of an optionally substituted arene and/or optionally substituted styrene. The reaction includes a Rh catalyst or Rh pre-catalyst material and an oxidant, where the Rh catalyst or Rh catalyst formed Rh pre-catalyst material selectively functionalizes CH bond on the arene compound (e.g., benzene or substituted benzene).

24 Claims, 6 Drawing Sheets

A

*Path A - Prefunctionalized substates*

$X = Cl, Br, I, N_2^+, SO_2R$

*Path B - Directed C–H activation*

DG = Directing group

B

This Work

C

Proposed Mechanism

Scheme 1

Scheme 2

Scheme 3

METHODS OF ARENE ALKENYLATION

CROSS-REFERENCE TO RELATED APPLICATION

This application claims priority to U.S. provisional application entitled "Synthesis of pharmaceutical intermediates by Rh and Pd catalyzed arene alkenylation" having Ser. No. 63/027,132 filed on May 19, 2021 which is entirely incorporated herein by reference.

FEDERAL SPONSORSHIP

This invention was made with government support under Grant No. DE-SC0000776, awarded by U.S. Department of Energy. The government has certain rights in the invention.

BACKGROUND

Stilbene and stilbene derivatives are of interest in organic chemistry since stilbene derivatives are potentially applicable in the pharmaceutical industry and in various other materials and products. Many stilbene derivatives exhibit photophysical and photochemical properties that are useful, while other products of are of medicinal interest.

SUMMARY

Embodiments of the present disclosure provide for a rhodium-catalyzed oxidative arene alkenylation from arenes and styrenes to prepare stilbene and stilbene derivatives.

An exemplary embodiment of the present disclosure provides for a method of making a substituted arene, comprising:

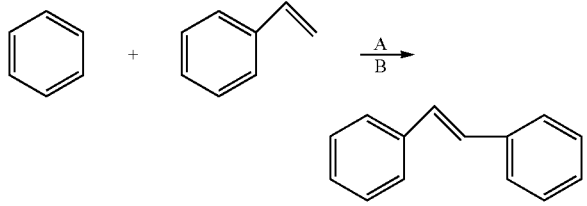

wherein A is a Rh catalyst or Rh pre-catalyst material (which can form a Rh catalyst), wherein the Rh catalyst selectively functionalizes CH bond on the arene compound, wherein B is an oxidant.

In another embodiment, the present disclosure provides for a method of making a substituted arene, comprising:

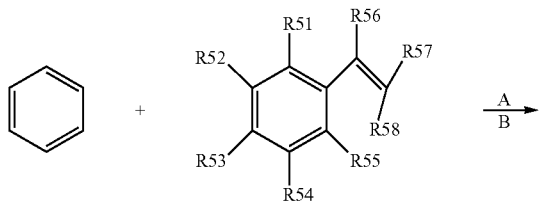

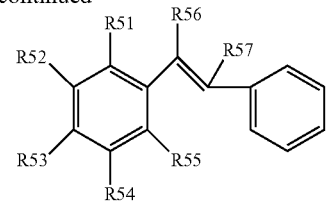

wherein A is a Rh catalyst or Rh pre-catalyst material (which can form a Rh catalyst), wherein the Rh catalyst selectively functionalizes CH bond on the benzene compound, wherein B is an oxidant, wherein R51 to R58 are each independently selected from the group consisting of: hydrogen, a halide, an alkyl, an alkenyl, a —O—R', a carbocycle group, a heterocyclo, an aryl, a heteroaryl, —NO$_2$, —C(O)OR', —CN, SiR'$_3$, and —OR', wherein each R' is independently selected from H and an alkyl.

In an embodiment, the present disclosure provides for a method of making a substituted arene, comprising:

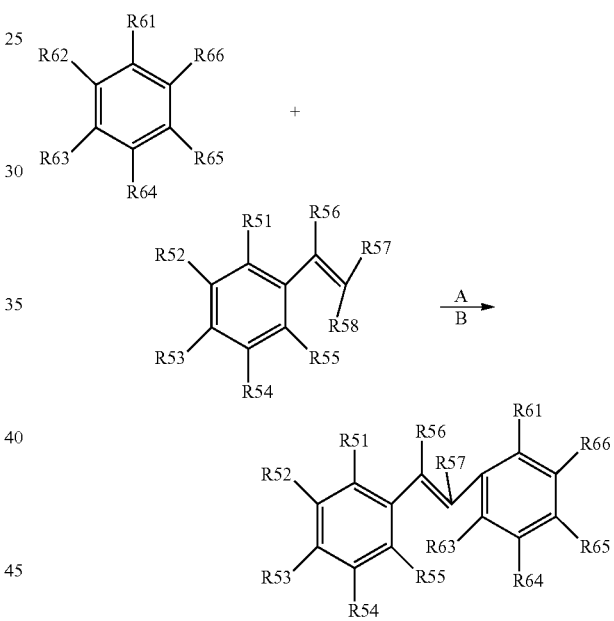

wherein A is a Rh catalyst or Rh pre-catalyst material (which can form a Rh catalyst), wherein the Rh catalyst selectively functionalizes a CH bond in meta and para positions of the substituted benezene relative to the functional group, wherein B is an oxidant, wherein R51 to R58 are each independently selected from the group consisting of: hydrogen, a halide, an alkyl, an alkenyl, a —O—R', a carbocycle group, a heterocyclo, an aryl, a heteroaryl, —NO$_2$, —C(O)OR', —CN, SiR'$_3$, and —OR', wherein each R' is independently selected from H and an alkyl, wherein R61 to R66 are each independently selected from the group consisting of: hydrogen, a halide, an alkyl, an alkenyl, a —O—R", a carbocycle group, a heterocyclo, an aryl, a heteroaryl, —NO$_2$, —C(O)OR", —CN, SiR"$_3$ and —OR", wherein each R" is independently selected from H and an alkyl.

In regard to each of the reactions above, the oxidant is selected from the group consisting of a copper(II) salt, iodates, periodates, nitrogen oxide, silver salt, peroxide, dioxygen, copper(I) salt and one or both of dioxygen and air, and a combination thereof. In an aspect, the Rh catalyst or Rh pre-catalyst material (which can form a Rh catalyst) is a composition comprising: a rhodium (I) catalyst having one of the following formula: $L_2Rh(L')X$, $L_3RhX$, $(L_1X_1)Rh(L')$, $[(L)_2Rh(\mu\text{-}X)]_2$, $RhX_3$, $[L_nRh_y(\mu\text{-}X)_m]$, or $(L)_nRh_m$ (or precursor thereof) wherein $L_2$ is selected from: two independent and neutral first ligands each coordinated to Rh(I) through a carbon donor, nitrogen donor, a phosphorus donor, an oxygen donor, or a sulfur donor, a neutral bidentate ligand coordinated to Rh(I) through either a carbon donor, nitrogen donor, a phosphorus donor, an oxygen donor, or a sulfur donor, or a combination of the neutral first ligand and the neutral bidentate ligand; wherein L' is a neutral second ligand coordinated to Rh(I), wherein X is a mono-anionic group, either coordinated to the metal or not, wherein $L_3$ is a tridentate first ligand coordinated to Rh(I) in a $\kappa^2$ or $\kappa^3$ fashion through a carbon donor, a nitrogen donor, a phosphorus donor, an oxygen donor, a sulfur donor, or a combination thereof, wherein $L_1X_1$ is a monoanionic bidentate or tridentate second ligand coordinated to Rh(I) in a $\kappa^2$ or $\kappa^3$ fashion through a carbon donor, a nitrogen donor, a phosphorus donor, an oxygen donor, a sulfur donor, or a combination thereof, wherein L is a neutral, two-electron donating third ligand coordinated to Rh(I), and wherein y is 1 to 4, m is 1 to 4 and n is 3(m). In an aspect, the ratio of the benzene to styrene is about 1:100 to 1000:1, wherein the amount of Rh catalyst is about 20 mol % to 0.000000001 mol %, wherein the amount of oxidant is about 2 to 10,000 equivalents relative to Rh catalyst. In an aspect, the reaction temperature is about 125-205° C. for about 1 to 72 hours.

BRIEF DESCRIPTION OF THE DRAWINGS

Further aspects of the present disclosure will be more readily appreciated upon review of the detailed description of its various embodiments, described below, when taken in conjunction with the accompanying drawings.

FIG. 1A illustrates current synthetic strategies for the preparation of stilbene and stilbene derivatives. For instances where an "R" group (in any of the Figures, Tables or schematics or elsewhere in the application) is shown as bonded to the middle of a ring (e.g., of an arene), such as shown in FIG. 1A, then the R group can be bonded to any C on the ring that would otherwise be bonded to H or multiple R groups can be bonded to different C on the ring that would otherwise be bonded to H. FIG. 1B illustrates aerobic arene alkenylation catalyzed by Rh via a C—H activation pathway. FIG. 1C illustrates a proposed catalytic cycle for late transition metal-catalyzed oxidative arene alkenylation, in which Cu(II) is used as the in situ oxidant, to produce stilbene and stilbene derivatives.

FIG. 2A illustrates the synthesis of resveratrol and DMU-212. Yields are isolated. Conditions: (i): 0.25 mol % $[Rh(\mu\text{-}OAc)(\eta^2\text{—}C_2H_4)_2]_2$ (1) (0.5 mol % based on rhodium), 160 equiv. copper(II) pivalate, 800 equiv. pivalic acid, 60 psig $N_2$, 15 psig air, 5 mL arene as solvent, 500 μmol of 4-vinylanisole, 135° C., 96 hours, reactors were open to air every 24 hours; (ii) $BBr_3$, 0-30° C., quant, overnight.

FIG. 3A illustrates the regioselectivity differences [a]$[Rh]=0.5$ $[Rh(\mu\text{-}OAc)(\eta^2\text{—}C_2H_4)_2]_2$ (1) and $[Pd]=Pd(OAc)_2$ (4). [b]Amounts of Cu(II) pivalate and pivalic acid are relative to [M]. [c]Reaction temperature=135° C. FIG. 3B illustrates bioactive molecule synthesis that benefit from the selectivity differences between Rh and Pd. FIG. 3C illustrates the differences between Pd and Rh catalysis for C—X vs. C—H bond activation (X=Cl, Br, I).

DETAILED DESCRIPTION

Figure 1:
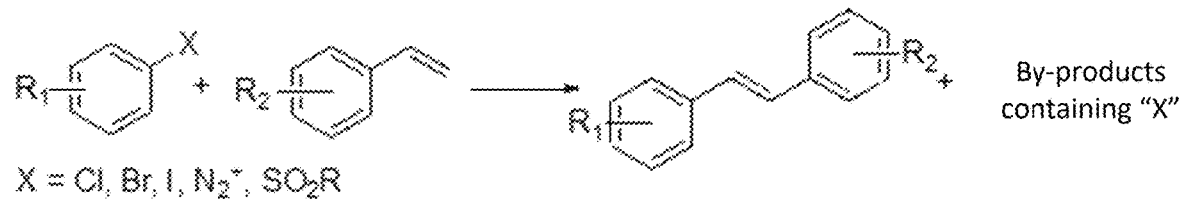
FIGS. 1A-C illustrate stilbene synthesis via transition-metal catalyzed arene alkenylation between arenes and vinylarenes.
Figure 1:
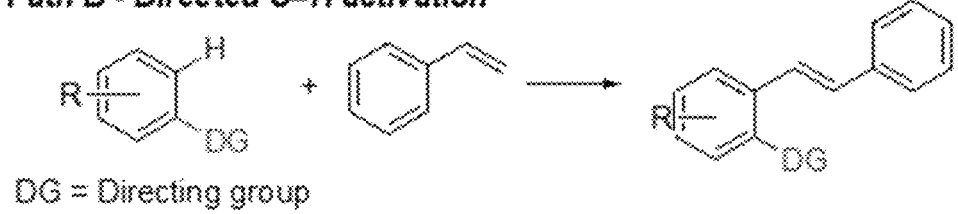
Figure 1:
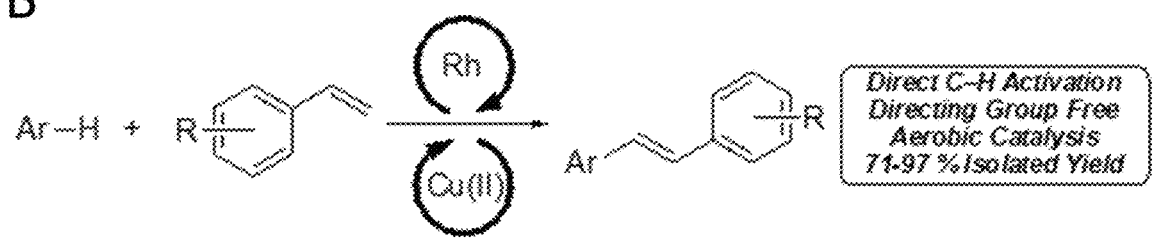
Figure 1:
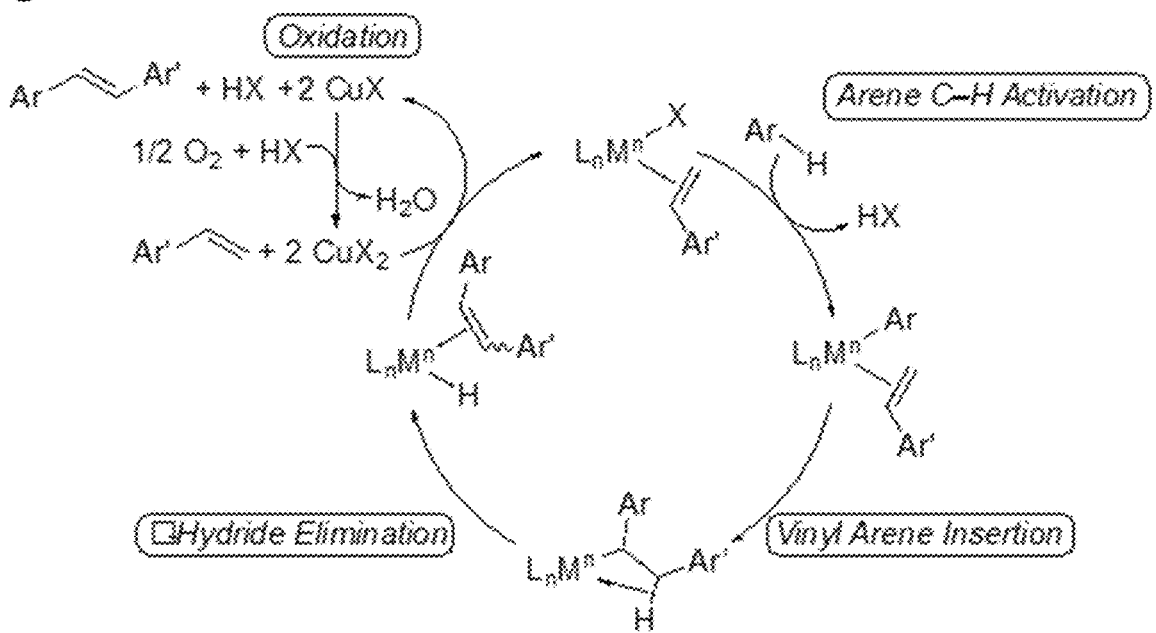

Before the present disclosure is described in greater detail, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit (unless the context clearly dictates otherwise), between the upper and lower limit of that range, and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of chemistry, inorganic chemistry, synthetic chemistry, and the like, which are within the skill of the art. Such techniques are explained fully in the literature.

The following description and examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is in bar or psig. Standard temperature and pressure are defined as 25° C. and 1 bar.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible. Different stereochemistry is also possible, such as products of cis or trans orientation around a carbon-carbon double bond or syn or anti addition could be both possible even if only one is drawn in an embodiment.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

Definitions

By "chemically feasible" is meant a bonding arrangement or a compound where the generally understood rules of organic structure are not violated. The structures disclosed herein, in all of their embodiments are intended to include only "chemically feasible" structures, and any recited structures that are not chemically feasible, for example in a structure shown with variable atoms or groups, are not intended to be disclosed or claimed herein. However, if a bond appears to be intended and needs the removal of a group such as a hydrogen from a carbon, the one of skill would understand that a hydrogen could be removed to form the desired bond.

The term "substituted" refers to any one or more hydrogen atoms on the designated atom (e.g., a carbon atom) that can be replaced with a selection from the indicated group (e.g., halide, hydroxyl, alkyl, and the like), provided that the designated atom's normal valence is not exceeded. As used herein, the term "optionally substituted" typically refers to from zero to four substituents, wherein the substituents are each independently selected. Each of the independently selected substituents may be the same or different than other substituents. For example, the substituents (e.g., an R type group) of a formula may be optionally substituted (e.g., from 1 to 4 times) with independently selected H, halogen, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid, etc. In an embodiment, substituted includes substitution with a halogen.

As used herein, a "derivative" of a compound refers to a chemical compound that may be produced from another compound of similar structure in one or more steps, as in replacement of H by an alkyl, acyl, amino group, etc.

As used herein, "aliphatic" or "aliphatic group" refers to a saturated or unsaturated, linear or branched, cyclic (non-aromatic) or heterocyclic (non-aromatic), hydrocarbon or hydrocarbon group, where each can be substituted or unsubstituted, and encompasses alkyl, alkenyl, and alkynyl groups, and alkanes, alkene, and alkynes, for example, substituted or unsubstituted.

As used herein, "alkane" refers to a saturated aliphatic hydrocarbon which can be straight or branched, having 1 to 40, 1 to 20, 1 to 10, or 1 to 5 carbon atoms, where the stated range of carbon atoms includes each intervening integer individually, as well as sub-ranges. Examples of alkane include, but are not limited to methane, ethane, propane, butane, pentane, and the like. Reference to "alkane" includes unsubstituted and substituted forms of the hydrocarbon moiety.

As used herein, "alkyl" or "alkyl group" refers to a saturated aliphatic hydrocarbon, which can be straight or branched, having 1 to 40, 1 to 20, 1 to 10, or 1 to 5 carbon atoms, where the stated range of carbon atoms includes each intervening integer individually, as well as sub-ranges. Examples of alkyl groups include, but are not limited to methyl, ethyl, n-propyl, i-propyl, n-butyl, s-butyl, t-butyl, n-pentyl, and s-pentyl. Reference to "alkyl" or "alkyl group" includes unsubstituted and substituted forms of the hydrocarbon moiety.

As used herein, "alkene" (also referred to as an "olefin") refers to an aliphatic hydrocarbon which can be straight or branched, containing at least one carbon-carbon double bond, having 2 to 40, 2 to 20, 2 to 10, or 2 to 5 carbon atoms, where the stated range of carbon atoms includes each intervening integer individually, as well as sub-ranges. Examples of alkene groups include, but are not limited to, ethylene, propylene, 1-pentene, 1-hexene, isobutene and the like. Reference to "alkene" includes unsubstituted and substituted forms of the hydrocarbon moiety.

As used herein, "alkenyl" or "alkenyl group" refers to an aliphatic hydrocarbon, which can be straight or branched, containing at least one carbon-carbon double bond, having 2 to 40, 2 to 20, 2 to 10, or 2 to 5 carbon atoms, where the stated range of carbon atoms includes each intervening integer individually, as well as sub-ranges. Examples of alkenyl groups include, but are not limited to, ethenyl, propenyl, n-butenyl, i-butenyl, 3-methylbut-2-enyl, n-pentenyl, heptenyl, octenyl, decenyl, and the like. Reference to "alkyl" or "alkyl group" includes unsubstituted and substituted forms of the hydrocarbon moiety.

As used herein, "alkyne" refers to straight or branched chain hydrocarbon groups having 2 to 40, 2 to 20, 2 to 10, or 2 to 5 carbon atoms and at least one triple carbon to carbon bond. Reference to "alkyne" includes unsubstituted and substituted forms of the hydrocarbon moiety.

As used herein, "alkynyl" or "alkynyl group" refers to straight or branched chain hydrocarbon groups having 2 to 40, 2 to 20, 2 to 10, or 2 to 5 carbon atoms and at least one triple carbon to carbon bond, such as ethynyl. Reference to "alkynyl" or "alkynyl group" includes unsubstituted and substituted forms of the hydrocarbon moiety.

The term "carbocycles" refers to a monocyclic or multicyclic ring system of about 5 to about 40 or about 5 to 34 carbon atoms, preferably of about 6 to about 10 carbon atoms, where the carbocycle can be saturated or unsaturated. In an embodiment, the carbocycle can be aromatic or non-aromatic. In an embodiment, carbocycle can refer to an aryl group. Exemplary carbocycles can refer to functional groups such as phenyl and naphthyl. Reference to carbocycles includes substituted or unsubstituted carbocycles.

As used herein, "aromatic" refers to a monocyclic or multicyclic ring system of 5 to 20 or 5 to 10 carbon atoms having alternating double and single bonds between carbon atoms. Exemplary aromatic groups include benzene, naphthalene, alkyl arene, cyclopentadienyl and the like. Reference to "aromatic" includes unsubstituted and substituted forms of the hydrocarbon moiety.

As used herein, "aryl" or "aryl group" refers to an aromatic monocyclic or multicyclic ring system of 5 to 20 or 5 to 10 carbon atoms. The aryl is optionally substituted with one or more $C_1$-$C_{20}$ alkyl, alkylene, alkoxy, or haloalkyl groups. Exemplary aryl groups include phenyl or naphthyl, or substituted phenyl or substituted naphthyl. Reference to "aryl" or "aryl group" includes unsubstituted and substituted forms of the hydrocarbon moiety.

As used herein, "halo", "halogen", "halide", or "halogen radical" refers to a fluorine, chlorine, bromine, iodine, and astatine, and radicals thereof. Further, when used in compound words, such as "haloalkyl" or "haloalkenyl", "halo" refers to an alkyl or alkenyl radical in which one or more hydrogens are substituted by halogen radicals. Examples of haloalkyl include, but are not limited to, trifluoromethyl, trichloromethyl, pentafluoroethyl, and pentachloroethyl.

As used herein, "cyclic" hydrocarbon refers to any stable 4, 5, 6, 7, 8, 9, 10, 11, or 12 membered, (unless the number of members is otherwise recited), monocyclic, bicyclic, or tricyclic cyclic ring.

As used herein, "heterocycle" refers to any stable 4, 5, 6, 7, 8, 9, 10, 11, or 12 membered, (unless the number of members is otherwise recited), monocyclic, bicyclic, or tricyclic heterocyclic, and the like ring that is saturated or partially unsaturated, and which includes carbon atoms and 1, 2, 3, 4 or more heteroatoms independently selected from the group consisting of N, P, O, and S. If the heterocycle is defined by the number of carbons atoms, then from 1, 2, 3, 4 or more of the listed carbon atoms are replaced by a heteroatom. If the heterocycle is bicyclic or tricyclic, then at least one of the two or three rings must contain a heteroatom, though both or all three may each contain one or more heteroatoms. The N group may be N, NH, or N-substituent, depending on the chosen ring and if substituents are recited. The P group may be P, PH, or P-substituent, depending on the chosen ring and if substituents are recited. The nitrogen and sulfur heteroatoms optionally may be oxidized (e.g., S, S(O), $S(O)_2$, and N—O). The heterocycle may be attached to its pendant group at any heteroatom or carbon atom that results in a stable structure. The heterocycles described herein may be substituted on carbon or on a heteroatom if the resulting compound is stable. In an embodiment, the heterocycle can include furan, pyrrole, thiophene, benzofuran, indole, benzothiophene, pyridine, quinoline, isoquinoline, oxazole, benzoxazole, isoxazole, triazole, pyrroline, pyrrolidine, imidazole, imidazoline, pyrazole, pyran, piperidine, dioxane, morpholine, pyrimidine, pyridazine, pyrazine, indolizidine, isoindole, indoline, benzimidazole, carbazole, thiazole, each of which can be substituted or unsubstituted.

"Heteroaryl" refers to any stable 5, 6, 7, 8, 9, 10, 11, or 12 membered, (unless the number of members is otherwise recited), monocyclic, bicyclic, or tricyclic heterocyclic ring that is aromatic, and which consists of carbon atoms and 1, 2, 3, 4 or more heteroatoms independently selected from the group consisting of N, O, and S. If the heteroaryl is defined by the number of carbons atoms, then 1, 2, 3, 4 or more of the listed carbon atoms are replaced by a heteroatom. If the heteroaryl group is bicyclic or tricyclic, then at least one of the two or three rings must contain a heteroatom, though both or all three may each contain one or more heteroatoms. If the heteroaryl group is bicyclic or tricyclic, then only one of the rings must be aromatic. The N group may be N, NH, or N-substituent, depending on the chosen ring and if substituents are recited. The nitrogen and sulfur heteroatoms may optionally be oxidized (e.g., S, S(O), $S(O)_2$, and N—O). The heteroaryl ring may be attached to its pendant group at any heteroatom or carbon atom that results in a stable structure. The heteroaryl rings described herein may be substituted on carbon or on a nitrogen atom if the resulting compound is stable. In an embodiment, the heteroaryl ring can include furanyl, pyranyl, thienyl, imidazyl, pyrrolyl, pyridyl, pyrazolyl, pyrazinyl, pyrimidinyl, indolyl, quinolyl, isoquinolyl, quinoxalyl, and quinazolinyl. Preferred examples are furanyl, imidazyl, pyranyl, pyrrolyl, and pyridyl.

The term "heteroatom" means for example oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring).

The term "bicyclic" represents either an unsaturated or saturated stable 7- to 18-membered bridged or fused bicyclic carbon ring. The bicyclic ring may be attached at any atom which affords a stable structure. The term includes, but is not limited to, naphthyl, dicyclohexyl, dicyclohexenyl, and the like.

The term "cyano" refers to a —CN moiety.

The term "nitrile" refers to R'—CN, where R' is selected from an alkyl, an alkenyl, a carbocycle group, a heterocyclo, an aryl, or a heteroaryl.

The term "imine" refers to R'1-N=CR"R'", where R', R", and R'" are each independently selected from an alkyl, an alkenyl, a carbocycle group, a heterocyclo, an aryl, or a heteroaryl.

The term "ether" refers to R'OR", where R' and R" are each independently selected from an alkyl, an alkenyl, a carbocycle group, a heterocyclo, an aryl, or a heteroaryl.

The term "ketone" refers to O=CR'R", where R' and R" are each independently selected from an alkyl, an alkenyl, a carbocycle group, a heterocyclo, an aryl, or a heteroaryl.

The term "phosphine" refers to $PH_3$, or trisubstituted phosphorus atoms such as triphenylphosphine.

The term "sulfur based ligand" refers to R'SR" or R'S or other combinations in which sulfur is incorporated into a ligand, either bound to the metal or not.

The term "silyl" refers to —$SiR'_3$ or —$SiR''_3$ where R' or R" are each independently selected from an alkyl, an alkenyl, a carbocycle group, a heterocyclo, an aryl, or a heteroaryl.

As used herein, the term "purified" and like terms relate to an enrichment of a molecule or compound relative to other components normally associated with the molecule or compound in a native environment. The term "purified" does not necessarily indicate that complete purity of the particular molecule has been achieved during the process. A "highly purified" compound as used herein refers to a compound that is greater than 90% pure.

General Discussion

Arene alkenylation is commonly achieved by late transition metal-mediated $C(sp^2)$-$C(sp^2)$ cross-coupling, but this strategy typically requires pre-functionalized substrates (e.g., with halides or pseudo-halides) and/or the presence of a directing group on the arene. Transition metal-mediated arene C—H activation and alkenylation that does not require a directing group, but that can tolerate directing groups, offers an alternative method to functionalize arene substrates.

The present disclosure provides for a rhodium-catalyzed oxidative arene alkenylation from arenes and styrenes to prepare stilbene and stilbene derivatives. In aspects, the reaction can be performed using a variety of functional groups on both the arene and the olefin. Example 1 provides illustrations of the versatility of the present disclosure. In one aspect, reactions of mono-substituted arenes are selective for alkenylation at the meta and para positions, generally with approximately 2:1 selectivity, respectively. In this regard, Resveratrol and (E)-1,2,3-trimethoxy-5-(4-methoxystyryl)benzene (DMU-212) can be synthesized by this single-step approach in high yield. In addition, example 1 shows that in a comparison with palladium catalysis, rhodium catalysis is more selective for meta-functionalization for mono-substituted arenes, and that the Rh catalysis has better tolerance of halogen groups. Additional details are provided in Example 1.

The present disclosure provides for method of making arenes or substituted arenes, in particular stilbene and stilbene derivatives, from a reaction of an optionally substituted arene and/or optionally substituted styrene. The reaction includes a Rh catalyst or Rh pre-catalyst material (which can form the Rh catalyst during the reaction) and an oxidant, where the Rh catalyst or Rh catalyst formed Rh pre-catalyst material selectively functionalizes CH bond on the arene compound (e.g., benzene or substituted benzene). In one aspect, the method of making a substituted arene can be shown in the following reaction scheme:

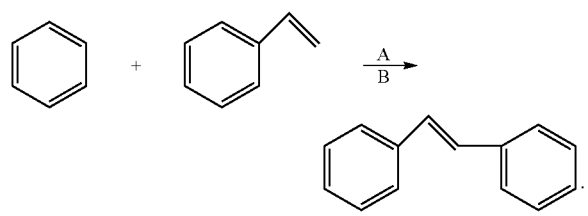

A is a Rh catalyst or Rh pre-catalyst material and where B is an oxidant.

In another aspect, the method of making a substituted arene can be shown in the following reaction scheme:

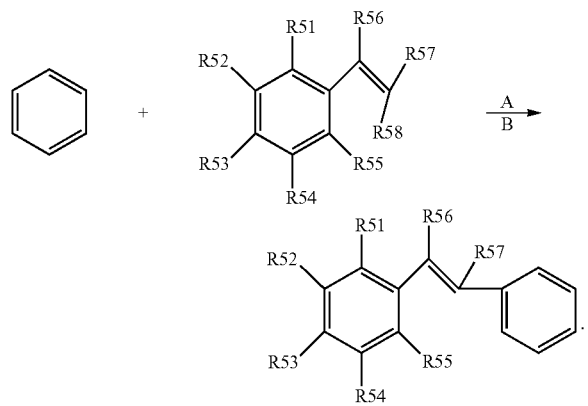

A is a Rh catalyst or Rh pre-catalyst material and where B is an oxidant. R51 to R58 can each be independently selected from the group consisting of: hydrogen, a halide, an alkyl, an alkenyl, a —O—R', a carbocycle group, a heterocyclo, an aryl, a heteroaryl, —NO$_2$, —C(O)OR', —CN, SiR'$_3$, and —OR'. Each R' is independently selected from H and an alkyl. In an aspect, R56-R58 can be selected from the group consisting of: H and an alkyl.

In another aspect, the method of making a substituted arene can be shown in the following reaction scheme:

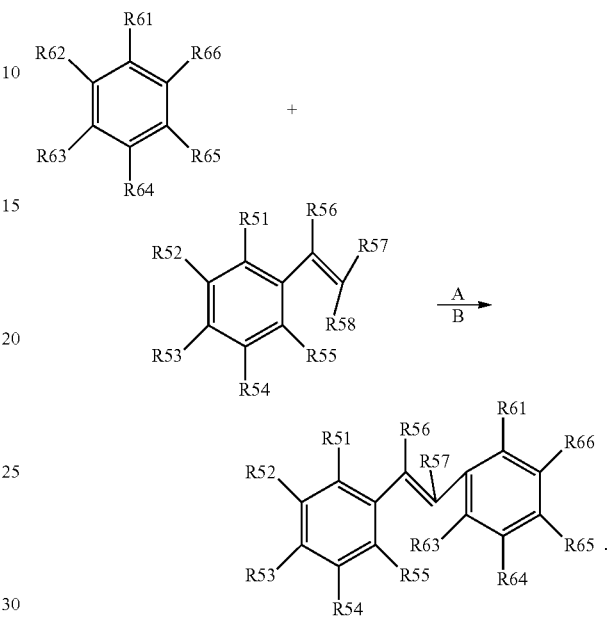

A is a Rh catalyst or Rh pre-catalyst material and where B is an oxidant.

The Rh catalyst (or the Rh catalysts from the Rh pre-catalyst material) can selectively functionalize a CH bond in meta and para positions of the substituted benzene relative to the functional group. The selectivity for meta and para (combined) is generally >90% and often quantitative, with the meta/para ratio generally and approximately 2:1. R51 to R58 can each be independently selected from the group consisting of: hydrogen, a halide, an alkyl, an alkenyl, a —O—R', a carbocycle group, a heterocyclo, an aryl, a heteroaryl, —NO$_2$, —C(O)OR', —CN, SiR'$_3$, and —OR'. Each R' is independently selected from H and an alkyl. In an aspect, R56-R58 can be selected from the group consisting of: H and an alkyl. R61 to R66 can each be independently selected from the group consisting of: hydrogen, a halide, an alkyl, an alkenyl, a —O—R", a carbocycle group, a heterocyclo, an aryl, a heteroaryl, —NO$_2$, —C(O)OR", —CN, SiR"$_3$ and —OR", wherein each R" is independently selected from H and an alkyl, where at least one group R61-R66 is a H atom.

Each of the reactions can be conducted in a single container (e.g., "one pot synthesis"). In an embodiment, each of the reactions can be conducted at a temperature of about 100-250° C. or 135-165° C., while the reaction time for each can be about 5 mins to 5 days, about 12 to 36 hours, or about 24 hours. In an embodiment, the ratio of the optionally substituted arene to optionally substituted styrene can be about 1:100 to 1000:1 or about 1:100 to 100:1. In an embodiment the amount of catalyst can be about 20 mol % to 0.000000001 mol % or 10 mol % to 0.000000001 mol %. In an embodiment, the amount of oxidant can be about 2 to 100,000 equivalents, about 2 to 10,000 equivalents, or about 2 to 1000 equivalents relative to catalyst.

In addition to the Rh catalyst or Rh pre-catalyst material and the oxidant, the following materials can be included in the reaction: solvent (e.g., carboxylic acid, pentane, cyclohexane, hexanes, dioxanes, tetrahydrofuran, etc.), air (e.g., at ambient to 5000 psi), $N_2$ (e.g., at ambient to 5000 psi), and carboxylic acid.

In an embodiment, the products (e.g., arenes or substituted arenes such as stilbene and stilbene derivatives) can be produced with about 50, 60, 70, 80, 90, 91, 92, 93, 94, 95, 96, 97, 98, or 99, each up to 100% selectivity (e.g., about 50 to 100%). In particular, the Rh catalyst can selectively functionalize a CH bond in meta and para positions relative to the ortho position for the substituted benzene relative to the functional group(s) when present. In an embodiment, the yield is high relative to oxidant. In one aspect the yield is about 50, 60, 70, 80, or 90, each up to 100% (e.g., about 50 to 100%, about 70 to 100%, or about 80 to 100%). In an embodiment, the product can be produced with high selectivity (e.g., about 70% to 100%) and with a high yield relative to oxidant (e.g., about 50% to 100%).

In an embodiment, the oxidant can be represented as $A_aX_n$. In an embodiment, "A" can represent an element or combination of elements capable of maintaining a formal positive charge. In an embodiment $A_aX_n$, can be a salt such as a halide salt (e.g., $CuCl_2$). In an embodiment, "A" can be: a transition metal or redox-active main-group metal. In an embodiment, X can be a halide such as chloride, bromide, iodide, an acetate, a trifluoroacetate, a pivalate, and the like. In an embodiment, subscript "a" can represent the oxidation state of "X" and subscript "n" can represent the oxidation state of "A". In an embodiment $A_aX_n$, can be: $CuCl_2$, $CuBr_2$, $Cu(OAc)_2$, $FeCl_3$, $Fe(OAc)_3$, $AgCl$, $MnCl_2$, $IO_3^-$, $IO_4^-$, $NO_2$, $MnCl_3$, etc. In an embodiment, the oxidant can be recyclable using air or purified oxygen. In an embodiment, the air-recyclable oxidant can include a copper(II) salt (e.g., $CuX_2$), iodates, periodates, nitrogen dioxide, silver salts, peroxide, dioxgen, iron(III) salts, and the like as well as copper(I) salts and one or both of dioxygen and air. These compounds are available for purchase from commercial suppliers, can be prepared from reported procedures, can be prepared in situ by reaction of elements with halogen sources and from natural saline solutions.

In an embodiment, the Rh(I) catalyst (as well as the Rh catalyst formed from the Rh per-catalyst material) can have one of the following formula: $L_2Rh(L')X$, $L_3RhX$, $(L_1X_1)Rh(L')$, $[(L)_2Rh(\mu-X)]_2$, $RhX_3$, $[L_nRh_y(\mu-X)_m]$, or $(L)_nRh_m$, (or precursor materials thereof in regard to the Rh re-catalyst material).

In an embodiment, $L_2$ can be selected from: a) two independent and neutral first ligands coordinated to Rh(I) through a carbon donor, a nitrogen donor, a phosphorus donor, an oxygen donor, a sulfur donor, or combination of these donors, b) a neutral bidentate ligand coordinated to Rh(I) through a nitrogen donor, a phosphorus donor, an oxygen donor, a sulfur donor, or combination of these donors, or c) a combination of the neutral ligand and the neutral bidentate ligand.

In an embodiment, when $L_2$ is selected from two independent and neutral ligands coordinated to the Rh(I), the neutral ligands can include: an amine (e.g., ammonia, aniline, triethylamine) a pyridine (e.g., pyridine or a substituted pyridine such as 4-methylpyridine), a phosphine (e.g., trimethylphosphine, triphenylphosphine), a phosphite (e.g., trimethylphosphite or triphenylphosphite), other phosphine-based ligands (e.g., phospholes, cyclic phosphites, N-heterocyclic phospheniums, phosphine oxides), an ether (e.g., diethyl ether, diphenyl ether, methyl ethyl ether), a ketone or aldehyde (e.g., acetone, benzaldehyde), and an imine.

In an embodiment, when the $L_2$ is the neutral bidentate ligand coordinated to the Rh(I), the neutral bidentate ligand can include: a bipyridine (e.g., 2,2'-bipyridyl), a diamine (e.g. 1,2-diaminopropane, phenylenediamine), a bipyrimidine (e.g. 2,2'-bipyrimidine, 5,5'-bipyrimidine), a bisoxazoline (e.g. BOX, PyBOX), a diphosphine (e.g. 1,2-bis(dimethylphosphino)ethane, 1,2-bis(diphenylphosphino)ethane), a phosphinamine (e.g. DavePhos), a phoshinimine (e.g., (2-phosphanylphenyl)methanimine), an imidate (e.g. ethyl benzimidate, N-Methylbenzamide), a bispyrazole (e.g. 1,1'-bipyrazole, bispyrazoleborate), and a bisimidazole (e.g. 2,2'-bis(4,5-dimethylimidazole), 1,2-bis(imidazole-1-yl)ethane).

In an embodiment, L' can be a neutral second ligand coordinated to Rh(I). In an embodiment, the neutral second ligand can include: an olefin (e.g., ethene, propylene), an imine (e.g. N,1,1-triphenylmethanimine), an ether (e.g., diethyl ether, diphenyl ether, methyl ethyl ether), a nitrile (e.g., acetonitrile, benzonitrile), a ketone or aldehyde (e.g., acetone, benzaldehyde), water, a sulfur based ligand (e.g., dimethylsulfide), and a phosphine (e.g., trimethylphosphine, triphenylphosphine).

In an embodiment, X can be a mono-anionic group, either coordinated to the metal or not. In an embodiment, the mono-anionic group can be: a halide, an alkyl, an alkenyl, a carbocycle group, a heterocyclo, an aryl, a heteroaryl, and an acetate.

In an embodiment, $L_3$ can be a tridentate first ligand coordinated to Rh(I) in a $\kappa^2$ or $\kappa^3$ fashion through a carbon donor, a nitrogen donor, a phosphorus donor, an oxygen donor, a sulfur donor, or a combination thereof. In an embodiment, the tridentate first ligand can be: a terpyridine, a pyridyl diimine, a triphosphine, a diphosphine imine, a bis(phosphino)pyridine, a tris(pyrazolyl)alkane, a tris(ethylenediamine), a trithiolate, a trithiolene, a bis(imino)furan, and the like.

In an embodiment, $L_1X_1$ can be a monoanionic bidentate or tridentate second ligand coordinated to Rh(I) in a $\kappa^2$ or $\kappa^3$ fashion through a carbon donor, a nitrogen donor, a phosphorus donor, an oxygen donor, a sulfur donor, or a combination thereof. In an embodiment, the monoanionic bidentate or tridentate second ligand, can be: diphosphino aryl, imidates, diketiminates, trispyrazolylborate, trisimidazoles, pyridine aryl imidazoles, tris(pyrazolyl)borates, and the like.

In an embodiment, L can be a neutral, two-electron donating third ligand coordinated to Rh(I). In an embodiment, the neutral third ligand is selected from the group consisting of: an olefin, an imine, an ether, a nitrile, a ketone, water, a sulfur based ligand, a phosphine, a phosphine-based ligand, an N-heterocyclic carbene.

In an embodiment, y can be 1 to 4, m can be 1 to 4 and n is 3(m) (e.g., 3, 6, 9, 12).

In an embodiment and in addition to those described above, the Rh(I) catalyst can have the following formula:

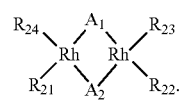

In an embodiment, $A_1$ and $A_2$ can each be independently selected from: a halogen, an acetate group, a sulfur-based ligand, a carbon-based ligand (e.g., alkyl, carbene, carbonyl), hydroxyl or alkyoxy, oxide or bridging ligands based on nitrogen, phosphorus or hydrogen (e.g., amido, phosphide, phosphido, nitride, hydride). In an embodiment, $R_{21}$, $R_{22}$, $R_{23}$, or $R_{24}$ can each be independently selected from: an alkyl, an aryl, an acetate, a cyano group, an olefin, an imine, an ether, a nitrile, a ketone, water, a sulfur based ligand, a phosphine, an N-heterocyclic carbene, or other neutral ligands. In an embodiment, the Rh(I) catalyst can be:

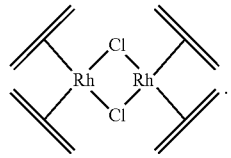

In an embodiment, the Rh(I) catalyst can have the following structure:

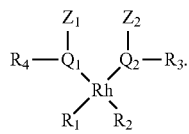

In an embodiment, $Q_1$ and $Q_2$ can be independently selected from: N, O, P, S, C, or Si. In an embodiment, $Z_1$ and $Z_2$ can be independently selected from: a halide, an alkyl, an alkenyl, a carbocycle group, a heterocycle, an aryl, a heteroaryl, an acetate, or related substituents (e.g., carboxylates, amines, phosphides, nitrogen-based, phosphorous-based, silicon-based). Optionally, $Z_1$ and $Z_2$ can joined together with a bond to form a 4, 5, 6, 7, 8 or 9-membered ring.

In an embodiment, $R_1$ and $R_2$ can be independently selected from: a radical group such as hydrogen, an alkyl, an aryl, an acetate, or a cyano group, or a neutral group such as an olefin, an imine, an ether, a nitrile, a ketone, water, a sulfur based ligand, a phosphine, N-heterocyclic carbene, or other neutral ligand (e.g., heteroaryl, amines). In an embodiment, $R_3$ and $R_4$ can be independently selected from: a halide, an alkyl, an alkenyl, a carbocycle group, a heterocycle, an aryl, a heteroaryl, an acetate, a cyano group, and other related substituent (e.g., phosphorus- and/or sulfur-based substituents).

In an embodiment, the Rh(I) catalyst can have the following structure:

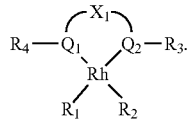

In an embodiment, $X_1$ can be selected from: $-(CR_{5(2)})_q-$, $=(CR_5)_r-$, $=(CR_5CR_{6(2)})_s-$, $=CR_5CR_6=$, and the like. In an embodiment, $R_5$ and $R_6$ can be independently selected from: hydrogen, a halide, an alkyl, an alkenyl, a carbocycle group, a heterocyclo, an aryl, a heteroaryl, an acetate, a cyano group, or related substituent. In an embodiment, each of q, r, and s are independently selected from 1 to 6.

In an embodiment, the Rh(I) catalyst can have the following structure:

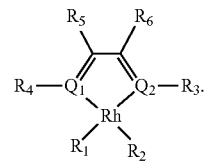

In an embodiment, the Rh(I) catalyst can be one of the following:

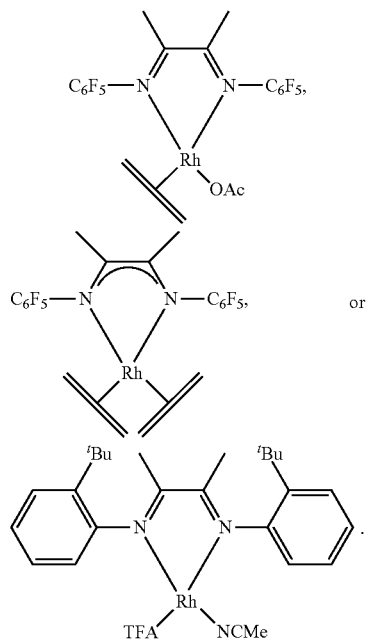

In an embodiment, the Rh(I) catalyst can have the following formula:

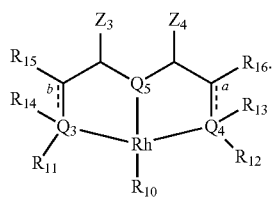

In an embodiment, $Q_3$, $Q_4$, and $Q_5$ can be independently selected from: N, O, P, S, C or Si. In an embodiment, $Z_3$ and $Z_4$ can be independently selected from: a halide, an alkyl, an alkenyl, a carbocycle group, a heterocyclo, an aryl, a heteroaryl, an acetate, a cyano group, or related substituent. In an embodiment, optionally, $Z_3$ and $Z_4$ can joined together with a bond to form a 5, 6, or 7-membered ring. "a" on the rings indicates that the bond can be a single or double bond depending upon $Q_3$ and $Q_4$.

In an embodiment, $R_{12}$ and $R_{12}$ can be independently selected from: a radical such as hydrogen, an alkyl, an aryl, an acetate, or a cyano group, or a neutral moiety such as an olefin, an imine, an ether, a nitrile, a ketone, water, a sulfur based ligand, a phosphine, an N-heterocyclic carbene, or other neutral ligand. In an embodiment, $R_{10}$, $R_{13}$, $R_{14}$ $R_{15}$, and $R_{16}$ can each be independently selected from: a halide, an alkyl, an alkenyl, a carbocycle group, a heterocyclo, an aryl, a heteroaryl, an acetate, a cyano group, or related substituent. In an embodiment, optionally, $R_{15}$ and $R_{14}$, or $R_{14}$, or $R_{11}$, or $R_{11}$, $R_{14}$, and $R_{15}$ can be joined together with a bond(s) to form a 5, 6, or 7-membered ring. In an embodiment, optionally, $R_{16}$ and $R_{13}$, or $R_{13}$ and $R_{12}$, or $R_{12}$, $R_{13}$, and $R_{16}$ can be joined together with a bond(s) to form a 5, 6, or 7-membered ring.

In an embodiment, the Rh(I) catalyst can have the following formula:

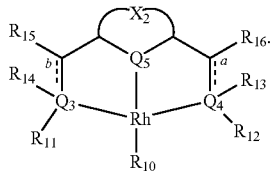

In an embodiment, $X_2$ can be selected from: $(CR_{5(2)})_q$—, =$(CR_5)_r$, =$(CR_5CR_{6(2)})_s$—, =$CR_5CR_6$=, and the like. In an embodiment $R_5$ and $R_6$ can each be independently selected from: hydrogen, a halide, an alkyl, an alkenyl, a carbocycle group, a heterocyclo, an aryl, a heteroaryl, an acetate, a pivalate, a hexanoate, and the like. In an embodiment, each of Q, R, and S can be independently selected from 1 to 6. "a" on the rings indicates that the bond can be a single or double bond depending upon $Q_3$ and $Q_4$.

In an embodiment, the Rh(I) catalyst can have the following formula:

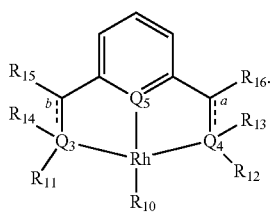

In an embodiment, the Rh(I) catalyst can include:

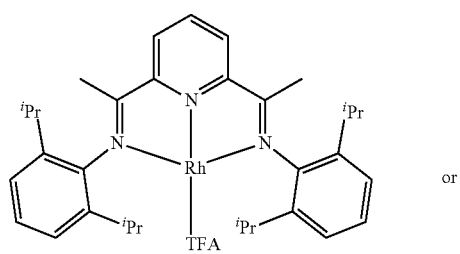

or

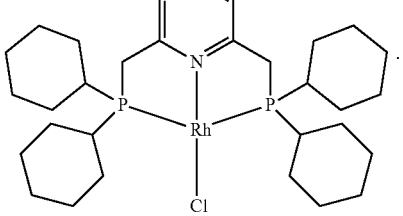

In regard to an aspect of the present disclosure, the Rh pre-catalyst, the Rh pre-catalyst can be a rhodium material that is insoluble but can release the active catalyst under reaction conditions. In an aspect, the Rh pre-catalyst can be Rh nanoparticles (e.g., about 5 to 500 nm in diameter or longest dimension) on a support (e.g., a metal oxide or carbon-based material as well as other similar supports that serve the same function as these do) or a single atom Rh material on a support (e.g., a zeolite materials as well as other similar supports that serve the same function as these do).

EXAMPLES

Now having described the embodiments of the disclosure, in general, the examples describe some additional embodiments. While embodiments of the present disclosure are described in connection with the example and the corresponding text and figures, there is no intent to limit embodiments of the disclosure to these descriptions. On the contrary, the intent is to cover all alternatives, modifications, and equivalents included within the spirit and scope of embodiments of the present disclosure.

Example 1

The synthetic routes to stilbenes is of interest in organic chemistry since stilbene derivatives are potentially applicable in the pharmaceutical industry and in materials science.[1] Many stilbene derivatives exhibit photophysical and photochemical properties that render them useful in dyes, liquid crystals and LEDs.[2-5] In addition, some products of medicinal interest possess stilbene (i.e., 1,2-diarylethylene) structures. For example, resveratrol is commonly used as a dietary supplement that has been observed to possess chemopreventive and cytostatic properties against a variety of human tumor cell lines, including several prostate cancer cell lines.[6, 7] Some resveratrol derivatives, such as DMU-212, have been shown to possess cytotoxic activity in ovarian, breast, and colorectal cell lines.[8]

Synthetic routes to stilbenes feature cross-coupling of arenes and styrenes,[9, 10] but these methods frequently require substrates to be activated with a functional group, resulting in undesirable multi-step substrate synthesis and by-products from the stilbene synthesis (FIG. 1a).[11] For example, the synthesis of alkenyl arenes has been achieved with halo-, diazonium- and sulfone-substituted arenes, as well as carboxyl- and nitroalkenes, but these processes produce stoichiometric amounts of waste.[12-19] In addition, there are synthetic inefficiencies associated with the generation of the initial functionalized substrates. Thus, introducing arenes and olefins into C—C bond forming processes via C—H bond breaking (rather than C-halogen bond activation, for example) offers potential advantages. However, in many cases of arene alkenylation involving transition metal-mediated C—H activation, directing groups are required to enhance reactivity toward arene C—H activation and/or promote regioselectivity. This limits the scope of substrates that can be used for arene alkenylation via C—H bond breaking reactions. For example, amines, amides and carbamates have been used to allow site-selective functionalization of C—H bonds with C—H activation and subsequent alkenylation typically occurring at the ortho position.[20]

Arene alkyl- and alkenylation provide an opportunity to affect more atom-economical formation of carbon-carbon bonds between inexpensive arenes and alkenes through undirected C—H activation (FIG. 1b). It has been reported that Ni,[21,22] Ru,[23-33] Pt[27, 34-40] and Ir[41-45] complexes catalyze olefin hydroarylation (non-oxidative) to produce saturated alkyl arenes, and Pd[46-52] and Rh[53-61] catalyze oxidative arene alkenylation using oxidants in many cases with functionalized olefins. We envisioned a strategy in which the reaction between arenes and styrenes in the presence of a rhodium catalyst precursor would form stilbene products through a rhodium-mediated C—H activation followed by vinyl arene insertion, β-hydride elimination and catalyst regeneration by an air-recyclable copper(II) oxidant (FIG. 1c). Herein, we report aerobic Rh-catalyzed synthesis of stilbenes from styrenes and arenes with good functional group tolerance. Under optimized conditions, these products can be obtained in moderate to good yields using dioxygen from the air as a terminal oxidant. For select cases, we compared the efficacy of Rh- and Pd-based catalysis and find that there are notable differences between those two metals in both selectivity and reactivity.

Results and Discussion

We examined benzene and styrene as model substrates to determine if there are differences using various Rh catalyst precursors. The catalysis between the commercially available RhCl$_3$·H$_2$O and [Rh(μ-OAc)(η$^2$—C$_2$H$_4$)$_2$]$_2$ (1) was first compared (Table 1, entries 1 and 2). The Rh(I) dimer 1 gave better yield (71% vs. 65%) perhaps because the presence of the acetate groups facilitates C—H activation via a concerted metalation/deprotonation (CMD) mechanism.[54,62-66] Previously, we have shown that Rh-catalyzed arene alkenylation using hydrocarbons does not occur in the absence of a source of carboxylate (either a Cu(II) salt or a carboxylic acid).[53-57] When the reaction temperature is raised from 150° C. to 165° C., higher yield is observed after 24 hours (81% vs. 71%), although this is accompanied the conversion of the arene to aryl ester (e.g., phenyl pivalate) due to a side reaction with copper(II) pivalate. The yield of stilbenes was minimally affected when styrene was used as a limiting reagent. Utilization of dimethylformamide (DMF), hexafluorobenzene or mesitylene furnished lower yields (0%, 12% and 11%, respectively), and we suspect this is a result of slower C—H activation due to lower concentrations of arene. It has been reported that the addition of vanadium (V) oxide will facilitate alkenylation reactions;[67, 68] however, when V$_2$O$_5$ was added in equal amount relative to copper(II) pivalate, yields were decreased (see entry 9). It was reported that in our Pd-catalyzed olefin alkenylation chemistry, the present of water inhibits the catalysis.[48] We also examined the influence of drying agents, however neither molecular sieves nor graphene oxide (entries 10 and 11) improve the yield of stilbenes.

TABLE 1

Comparison of different Rh precursors and optimization of reaction conditions using [Rh(μ-OAc)(η$^2$-C$_2$H$_4$)$_2$]$_2$ (1).

| entry | [Rh] | solvent[d] | HOPiv (equiv.[c]) | temp (° C.) | additive | yield[e] |
|---|---|---|---|---|---|---|
| 1 | RhCl$_3$·H$_2$O | benzene | 240 | 150 | — | 69 |
| 2 | 1 | benzene | 240 | 150 | — | 66 |
| 3 | 1 | benzene | 240 | 165 | — | 81 |
| 4 | 1 | benzene | 800 | 165 | — | 92 |
| 5 | 1 | benzene | 1600 | 165 | — | 20 |
| 6 | 1 | C$_6$F$_6$ | 800 | 165 | — | 12 |
| 7 | 1 | DMF | 800 | 165 | — | 7 |
| 8 | 1 | mesitylene | 800 | 165 | — | 39 |
| 9 | 1 | benzene | 800 | 165 | V$_2$O$_5$ | 36 |
| 10 | 1 | benzene | 800 | 165 | 4 Å MS | 90 |
| 11 | 1 | benzene | 800 | 165 | GO[f] | 58 |

[a]56 mmol when using benzene as solvent.
[b]Catalyst amount is relative to the limiting reagent styrene.
[c]Amounts of Cu(II) pivalate and pivalic acid are relative to Rh.
[d] In each case 5 mL of solvent were used.
[e]GC yield based on a calibration curve using hexamethylbenzene as internal standard.
[f]GO = Graphene oxide.

Under optimized conditions, we surveyed the scope and limitations of the Rh-catalyzed process with a variety of substituted styrene precursors (Table 2). The reactions between substituted styrenes and benzene showed good functional group tolerance and isolated yields. Tolerance of some halogen group was witnessed as reactions with halogenated styrenes afford expected stilbene derivatives 2f-2k with isolated yields >68%. The reaction also leaves alkoxy groups in 2o-2s untouched, which afforded an opportunity to synthesize protected resveratrol and derivatives using this approach (vide infra).

TABLE 2

Vinyl arene scope for benzene alkenylation catalyzed by [Rh(μ-OAc)(η$^2$-C$_2$H$_4$)$_2$]$_2$ (1) in neat benzene and isolated yields.

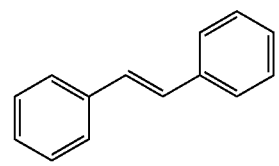

2a 92% yield

TABLE 2-continued
Vinyl arene scope for benzene alkenylation catalyzed by [Rh(μ-OAc)(η²-C₂H₄)₂]₂ (1) in neat benzene and isolated yields.
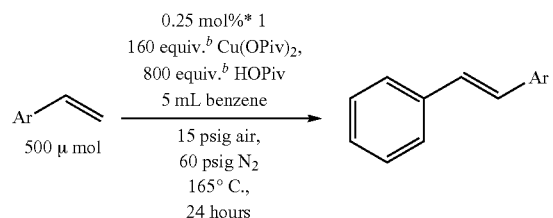
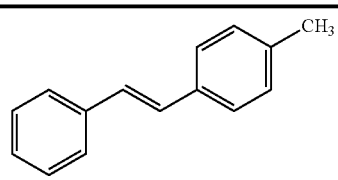
2b 87% yield
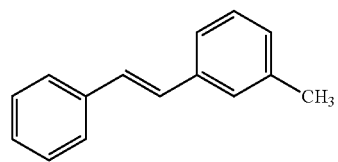
2c 82% yield
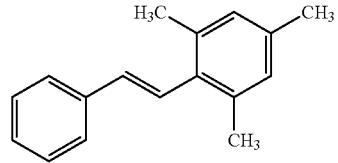 [SMILES: Cc1cc(C)c(/C=C/c2ccccc2)c(C)c1]
2d 47% yield[c]
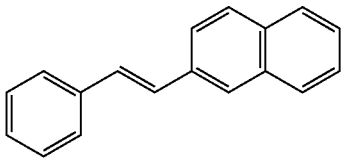 [SMILES: C(=C\c1ccc2ccccc2c1)/c1ccccc1]
2e 77% yield
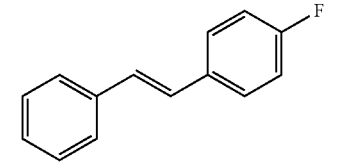 [SMILES: Fc1ccc(/C=C/c2ccccc2)cc1]
2f 79% yield
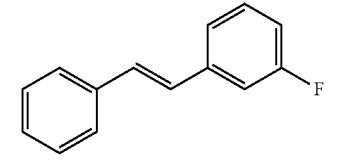
2g 84% yield
TABLE 2-continued
Vinyl arene scope for benzene alkenylation catalyzed by [Rh(μ-OAc)(η²-C₂H₄)₂]₂ (1) in neat benzene and isolated yields.
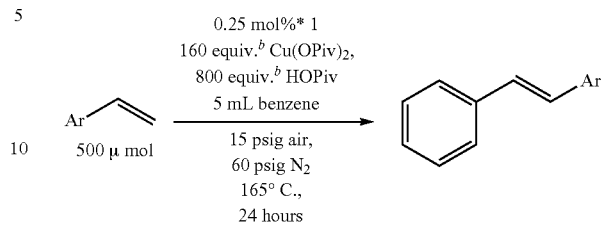
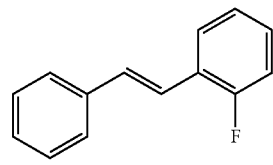 [SMILES: Fc1ccccc1/C=C/c1ccccc1]
2h 88% yield
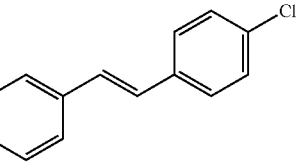
2i 74% yield
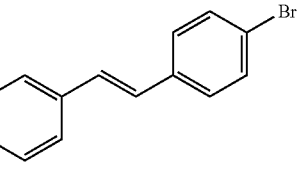
2j 72% yield
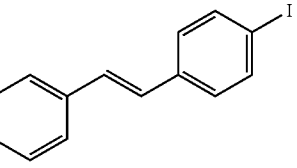
2k 68% yield
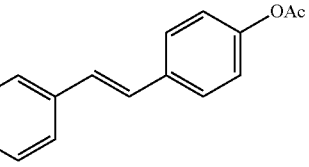
2l 88% yield
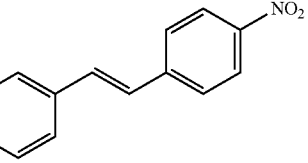
2m 73% yield TABLE 2-continued Vinyl arene scope for benzene alkenylation catalyzed by [Rh(μ-OAc)(η²-C₂H₄)₂]₂ (1) in neat benzene and isolated yields.

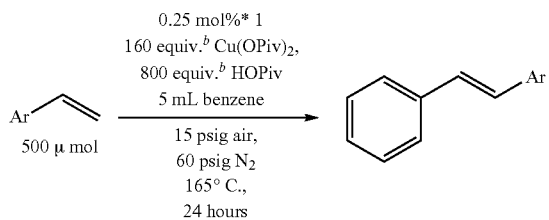

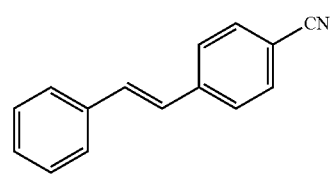 [SMILES: N#Cc1ccc(/C=C/c2ccccc2)cc1]

2n 72% yield

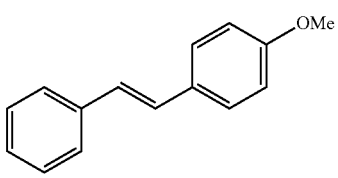 [SMILES: COc1ccc(/C=C/c2ccccc2)cc1]

2o 87% yield

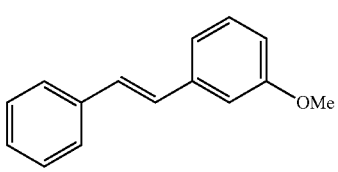 [SMILES: COc1cccc(/C=C/c2ccccc2)c1]

2p 83% yield

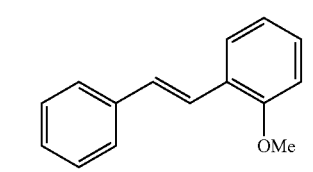 [SMILES: COc1ccccc1/C=C/c1ccccc1]

2q 79% yield

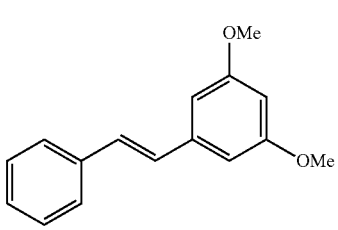 [SMILES: COc1cc(/C=C/c2ccccc2)cc(OC)c1]

TABLE 2-continued

Vinyl arene scope for benzene alkenylation catalyzed by [Rh(μ-OAc)(η²-C₂H₄)₂]₂ (1) in neat benzene and isolated yields.

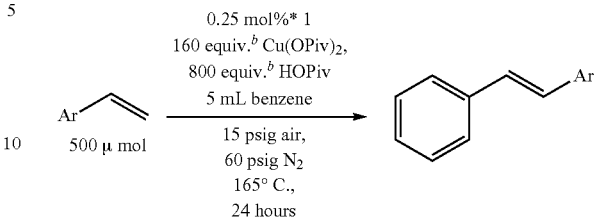

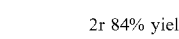

2r 84% yield

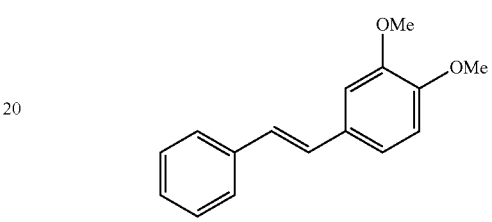

2s 82% yield

[a] Catalyst amount is relative to the limiting reagent styrene.
[b] Amounts of copper pivalate and pivalic acid are relative to single Rh.
[c] Reactions were performed for 48 hours.

We also examined extension of this method to α- and β-substituted styrenes (Scheme 1) and found that both α-methylstyrene and trans-β-methylstyrene gave the desired products 2t and along with products 2u and 2v, which are likely produced by a rhodium-mediated isomerization reaction. We propose two possible olefin isomerization routes to generate 2u and 2v (Scheme 2). We attribute the production of 2u to a side isomerization reaction from product 2u to 2v via a Rh hydride mediated process and production of 2v to a similar process that converts β-methylstyrene to allyl benzene which likely served as the precursor to 2v.

Figure 4A:
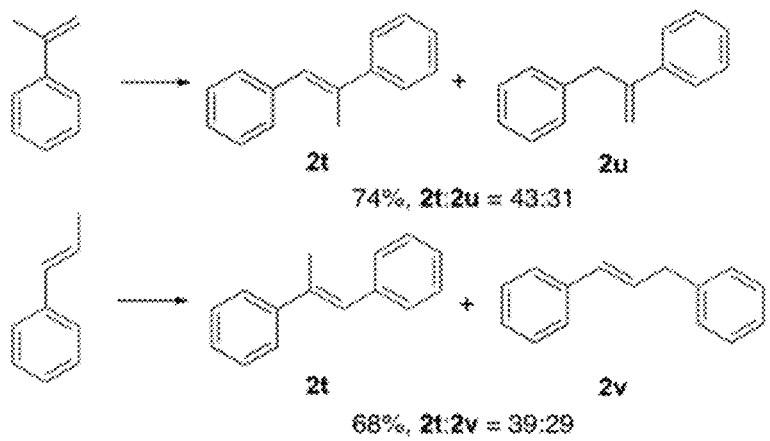
FIGS. 4A-C illustrate Schemes 1-3, respectively.

FIG. 4A, scheme 1 illustrates the alkenylation using vinyl substituted styrene of benzene. Condition: 0.25 mol % [Rh(μ-OAc)(η²—C₂H₄)₂]₂ (1) (0.5 mol % for single rhodium), 160 equiv. copper pivalate, 800 equiv. pivalic acid, 60 psig N₂, 15 psig air, 5 mL benzene as solvent, 165° C., 24 hours.

Figure 4B:
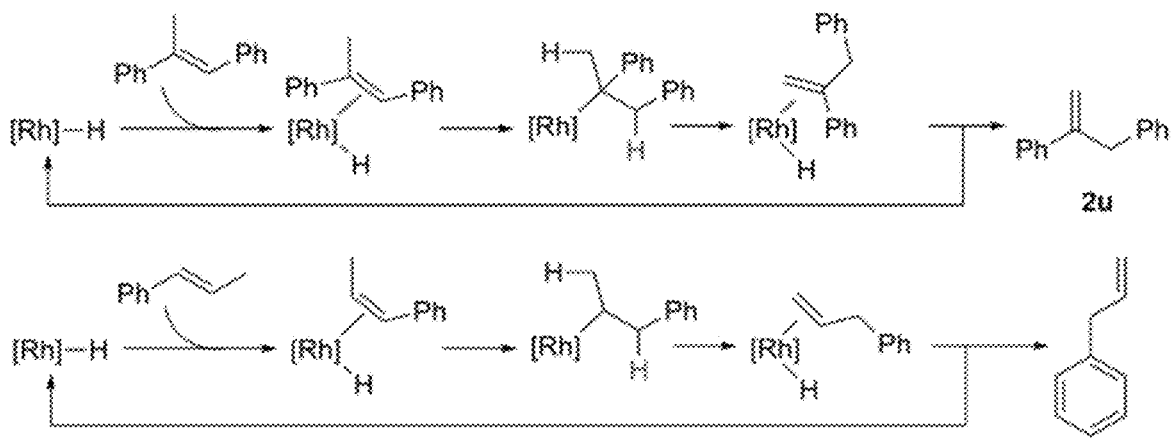

FIG. 4B, scheme 2, illustrates the Rh-mediated olefin isomerization that produces unexpected products 2u and 2v.

Table 3 shows isolated yields for catalytic reactions using substituted arenes and styrene. A range of monosubstituted arenes are functionalized to give products 3a-3d, 3i-3n, 3r, 3u and 3v, with electronic character ranging from electron-rich anisole (3r) to electron deficient α,α,α-trifluorotoluene. Regardless of the arene substituent identity, the reaction regioselectivity is catalyst-directed for the formation of meta and para products, generally with an approximate 2:1 ratio. For 3a, 3j, 3l and 3v, the meta- and para-functionalized isomers were separated using column chromatography to give ~2:1 isolated yields of meta:para products. These results indicate that the C—H activation step is sensitive to steric hindrance, with even small fluoro or methyl groups almost totally suppressing ortho functionalization. When dialkylbenzenes and trialkylbenzene 3e-3h were used as the substrate, we observed the same influence of sterics on the selectivity. Since all four arene C—H bonds in p-xylene 3e are adjacent to a methyl group, the reaction gave a low yield of only 22%. For m-xylene (3f) and o-xylene (3g), better yields (>70%) are obtained since they have more sterically accessible arene C—H bonds. 1,2,3-trimethylbenzene has a similar steric profile to meta-xylene (i.e., an accessible C—H bond that is meta to methyl groups), and the reaction gave 67% isolated yield of the desired product (3h) after prolonged reaction time (48 hours).

TABLE 3

Arene scope of oxidative styrene hydroarylation catalyzed by [Rh(μ-OAc)(η²-C₂H₄)₂]₂ (1) in neat arene solution. All yields are isolated.

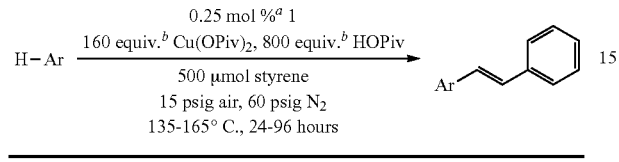

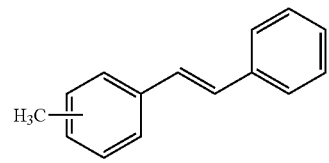

3a 76% total yield$^c$
para 2b 21% yield
meta 2c 47% yield
o:m:p$^d$ = 1:28:13

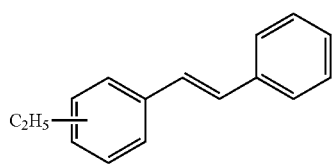

3b 81% total yield
o:m:p = 0:3:1

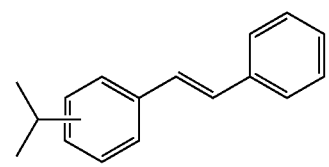

3c 77% total yield
o:m:p = 0:2:1

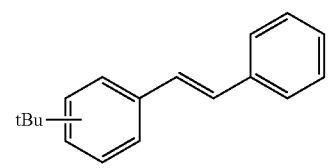

3d 81% total yield
o:m:p = 0:2:1

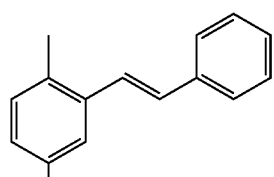

3e 22% yield$^e$

TABLE 3-continued

Arene scope of oxidative styrene hydroarylation catalyzed by [Rh(μ-OAc)(η²-C₂H₄)₂]₂ (1) in neat arene solution. All yields are isolated.

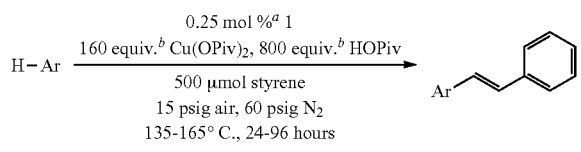

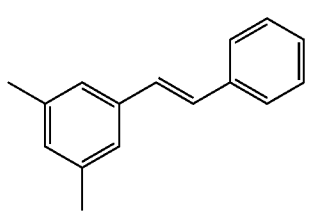 [SMILES: Cc1cc(C)cc(/C=C/c2ccccc2)c1]

3f 77% yield$^e$

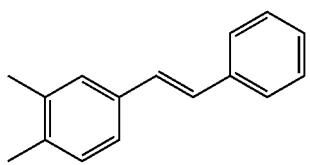 [SMILES: Cc1ccc(/C=C/c2ccccc2)cc1C]

3g 71% yield

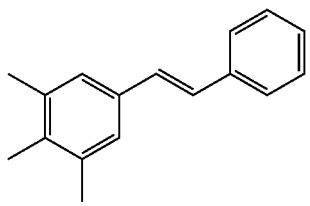 [SMILES: Cc1cc(/C=C/c2ccccc2)cc(C)c1C]

3h 67% yield$^e$

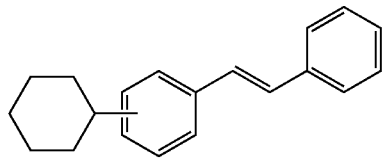

3i 81% total yield
o:m:p = 0:3:1

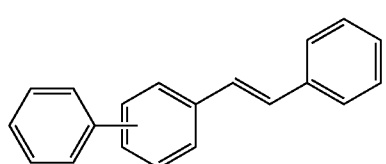

3j$^f$ 81% total yield
para 3ja 24% yield
meta 3jb 51% yield
o:m:p = 0:3:1

TABLE 3-continued

Arene scope of oxidative styrene hydroarylation catalyzed by [Rh(μ-OAc)(η²-C₂H₄)₂]₂ (1) in neat arene solution. All yields are isolated.

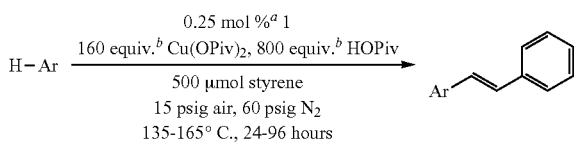

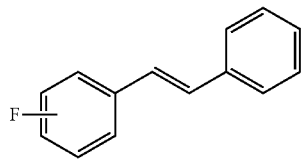

3k 82% total yield
o:m:p[g] = 1:28:23

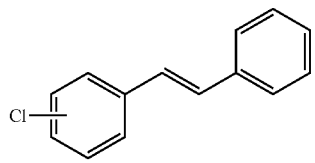

3l 87% total yield
para 3la 25% yield
meta 3lb 56% yield
o:m:p = 0:2:1

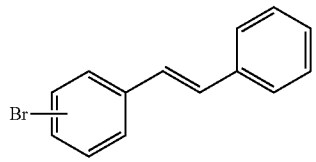

3m 69% total yield[h]
o:m:p = 0:2:1

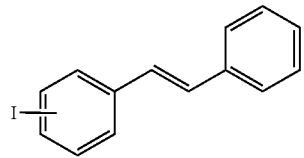

3n 44% NMR yield[i]
o:m:p = 0:2:1

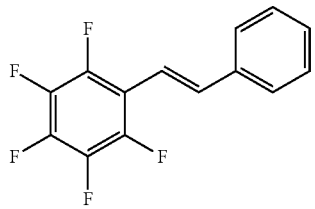 [SMILES: Fc1c(F)c(F)c(/C=C/c2ccccc2)c(F)c1F]

3o 61% yield[e]

TABLE 3-continued

Arene scope of oxidative styrene hydroarylation catalyzed by [Rh(μ-OAc)(η²-C₂H₄)₂]₂ (1) in neat arene solution. All yields are isolated.

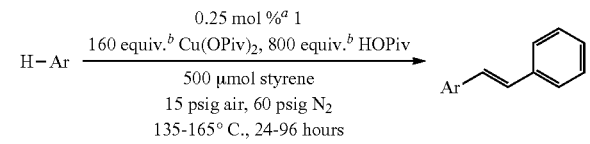

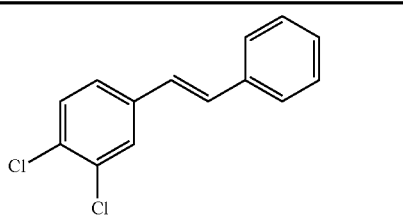

3p 74% yield

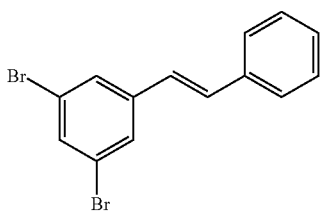 [SMILES: Brc1cc(Br)cc(/C=C/c2ccccc2)c1]

3q[j] 74% yield

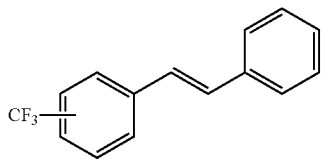

3r 87% total yield
o:m:p = 0:2:1

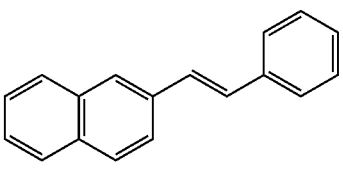 [SMILES: C(=C\c1ccc2ccccc2c1)/c1ccccc1]

3s[f] 75% total yield

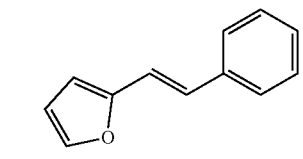 [SMILES: C(=C\c1ccco1)/c1ccccc1]

3t 49% yield

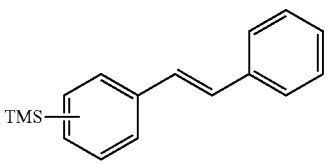

3u 91% total yield
o:m:p = 0:2:1

TABLE 3-continued

Arene scope of oxidative styrene hydroarylation catalyzed by [Rh(μ-OAc)(η²-C₂H₄)₂]₂ (1) in neat arene solution. All yields are isolated.

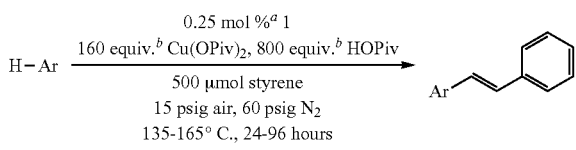

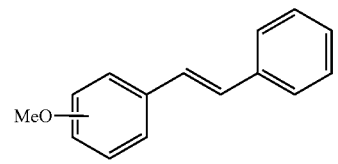

3v$^j$ 81% total yield
para 3va 19% yield
meta 3vb 43% yield
o:m:p = 0:3:1

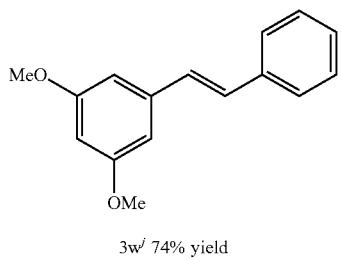

3w$^j$ 74% yield

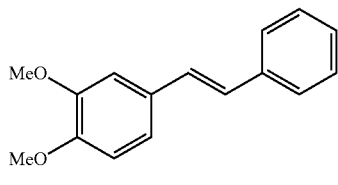 [SMILES: COc1ccc(/C=C/c2ccccc2)cc1OC]

3x$^j$ 73% yield

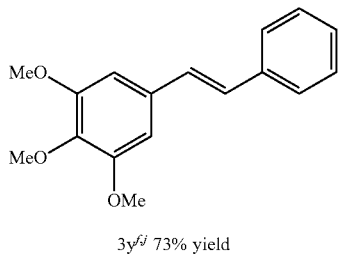

3y$^{f,j}$ 73% yield $^a$Catalyst amount is relative to the limiting reagent styrene.
$^b$Amounts of Cu(II) pivalate and pivalic acid are relative to Rh.
$^c$Total yield is calculated prior to isomer separation.
$^d$o.m.p value is calculated based on GC-FID peak areas.
$^e$Reaction was performed for 48 hours.
$^f$Mesitylene (2.5 mL) was added to the reaction mixture.
$^g$The o:m:p value is calculated based on ¹⁹F NMR spectroscopy due to poor resolution of isomers in the GC.
$^h$The yield was calculated based on the integration of the vinyl protons of bromostilbene relative to the internal standard CH₃NO₂.
$^i$The crude reaction mixture was washed with base and analyzed by ¹H NMR spectroscopy. The yield was calculated based on the integration of the vinyl protons of iodostilbene relative to the internal standard CH₃NO₂.
$^j$Reactions were performed at 135° C. for 96 hours with reactors were opened to air every 24 hours.

With respect to halogenated arenes, the reactions proceed for fluoro- and chlorobenzene with total isolated yields (all isomers) of 82% (3k) and 87% (3l), respectively. However, reactions are less successful with bromo- and iodobenzene due to C—X bond functionalization competing with C—H activation. Thus, along with the desired products bromo- (3m) and iodostilbene (3n), (E)-stilbene (2a) is formed. The reaction works well for pentafluorobenzene (3o), ortho-dichlorobenzene (3p) and meta-dibromobenzene (3q, under 135° C.) giving 61, 74 and 74% isolated yields, respectively. When using the arenes with methoxy groups (3v-3y), a decrease in yield at 165° C. is observed. But the yields can be improved by lowering the reaction temperature to 135° C. and extending reaction time to 96 hours. We expanded the scope of the catalysis to polycyclic arenes and heteroaromatic substrates. The reactions with naphthalene (3u) and furan (3v) are selective and generate the expected alkenylation products in moderate to good yields.

Figure 2:
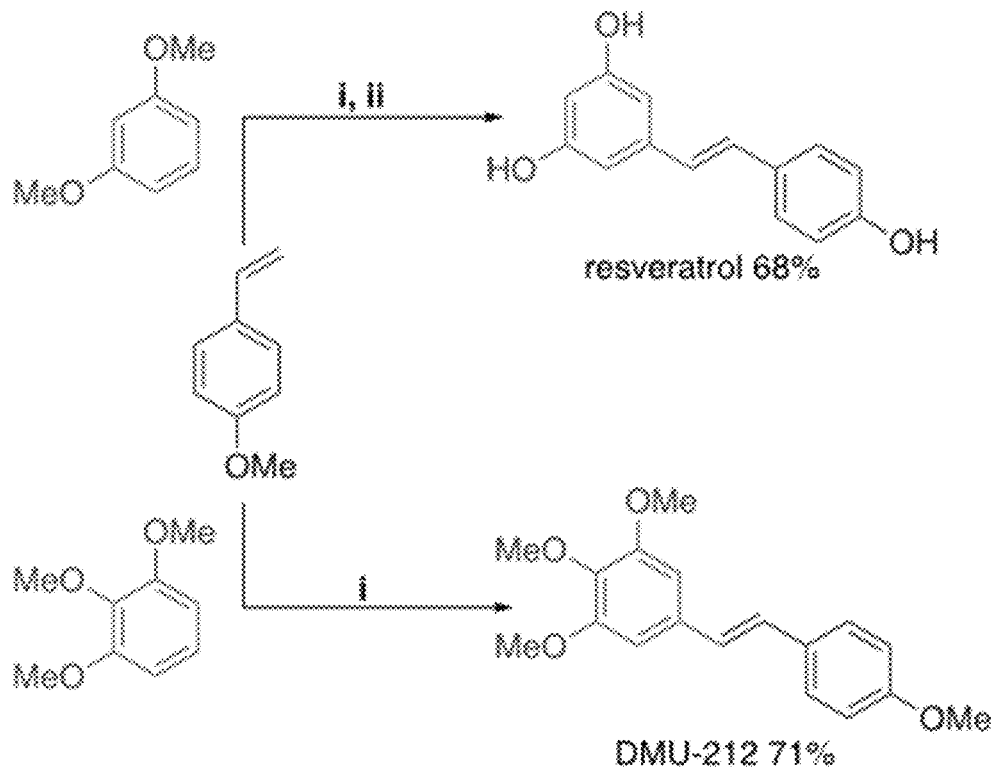
FIGS. 2A and B illustrate Rh-catalyzed direct synthesis of bioactive molecules.
FIG. 2B illustrates building blocks for synthesis of future pharmaceutically relevant molecules that can be catalytically coupled using the rhodium catalyzed arene alkenylation.
Figure 2:
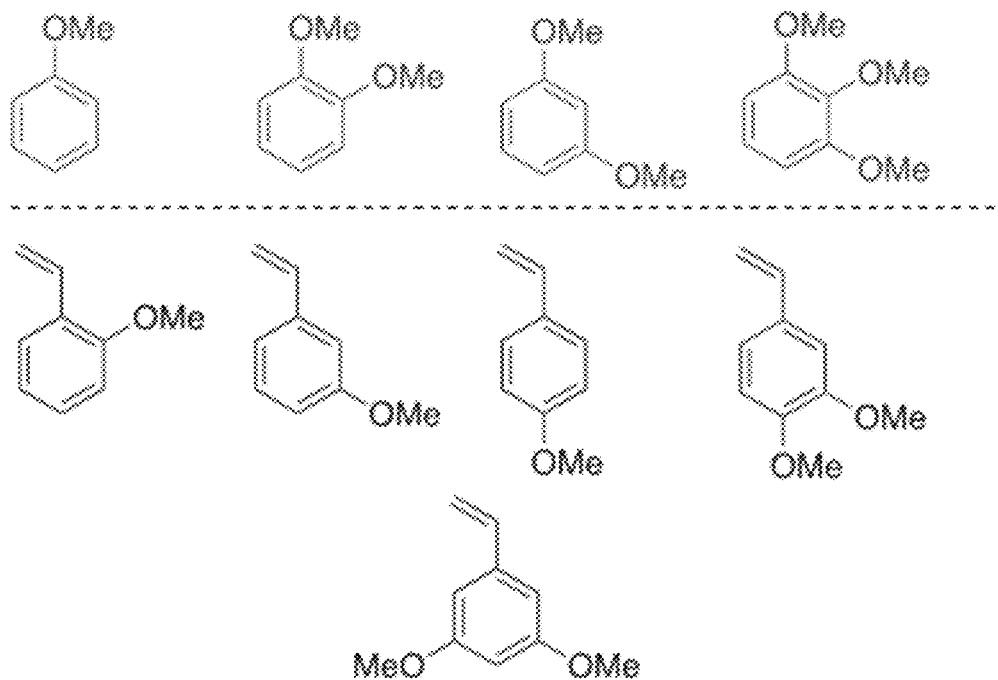

It has been reported that polyphenolics compounds and methyl ether derivatives possess possible anti-cancer bioactivity.[6-8, 69-87] Among those molecules, resveratrol and DMU-212 are two widely studied compounds. Current synthetic routes for resveratrol and derivatives use Wittig reactions, Perkin condensations, alkene metathesis, and cross-coupling.[70, 72, 77, 80, 88-90] Decarbonylative Heck coupling and Perkin condensations can produce polyhydroxystilbenes at moderate yields (~50%) in four and two steps, respectively.[70, 88] Alkene metathesis can generate polymethoxystilbenes in two steps at high conversions, but with low selectivity against self-metathesis products.[91] Wittig reactions can generate polymethoxystilbenes in one step with high yield, but require aqueous conditions and the in situ formation of trialkylphosphonium salts.[92] Using our method, DMU-212 and resveratrol can be prepared from poly-methoxybenzene and vinyl anisole in 68% and 71% yield by a single- or two-step conversion(s), respectively (FIG. 2a).

Other than resveratrol and DMU-212, many other polyphenolics and their methyl esters can be synthesized using our strategy since we have demonstrated our method works well on polymethoxybenzene (3v-3y) and vinyl-methoxybenzenes (2p-2t), the reaction between these substrates could produce more than 20 different polymethoxystilbenes.

Figure 4C:
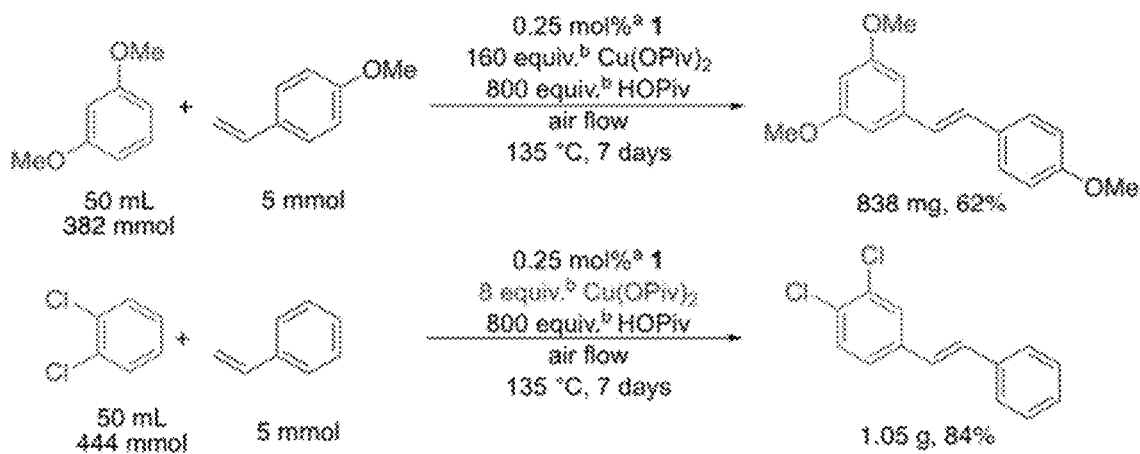

Hyperbaric dinitrogen pressure is used for arenes with boiling points lower than the reaction temperature. For selected high-boiling-point arene substrates, the catalysis could be performed under ambient pressure allowing us to use simple reaction set ups equipped with a continuous air feed to enable larger scale synthesis. As shown in Scheme 3, the reaction between 1,3-dimethoxybenzene and 4-vinylanisole yields 62% (838 mg) of desired product (E)-1,3-dimethoxy-5-(4-methoxystyryl)benzene (trimethylresveratrol). The continuous air flow created a stable O₂ concentration and lower copper loading is possible. As shown in FIG. 4C, Scheme 3, the Cu(II) loading was reduced to 8 equiv. (relative to Rh) in the reaction between dichlorobenzene and a yield of 84% (1.05 g) of desired product 3p was isolated. Scheme 3 illustrates gram-scale synthesis of (E),1,3-dimethoxy-5-(4-methoxystyryl)benzene and (E)-1,2-dichloro-4-styrylbenzene (3p), where: $^a$Catalyst amount is relative to the limiting reagent styrene; and where: $^b$Amounts of Cu(II) pivalate and pivalic acid are relative to Rh.

Figure 3:
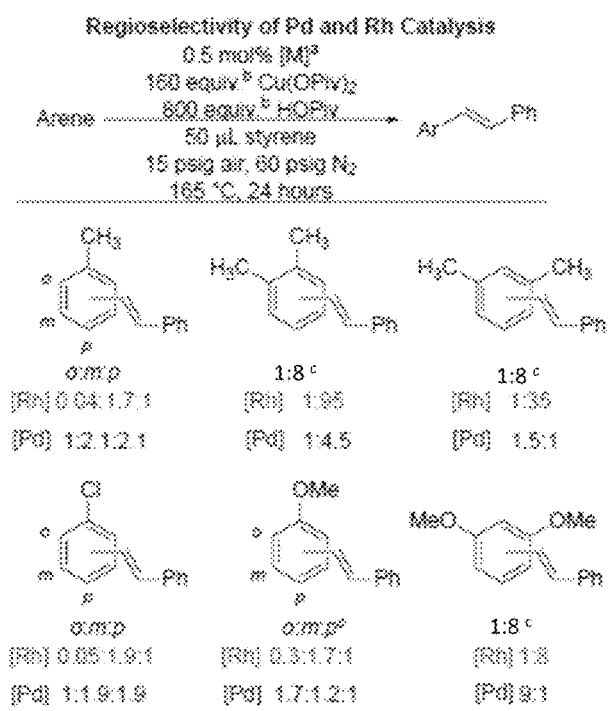
FIGS. 3A-C illustrate the difference between rhodium and palladium catalysis.
Figure 3:
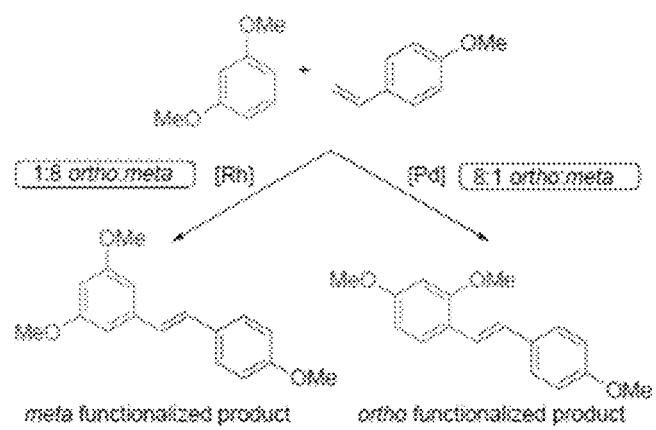
Figure 3:
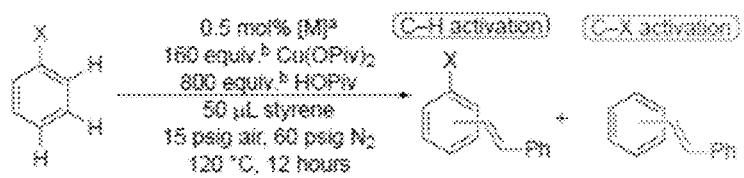

We also examined aerobic arene alkenylation for stilbene production using Pd(OAc)₂ (4), previously reported to serve as a catalyst for arene alkenylation despite low selectivity.[48, 49] We first investigated the regioselectivity of palladium catalysis. As shown in FIG. 3a, Pd catalysis leads to substantial amounts of ortho functionalization in all six arenes investigated, whereas ortho functionalization in rhodium catalyzed reactions was minimal. A directing group effect was observed when using anisole as the substrate, but this effect was more heavily pronounced for Pd than for Rh.

Using 4 as the catalyst precursor, the ortho:meta selectivity for 1,3-dimethoxybenzene with styrene (FIG. 3a) is 9:1 in favor of ortho functionalization and with 4-methoxystyrene (FIG. 3b) is 8:1 in favor of ortho functionalization. In contrast, ortho:meta selectivity for 1,3-dimethoxylbenzene with styrene and 4-methoxystyrene using the Rh catalyst 1 are both 1:8, favoring the meta product.

We also investigated Pd catalysis using halogenated arenes as substrate (FIG. 3c) at 120° C. where the consumption of the functionalized product (observed in Pd catalysis) is minimal. Using chlorobenzene, the desired product mixture (ortho, meta and para isomers) can be obtained after 12 hours under reaction conditions and the same product distribution (approximately 1:2:2 ortho:meta:para) is observed. It has been reported that Rh-catalyzed oxidative olefination of bromoarene favors formation of the C—H bond activation product;[93] we observe similar selectivity with Rh catalysis when using bromo- or iodobenzene as the substrate, with Pd showing much lower tolerance toward halide functionality. The reaction of bromobenzene with 4 produces a large amount of stilbene, with a 1:3 ratio of stilbene:bromostilbene, which likely results from C—Br bond activation in lieu of C—H bond activation. When using iodobenzene, the reaction produces trace amounts of iodostilbene, which indicated that Pd favors activation of C—I over C—H bonds. In contrast, Rh has shown better tolerance towards bromo and iodo functionalities. Catalysis with 1 using bromobenzene still favors C—H activation product bromostilbene over the C—Br activation product stilbene and the ratio of the former to the latter is 11:1. The reaction with iodobenzene is less selective, but still slightly favors producing C—H activation product (the observed ratio of iodostilbene to stilbene is 1.1).

Summary and Conclusions

We have developed a new, broadly applicable strategy for the one-pot aerobic synthesis of stilbenes by Rh-catalyzed oxidative arene alkenylation. Whereas conventional methods for arene alkenylation require prefunctionalized substrates, our approach makes use of C—H bond activation, without the need for prefunctionalization with a weaker bond C—X bond (X=halide or pseudo-halide) or directing group. The new arene alkenylation chemistry is tolerant of fluoride, chloride, trifluoromethyl, ester, nitro, acetate, cyanide and ether groups on both the arene and alkene in uniformly good to high yield and with predictable regioselectivity without the need to identify or develop catalytic systems for each class of reagent. This performance presents an opportunity for large-scale organic synthesis of commercially relevant stilbenes, including those with medicinal properties.

EXPERIMENTAL SECTION

General Considerations. Unless otherwise noted, all synthetic procedures were performed under aerobic conditions. Glovebox purity was maintained by periodic nitrogen purges and was monitored by an oxygen analyzer ($O_2$<15 ppm for all reactions). Benzene was purified by passage through an column of activated alumina column. $^1$H NMR spectra were recorded on a Varian 600 spectrometer. $^1$H NMR spectra are referenced against residual proton signals ($^1$H NMR) of the deuterated solvents. GC/MS was performed using a Shimadzu GCMS-QP2010 Plus system with a 30 m×0.25 mm RTx-Qbond column with 8 μm thickness using electron impact ionization. GC/FID was performed using a Shimadzu GC-2014 system with a 30 m×90.25 mm HP5 column with 0.25 μm film thickness. For initial catalytic experiments without isolation of product, stilbene yields were quantified using linear regression analysis of gas chromatograms of standard samples of authentic product. The slope, correlation coefficient and the response factor of the regression line are 0.83, 0.99 and 0.80 for stilbene. Copper(II) pivalate and di-μ-acetatotetrakis(dihaptoethene)dirhodium(I) (1) was synthesized according to a published procedure.[94,95] All other reagents were used as received from commercial sources. High resolution mass spectrometry was performed at the University of Kansas Mass Spectrometry Lab.

Optimization of reaction condition. Under an atmosphere of dry nitrogen, di-μ-acetatotetrakis(dihaptoethene)dirhodium(I) (1) (2.5 μmol, 550 μg), copper(II) pivalate (400 μmol, 106 mg), and pivalic acid (2 mmol, 204 mg) were added into a dried Andrews Glass™ Lab-Crest® Fisher-Porter tube with a stir bar. Styrene (500 μmol, 57 μL), and benzene (5 mL) were then added by syringe. The tube was opened to air, sealed and pressurized with dinitrogen (60 psig), and the mixture was stirred at 165° C. After 24 h, the reaction was allowed to cool to room temperature. The resultant mixture was diluted with ethyl acetate (40 mL), washed with saturated sodium carbonate solution (50 mL). The aqueous and organic layers were separated. The aqueous layer was extracted with ethyl acetate (3×40 mL), and the combined organic layers were washed with water (3×10 mL) and dried over magnesium sulfate. The resulting sample was subjected to GC-FID analysis. All yields and ratios given during the optimization studies were determined by GC-FID analysis of the crude reaction mixture using hexamethylbenzene as an internal standard.

Scope of vinyl arene. Under an atmosphere of dry nitrogen, di-μ-acetatotetrakis(dihaptoethene)dirhodium(I) (1) (2.5 μmol, 550 μg), copper(II) pivalate (400 μmol, 106 mg), and pivalic acid (2 mmol, 204 mg) were added into a dried Andrews Glass™ Lab-Crest® Fisher-Porter tube with a stir bar. Then vinyl arene (500 μmol) and benzene (5 mL) were added by syringe. Then the tube was opened to air, sealed and pressurized with dinitrogen (60 psig). The mixture was stirred at 165° C. After 24 h, the reaction was allowed to cool to room temperature. The resultant mixture was diluted with ethyl acetate (40 mL) and washed with saturated sodium carbonate solution (50 mL). The aqueous and organic layers were separated. The aqueous layer was extracted with ethyl acetate (3×40 mL) and the combined organic layers were washed with water, (3×10 mL), dried over magnesium sulfate, filtered, and concentrated under vacuum.

Scope of arenes. Under an atmosphere of dry nitrogen, di-μ-acetatotetrakis(dihaptoethene)dirhodium(I) (1) (2.5 μmol, 550 μg), copper(II) pivalate (400 μmol, 106 mg) and pivalic acid (2 mmol, 204 mg) were added to a dried Andrews Glass™ Lab-Crest® Fisher-Porter tube with a stir bar. Then styrene (500 μmol) and arene (5 mL) were added by syringe. The tube was opened to air, sealed and pressurized with dinitrogen (60 psig). The mixture was stirred at 165° C. After 24 h, the reaction was allowed to cool to room temperature. The resultant mixture was diluted with ethyl acetate (40 mL) and washed with saturated sodium carbonate solution (50 mL). The aqueous and organic layers were separated. The aqueous layer was extracted with ethyl acetate (3×40 mL), and the combined organic layers were washed with water (3×10 mL) and dried over magnesium sulfate, filtered, and concentrated under vacuum. The concentrate was purified by column chromatography using hexanes as eluent.

Synthesis of bioactive stilbenes derivatives. Under an atmosphere of dry nitrogen, di-μ-acetatotetrakis(dihaptoethene)dirhodium(I) (1) (2.5 μmol, 550 μg), copper(II) pivalate (400 μmol, 106 mg) and pivalic acid (2 mmol, 204 mg) were added to a dried Andrews Glass™ Lab-Crest® Fisher-Porter tube with a stir bar. Then, vinyl arene (500 μmol) and arene (5 mL) were added by syringe. The tube was opened to air, sealed and pressurized with dinitrogen (60 psig). The mixture was stirred at 135° C. for 96 hours. After every 24 h, the reaction was allowed to cool to room temperature and fresh air was purged into the reactor via a long needle. After the reaction finished, the resultant mixture was diluted with ethyl acetate (40 mL) and washed with saturated sodium carbonate solution (50 mL). The aqueous and organic layers were separated. The aqueous layer was extracted with ethyl acetate (3×40 mL), and the combined organic layers were washed with water (3×10 mL), dried over magnesium sulfate, filtered and concentrated under vacuum. The concentrate was purified by column chromatography using 9:1 hexanes:ethyl acetate as eluent.

Gram scale synthesis. An oven dried 250 mL two-neck round bottom flask was charge with di-μ-acetatotetrakis(dihaptoethene)dirhodium(I) (1) (25 gmol, 5.5 mg, 0.5 mol %), copper(II) pivalate and pivalic acid. To the flask 50 mL of arene were added. The solution was stirred at room temperature for 10 minutes to dissolve all of the copper salt. Then, 5 mmol of vinyl arene were added to the reaction mixture. The reaction flask was connected to compressed air via an adapter and a condenser (note: the air flow will facilitate the removal of the reaction solvent; thus, a long condenser is needed). The reaction mixture was stirred at optimized temperature for the arene. After completion of the reaction, the flask was allowed to cool to room temperature. The resultant mixture was diluted with ethyl acetate (150 mL) and washed with saturated sodium carbonate solution (200 mL). The aqueous and organic layers were separated. The aqueous layer was extracted with ethyl acetate (3×200 mL), and the combined organic layers were washed with water (3×200 mL), dried over magnesium sulfate, filtered, and concentrated under vacuum. The product was purified by flash column chromatography using hexanes/ethylacetate as the eluent.

REFERENCES FOR EXAMPLE 1

1. Likhtenshtein, G., *Stilbenes: applications in chemistry, life sciences and materials science*. Wiley-VCH Verlag GmbH & Co. KGaA: Weinheim, 2010.
2. Wong-Wah-Chung, P.; Mailhot, G.; Bolte, M., 4,4'-Diaminostilbene-2,2'-disulfonate (DSD) behaviour: under irradiation in water. Decrease of its activity as a fluorescent whitening agent. *J. Photochem. Photobio. A* 2001, 138 (3), 275-280.
3. Ichimura, K., Photoalignment of Liquid-Crystal Systems. *Chem. Rev.* 2000, 100 (5), 1847-1874.
4. Halim, M.; Samuel, I. D. W.; Pillow, J. N. G.; Monkman, A. P.; Burn, P. L., Control of colour and charge injection in conjugated dendrimer polypyridine bilayer LEDs. *Synth. Met.* 1999, 102 (1-3), 1571-1574.
5. Morrall, J. P.; Dalton, G. T.; Humphrey, M. G.; Samoc, M. Organotransition Metal Complexes for Nonlinear Optic. In Advance in Organometallic Chemistry; Elsevier; New York, NY, USA, 2007; Volume 55, pp. 61-136. ISBN 978-0-12-373978-0.
6. Frémont, L., Biological effects of resveratrol. *Life Sci.* 2000, 66 (8), 663-673.
7. Vang, O.; Ahmad, N.; Baile, C. A.; Baur, J. A.; Brown, K.; Csiszar, A.; Das, D. K.; Delmas, D.; Gottfried, C.; Lin, H.-Y.; Ma, Q.-Y.; Mukhopadhyay, P.; Nalini, N.; Pezzuto, J. M.; Richard, T.; Shukla, Y.; Surh, Y.-J.; Szekeres, T.; Szkudelski, T.; Walle, T.; Wu, J. M., What is new for an old molecule? Systematic review and recommendations on the use of resveratrol. *PLoS One* 2011, 6 (6), e19881-e19881.
8. Schneider, Y.; Chabert, P.; Stutzmann, J.; Coelho, D.; Fougerousse, A.; Gossé, F.; Launay, J.-F.; Brouillard, R.; Raul, F., Resveratrol analog (Z)-3,5,4'-trimethoxystilbene is a potent anti-mitotic drug inhibiting tubulin polymerization. *Int. J. Cancer* 2003, 107 (2), 189-196.
9. Mochida, S.; Hirano, K.; Satoh, T.; Miura, M., Synthesis of stilbene and distyrylbenzene derivatives through rhodium-catalyzed ortho-olefination and decarboxylation of benzoic acids. *Org. Lett.* 2010, 12 (24), 5776-9.
10. Zhang, N.; Quan, Z. J.; Zhang, Z.; Da, Y. X.; Wang, X. C., Synthesis of stilbene derivatives via visible-light-induced cross-coupling of aryl diazonium salts with nitroalkenes using —NO2 as a leaving group. *Chem Commun (Camb)* 2016, 52 (99), 14234-14237.
11. Le Bras, J.; Muzart, J., Intermolecular dehydrogenative Heck reactions. *Chem. Rev.* 2011, 111 (3), 1170-214.
12. Heck, R. F.; Nolley, J. P., Palladium-Catalyzed Vinylic Hydrogen Substitution Reactions with Aryl, Benzyl, and Styryl Halides. *J. Org. Chem.* 1972, 37 (14), 2320-2322.
13. Schroll, P.; Hari, D. P.; Konig, B., Photocatalytic arylation of alkenes, alkynes and enones with diazonium salts. *ChemistryOpen* 2012, 1 (3), 130-3.
14. Baudin, J. B.; Hareau, G.; Julia, S. A.; Ruel, O., A Direct Synthesis of Olefins by Reaction of Carbonyl-Compounds with Lithio Derivatives of 2-[Alkyl-Sulfonyl or (2'-Alkenyl)-Sulfonyl or Benzyl-Sulfonyl]-Benzothiazoles. *Tetrahedron Lett.* 1991, 32 (9), 1175-1178.
15. Albéniz, A. C.; Espinet, P.; Martín-Ruiz, B.; Milstein, D., Catalytic System for the Heck Reaction of Fluorinated Haloaryls. *Organometallics* 2005, 24 (15), 3679-3684.
16. Albeniz, A. C.; Espinet, P.; Martin-Ruiz, B.; Milstein, D., Catalytic system for Heck reactions involving insertion into Pd-(perfluoro-organyl) bonds. *J. Am. Chem. Soc.* 2001, 123 (46), 11504-5.
17. Albeniz, A. C.; Espinet, P.; Focesfoces, C.; Cano, F. H., Pd(C6f5)Br, a Convenient Precursor for Studying the Endo Attack of Nucleophiles on Olefins—X-Ray Structure of Bis(Mu-Bromo)Bis(4-(Pentafluorophenyl)-1-3-Eta-3-Cyclohexenyl)Dipalladium(Ii). *Organometallics* 1990, 9 (4), 1079-1085.
18. Mochida, S.; Hirano, K.; Satoh, T.; Miura, M., Rhodium-Catalyzed Regioselective Olefination Directed by a Carboxylic Group. *The Journal of Organic Chemistry* 2011, 76 (9), 3024-3033.
19. Rodríguez, N.; Goossen, L. J., Decarboxylative coupling reactions: a modem strategy for C—C-bond formation. *Chem. Soc. Rev.* 2011, 40 (10), 5030-5048.
20. Kuhl, N.; Hopkinson, M. N.; Wencel-Delord, J.; Glorius, F., Beyond directing groups: transition-metal-catalyzed C—H activation of simple arenes. *Angew. Chem. Int. Ed. Engl.* 2012, 51 (41), 10236-54.
21. Saper, N. I.; Ohgi, A.; Small, D. W.; Semba, K.; Nakao, Y.; Hartwig, J. F., Nickel-catalysed anti-Markovnikov hydroarylation of unactivated alkenes with unactivated arenes facilitated by non-covalent interactions. *Nature Chemistry* 2020, 12 (3), 276-283.
22. Bair, J. S.; Schramm, Y.; Sergeev, A. G.; Clot, E.; Eisenstein, O.; Hartwig, J. F., Linear-Selective Hydroarylation of Unactivated Terminal and Internal Olefins with Trifluoromethyl-Substituted Arenes. *Journal of the American Chemical Society* 2014, 136 (38), 13098-13101.
23. Lail, M.; Arrowood, B. N.; Gunnoe, T. B., Addition of arenes to ethylene and propene catalyzed by ruthenium. *J. Am. Chem. Soc.* 2003, 125 (25), 7506-7.
24. Lail, M.; Bell, C. M.; Conner, D.; Cundari, T. R.; Gunnoe, T. B.; Petersen, J. L., Experimental and computational studies of ruthenium(II)-catalyzed addition of arene C—H bonds to olefins. *Organometallics* 2004, 23 (21), 5007-5020.
25. Foley, N. A.; Lail, M.; Gunnoe, T. B.; Cundari, T. R.; Boyle, P. D.; Petersen, J. L., Combined Experimental and Computational Study of TpRu{P(pyr)3}(NCMe)Me (pyr=N-pyrrolyl): Inter- and Intramolecular Activation of C—H Bonds and the Impact of Sterics on Catalytic Hydroarylation of Olefins. *Organometallics* 2007, 26 (23), 5507-5516.
26. Foley, N. A.; Lail, M.; Lee, J. P.; Gunnoe, T. B.; Cundari, T. R.; Petersen, J. L., Comparative reactivity of TpRu(L)(NCMe)Ph (L=CO or PMe3): impact of ancillary ligand 1 on activation of carbon-hydrogen bonds including catalytic hydroarylation and hydrovinylation/oligomerization of ethylene. *J. Am. Chem. Soc.* 2007, 129 (21), 6765-81.
27. McKeown, B. A.; Foley, N. A.; Lee, J. P.; Gunnoe, T. B., Hydroarylation of unactivated olefins catalyzed by platinum(II) complexes. *Organometallics* 2008, 27 (16), 4031-4033.
28. Foley, N. A.; Ke, Z.; Gunnoe, T. B.; Cundari, T. R.; Petersen, J. L., Aromatic C—H Activation and Catalytic Hydrophenylation of Ethylene by TpRu{P(OCH2)3CEt}(NCMe)Ph. *Organometallics* 2008, 27 (13), 3007-3017.
29. Foley, N. A.; Lee, J. P.; Ke, Z.; Gunnoe, T. B.; Cundari, T. R., Ru(II) catalysts supported by hydridotris(pyrazolyl)borate for the hydroarylation of olefins: reaction scope, mechanistic studies, and guides for the development of improved catalysts. *Acc. Chem. Res.* 2009, 42 (5), 585-97.
30. Andreatta, J. R.; McKeown, B. A.; Gunnoe, T. B., Transition metal catalyzed hydroarylation of olefins using unactivated substrates: Recent developments and challenges. *J. Organomet. Chem.* 2011, 696 (1), 305-315.
31. Joslin, E. E.; McMullin, C. L.; Gunnoe, T. B.; Cundari, T. R.; Sabat, M.; Myers, W. H., Catalytic Hydroarylation of Ethylene Using TpRu(L)(NCMe)Ph (L=2,6,7-Trioxa-1-phosphabicyclo[2,2,1]heptane): Comparison to TpRu (L')(NCMe)Ph Systems (L'=CO, PMe3, P(pyr)3, or P(OCH2)3CEt). *Organometallics* 2012, 31 (19), 6851-6860.
32. Burgess, S. A.; Joslin, E. E.; Gunnoe, T. B.; Cundari, T. R.; Sabat, M.; Myers, W. H., Hydrophenylation of ethylene using a cationic Ru(II) catalyst: comparison to a neutral Ru(II) catalyst. *Chem. Sci.* 2014, 5 (11), 4355-4366.
33. Jia, X. F.; Gary, J. B.; Gu, S. J.; Cundari, T. R.; Gunnoe, T. B., Oxidative Hydrophenylation of Ethylene Using a Cationic Ru(II) Catalyst: Styrene Production with Ethylene as the Oxidant. *Isr. J. Chem.* 2017, 57 (10-11), 1037-1046.
34. McKeown, B. A.; Gonzalez, H. E.; Friedfeld, M. R.; Gunnoe, T. B.; Cundari, T. R.; Sabat, M., Mechanistic studies of ethylene hydrophenylation catalyzed by bipyridyl Pt(II) complexes. *J. Am. Chem. Soc.* 2011, 133 (47), 19131-52.
35. McKeown, B. A.; Gonzalez, H. E.; Friedfeld, M. R.; Brosnahan, A. M.; Gunnoe, T. B.; Cundari, T. R.; Sabat, M., Platinum(II)-Catalyzed Ethylene Hydrophenylation: Switching Selectivity between Alkyl- and Vinylbenzene Production. *Organometallics* 2013, 32 (9), 2857-2865.
36. McKeown, B. A.; Gonzalez, H. E.; Gunnoe, T. B.; Cundari, T. R.; Sabat, M., PtII-Catalyzed Ethylene Hydrophenylation: Influence of Dipyridyl Chelate Ring Size on Catalyst Activity and Longevity. *ACS Catal.* 2013, 3 (6), 1165-1171.
37. McKeown, B. A.; Gonzalez, H. E.; Michaelos, T.; Gunnoe, T. B.; Cundari, T. R.; Crabtree, R. H.; Sabat, M., Control of Olefin Hydroarylation Catalysis via a Sterically and Electronically Flexible Platinum(II) Catalyst Scaffold. *Organometallics* 2013, 32 (14), 3903-3913.
38. Luedtke, A. T.; Goldberg, K. I., Intermolecular hydroarylation of unactivated olefins catalyzed by homogeneous platinum complexes. *Angew. Chem. Int. Ed. Engl.* 2008, 47 (40), 7694-6.
39. Clement, M. L.; Grice, K. A.; Luedtke, A. T.; Kaminsky, W.; Goldberg, K. I., Platinum(II) olefin hydroarylation catalysts: tuning selectivity for the anti-Markovnikov product. *Chem. Eur. J* 2014, 20 (52), 17287-91.
40. Suslick, B. A.; Liberman-Martin, A. L.; Wambach, T. C.; Tilley, T. D., Olefin Hydroarylation Catalyzed by (pyridyl-indolate)Pt(II) Complexes: Catalytic Efficiencies and Mechanistic Aspects. *ACS Catal.* 2017, 7 (7), 4313-4322.
41. Periana, R. A.; Liu, X. Y.; Bhalla, G., Novel bis-acac-O,O—Ir(III) catalyst for anti-Markovnikov, hydroarylation of olefins operates by arene CH activation. *Chem Commun (Camb)* 2002, (24), 3000-1.
42. Oxgaard, J.; Muller, R. P.; Goddard, W. A., 3rd; Periana, R. A., Mechanism of homogeneous Ir(III) catalyzed regioselective arylation of olefins. *J. Am. Chem. Soc.* 2004, 126 (1), 352-63.
43. Bhalla, G.; Oxgaard, J.; Goddard, W. A.; Periana, R. A., Anti-markovnikov hydroarylation of unactivated olefins catalyzed by a bis-tropolonato iridium(III) organometallic complex. *Organometallics* 2005, 24 (13), 3229-3232.
44. Ebe, Y.; Nishimura, T., Iridium-Catalyzed Branch-Selective Hydroarylation of Vinyl Ethers via C—H Bond Activation. *Journal of the American Chemical Society* 2015, 137 (18), 5899-5902.
45. Crisenza, G. E. M.; McCreanor, N. G.; Bower, J. F., Branch-Selective, Iridium-Catalyzed Hydroarylation of Monosubstituted Alkenes via a Cooperative Destabilization Strategy. *Journal of the American Chemical Society* 2014, 136 (29), 10258-10261.
46. Smidt, J.; Hafner, W.; Jira, R.; Sieber, R.; Sedlmeier, J.; Sabel, A., The Oxidation of Olefins with Palladium Chloride Catalysts. *Angewandte Chemie International Edition in English* 1962, 1 (2), 80-88.
47. Fujiwara, Y.; Moritani, I.; Danno, S.; Asano, R.; Teranishi, S., Aromatic substitution of olefins. VI. Arylation of olefins with palladium(II) acetate. *J. Am. Chem. Soc.* 1969, 91 (25), 7166-9.
48. Jia, X. F.; Foley, A. M.; Liu, C.; Vaughan, B. A.; McKeown, B. A.; Zhang, S.; Gunnoe, T. B., Styrene Production from Benzene and Ethylene Catalyzed by Palladium(II): Enhancement of Selectivity toward Styrene via Temperature-dependent Vinyl Ester Consumption. *Organometallics* 2019, 38 (19), 3532-3541.
49. Zhang, X.; Fan, S.; He, C. Y.; Wan, X.; Min, Q. Q.; Yang, J.; Jiang, Z. X., Pd(OAc)(2) catalyzed olefination of highly electron-deficient perfluoroarenes. *J. Am. Chem. Soc.* 2010, 132 (13), 4506-7.
50. Wang, P.; Verma, P.; Xia, G.; Shi, J.; Qiao, J. X.; Tao, S.; Cheng, P. T. W.; Poss, M. A.; Farmer, M. E.; Yeung, K.-S.;

Yu, J.-Q., Ligand-accelerated non-directed C—H functionalization of arenes. *Nature* 2017, 551 (7681), 489-493.

51. She, Z.; Shi, Y.; Huang, Y.; Cheng, Y.; Song, F.; You, J., Versatile palladium-catalyzed C—H olefination of (hetero)arenes at room temperature. *Chem. Commun.* 2014, 50 (90), 13914-13916.

52. Ying, C.-H.; Yan, S.-B.; Duan, W.-L., 2-Hydroxy-1,10-phenanthroline vs 1,10-Phenanthroline: Significant Ligand Acceleration Effects in the Palladium-Catalyzed Oxidative Heck Reaction of Arenes. *Org. Lett.* 2014, 16 (2), 500-503.

53. Zhu, W. H.; Luo, Z. W.; Chen, J. Q.; Liu, C.; Yang, L.; Dickie, D. A.; Liu, N. M.; Zhang, S.; Davis, R. J.; Gunnoe, T. B., Mechanistic Studies of Single-Step Styrene Production Catalyzed by Rh Complexes with Di-imine Ligands: An Evaluation of the Role of Ligands and Induction Period. *ACS Catal.* 2019, 9 (8), 7457-7475.

54. Chen, J.; Nielsen, R. J.; Goddard, W. A., 3rd; McKeown, B. A.; Dickie, D. A.; Gunnoe, T. B., Catalytic Synthesis of Superlinear Alkenyl Arenes Using a Rh(I) Catalyst Supported by a "Capping Arene" Ligand: Access to Aerobic Catalysis. *J. Am. Chem. Soc.* 2018, 140 (49), 17007-17018.

55. Vaughan, B. A.; Khani, S. K.; Gary, J. B.; Kammert, J. D.; Webster-Gardiner, M. S.; McKeown, B. A.; Davis, R. J.; Cundari, T. R.; Gunnoe, T. B., Mechanistic Studies of Single-Step Styrene Production Using a Rhodium(I) Catalyst. *J. Am. Chem. Soc.* 2017, 139 (4), 1485-1498.

56. Webster-Gardiner, M. S.; Chen, J.; Vaughan, B. A.; McKeown, B. A.; Schinski, W.; Gunnoe, T. B., Catalytic Synthesis of "Super" Linear Alkenyl Arenes Using an Easily Prepared Rh(I) Catalyst. *J. Am. Chem. Soc.* 2017, 139 (15), 5474-5480.

57. Vaughan, B. A.; Webster-Gardiner, M. S.; Cundari, T. R.; Gunnoe, T. B., Organic chemistry. A rhodium catalyst for single-step styrene production from benzene and ethylene. *Science* 2015, 348 (6233), 421-4.

58. Liebov, N. S.; Zhu, W. H.; Chen, F.; Webster-Gardiner, M. S.; Schinski, W. L.; Gunnoe, T. B., Rhodium-Catalyzed Alkenylation of Toluene Using 1-Pentene: Regioselectivity To Generate Precursors for Bicyclic Compounds. *Organometallics* 2019, 38 (19), 3860-3870.

59. Matsumoto, T.; Yoshida, H., Oxidative Arylation of Ethylene with Benzene to Produce Styrene. *Chem. Lett.* 2000, 29 (9), 1064-1065.

60. Matsumoto, T.; Periana, R. A.; Taube, D. J.; Yoshida, H., Direct synthesis of styrene by rhodium-catalyzed oxidative arylation of ethylene with benzene. *J. Catal.* 2002, 206 (2), 272-280.

61. Zhu, W.; Gunnoe, T. B., Advances in Rhodium-Catalyzed Oxidative Arene Alkenylation. *Acc. Chem. Res.* 2020, 53 (4), 920-936.

62. Gorelsky, S. I.; Lapointe, D.; Fagnou, K., Analysis of the concerted metalation-deprotonation mechanism in palladium-catalyzed direct arylation across a broad range of aromatic substrates. *J. Am. Chem. Soc.* 2008, 130 (33), 10848-9.

63. Potavathri, S.; Pereira, K. C.; Gorelsky, S. I.; Pike, A.; LeBris, A. P.; DeBoef, B., Regioselective oxidative arylation of indoles bearing N-alkyl protecting groups: dual C—H functionalization via a concerted metalation-deprotonation mechanism. *J. Am. Chem. Soc.* 2010, 132 (41), 14676-81.

64. Sun, H. Y.; Gorelsky, S. I.; Stuart, D. R.; Campeau, L. C.; Fagnou, K., Mechanistic analysis of azine N-oxide direct arylation: evidence for a critical role of acetate in the Pd(OAc)2 precatalyst. *J. Org. Chem.* 2010, 75 (23), 8180-9.

65. Walsh, A. P.; Jones, W. D., Mechanistic Insights of a Concerted Metalation-Deprotonation Reaction with [Cp*RhCl2]2. *Organometallics* 2015, 34 (13), 3400-3407.

66. Ackermann, L., Carboxylate-assisted transition-metal-catalyzed C—H bond functionalizations: mechanism and scope. *Chem. Rev.* 2011, 111 (3), 1315-45.

67. Dutta, U.; Maiti, S.; Pimparkar, S.; Maiti, S.; Gahan, L. R.; Krenske, E. H.; Lupton, D. W.; Maiti, D., Rhodium catalyzed template-assisted distal para-C—H olefination. *Chem. Sci.* 2019, 10 (31), 7426-7432.

68. Vora, H. U.; Silvestri, A. P.; Engelin, C. J.; Yu, J.-Q., Rhodium(II)-Catalyzed Nondirected Oxidative Alkenylation of Arenes: Arene Loading at One Equivalent. *Angew. Chem. Int. Ed.* 2014, 53 (10), 2683-2686.

69. Aggarwal, B. B.; Bhardwaj, A.; Aggarwal, R. S.; Seeram, N. P.; Shishodia, S.; Takada, Y., Role of resveratrol in prevention and therapy of cancer: preclinical and clinical studies. *Anticancer Res.* 2004, 24 (5A), 2783-2840.

70. Andrus, M. B.; Liu, J.; Meredith, E. L.; Nartey, E., Synthesis of resveratrol using a direct decarbonylative Heck approach from resorcylic acid. *Tetrahedron Lett.* 2003, 44 (26), 4819-4822.

71. Belleri, M.; Ribatti, D.; Nicoli, S.; Cotelli, F.; Forti, L.; Vannini, V.; Stivala, L. A.; Presta, M., Antiangiogenic and vascular-targeting activity of the microtubule-destabilizing trans-resveratrol derivative 3, 5, 4'-trimethoxystilbene. *Mol. Pharmacol.* 2005, 67 (5), 1451-1459.

72. Botella, L.; Najera, C., Synthesis of methylated resveratrol and analogues by Heck reactions in organic and aqueous solvents. *Tetrahedron* 2004, 60 (26), 5563-5570.

73. Delmas, D.; Lançon, A.; Colin, D.; Jannin, B.; Latruffe, N., Resveratrol as a chemopreventive agent: a promising molecule for fighting cancer. *Curr. Durg Targets* 2006, 7 (4), 423-442.

74. Han, G.; Xia, J.; Gao, J.; Inagaki, Y.; Tang, W.; Kokudo, N., Anti-tumor effects and cellular mechanisms of resveratrol. *Drug Discov. Ther.* 2015, 9 (1), 1-12.

75. Kuršvietienė, L.; Stanevičienė, I.; Mongirdienė, A.; Bernatonienė, J., Multiplicity of effects and health benefits of resveratrol. *Medicina* 2016, 52 (3), 148-155.

76. Li, H.-L.; Wang, A.-B.; Huang, Y.; Liu, D.-P.; Wei, C.; Williams, G. M.; Zhang, C.-N.; Liu, G.; Liu, Y.-Q.; Hao, D.-L., Isorhapontigenin, a new resveratrol analog, attenuates cardiac hypertrophy via blocking signaling transduction pathways. *Free Radical Biol. Med.* 2005, 38 (2), 243-257.

77. Martínez, A. V.; Garcia, J. I.; Mayoral, J. A., An expedient synthesis of resveratrol through a highly recoverable palladium catalyst. *Tetrahedron* 2017, 73 (38), 5581-5584.

78. Mei, Y.-Z.; Liu, R.-X.; Wang, D.-P.; Wang, X.; Dai, C.-C., Biocatalysis and biotransformation of resveratrol in microorganisms. *Biotechnol. Lett* 2015, 37 (1), 9-18.

79. Mikula-Pietrasik, J.; Sosińska, P.; Wierzchowski, M.; Piwocka, K.; Książek, K., Synthetic resveratrol analogue, 3,3',4,4',5,5'-hexahydroxy-trans-stilbene, accelerates senescence in peritoneal mesothelium and promotes senescence-dependent growth of gastrointestinal cancers. *Int. J. Mol. Sci.* 2013, 14 (11), 22483-22498.

80. Moro, A. V.; Cardoso, F. S. P.; Correia, C. R. D., Heck arylation of styrenes with arenediazonium salts: short, efficient, and stereoselective synthesis of resveratrol, DMU-212, and analogues. *Tetrahedron Lett.* 2008, 49 (39), 5668-5671.
81. Nam, K. A.; Kim, S.; Heo, Y. H.; Lee, S. K., Resveratrol analog, 3, 5, 2', 4'-tetramethoxy-trans-stilbene, potentiates the inhibition of cell growth and induces apoptosis in human cancer cells. *Arch. Pharmacal Res.* 2001, 24 (5), 441-445.
82. Nawaz, W.; Zhou, Z.; Deng, S.; Ma, X.; Ma, X.; Li, C.; Shu, X., Therapeutic versatility of resveratrol derivatives. *Nutrients* 2017, 9 (11), 1188.
83. Pervaiz, S.; Holme, A. L., Resveratrol: its biologic targets and functional activity. *Antioxid. Redox Sign.* 2009, 11 (11), 2851-2897.
84. Pezzuto, J. M., Resveratrol as an inhibitor of carcinogenesis. *Pharm. Biol.* 2008, 46 (7-8), 443-573.
85. Sale, S.; Tunstall, R. G.; Ruparelia, K. C.; Potter, G. A.; Steward, W. P.; Gescher, A. J., Comparison of the effects of the chemopreventive agent resveratrol and its synthetic analog trans 3,4,5,4'-tetramethoxystilbene (DMU-212) on adenoma development in the ApcMin+ mouse and cyclooxygenase-2 in human-derived colon cancer cells. *Int. J. Cancer* 2005, 115 (2), 194-201.
86. Ulrich, S.; Wolter, F.; Stein, J. M., Molecular mechanisms of the chemopreventive effects of resveratrol and its analogs in carcinogenesis. *Mol. Nutr. Food Res.* 2005, 49 (5), 452-461.
87. Yang, Y. T.; Weng, C. J.; Ho, C. T.; Yen, G. C., Resveratrol analog-3, 5, 4'-trimethoxy-trans-stilbene inhibits invasion of human lung adenocarcinoma cells by suppressing the MAPK pathway and decreasing matrix metalloproteinase-2 expression. *Mol. Nutr. Food Res.* 2009, 53 (3), 407-416.
88. Sinha, A. K.; Kumar, V.; Sharma, A.; Sharma, A.; Kumar, R., An unusual, mild and convenient one-pot two-step access to (E)-stilbenes from hydroxy-substituted benzaldehydes and phenylacetic acids under microwave activation: a new facet of the classical Perkin reaction. *Tetrahedron* 2007, 63 (45), 11070-11077.
89. Kumar, V.; Sharma, A.; Sharma, A.; Sinha, A. K., Remarkable synergism in methylimidazole-promoted decarboxylation of substituted cinnamic acid derivatives in basic water medium under microwave irradiation: a clean synthesis of hydroxylated (E)-stilbenes. *Tetrahedron* 2007, 63 (32), 7640-7646.
90. Yamada, Y. M.; Takeda, K.; Takahashi, H.; Ikegami, S., Assembled catalyst of palladium and non-cross-linked amphiphilic polymer ligand for the efficient heterogeneous Heck reaction. *Tetrahedron* 2004, 60 (18), 4097-4105.
91. Lo, C.; Cariou, R.; Fischmeister, C.; Dixneuf, P. H., Simple Ruthenium Precatalyst for the Synthesis of Stilbene Derivatives and Ring-Closing Metathesis in the Presence of Styrene Initiators. *Adv. Synth. Catal.* 2007, 349 (4-5), 546-550.
92. McNulty, J.; Das, P., Highly Stereoselective and General Synthesis of (E)-Stilbenes and Alkenes by Means of an Aqueous Wittig Reaction. *Eur. J. Org. Chem.* 2009, 2009 (24), 4031-4035.
93. Patureau, F. W.; Nimphius, C.; Glorius, F., Rh Catalyzed C—H Activation and Oxidative Olefination without Chelate Assistance: On the Reactivity of Bromoarenes. *Org. Lett.* 2011, 13 (24), 6346-6349.
94. Xie, L. H.; Suh, M. P., Flexible metal-organic framework with hydrophobic pores. *Chem. Eur. J* 2011, 17 (49), 13653-6.
95. Werner, H.; Poelsma, S.; Schneider, M. E.; Windmüller, B.; Barth, D., Synthesis and Reactivity of Bis(ethene) Rhodium(I) and Iridium(I) Carboxylato Complexes. *Chem. Ber.* 1996, 129 (6), 647-652.

Supplemental Information for Example 1

Unless otherwise noted, all synthetic procedures were performed under aerobic conditions. Glovebox purity was maintained by periodic nitrogen purges and was monitored by an oxygen analyzer ($O_2$<15 ppm for all reactions). Benzene was purified by passage through an column of activated alumina column. $^1$H NMR spectra were recorded on a Varian 600 spectrometer. $^1$H NMR spectra are referenced against residual proton signals ($^1$H NMR) of the deuterated solvents. GC/MS was performed using a Shimadzu GCMS-QP2010 Plus system with a 30 m×0.25 mm RTx-Qbond column with 8 µm thickness using electron impact ionization. GC/FID was performed using a Shimadzu GC-2014 system with a 30 m×90.25 mm HP5 column with 0.25 µm film thickness. For initial catalytic experiments without isolation of product, stilbene yields were quantified using linear regression analysis of gas chromatograms of standard samples of authentic product. The slope, correlation coefficient and the response factor of the regression line are 0.83, 0.99 and 0.80 for stilbene. Copper(II) pivalate and di-µ-acetatotetrakis(dihaptoethene)dirhodium(I) was synthesized according to a published procedure.[1, 2] All other reagents were used as received from commercial sources. High resolution mass spectrometry was performed at the University of Kansas Mass Spectrometry Lab.

Optimization of Reaction Condition

General procedure for Rh(I)-catalyzed oxidative hydrophenylation of styrene with benzene. Under an atmosphere of dry nitrogen, di-α-acetatotetrakis(dihaptoethene)dirhodium(I) (2.5 µmol, 550 µg), copper(II) pivalate (400 µmol, 106 mg), and pivalic acid (2 mmol, 204 mg) were added into a dried Andrews Glass™ Lab-Crest® Fisher-Porter tube with a stir bar. Styrene (500 µmol, 57 µL), and benzene (5 mL) were then added by syringe. The tube was opened to air, sealed and pressurized with dinitrogen (60 psig), and the mixture was stirred at 165° C. After 24 h, the reaction was allowed to cool to room temperature. The resultant mixture was diluted with ethyl acetate (40 mL), washed with saturated sodium carbonate solution (50 mL). The aqueous and organic layers were separated. The aqueous layer was extracted with ethyl acetate (3×40 mL), and the combined organic layers were washed with water (3×10 mL) and dried over magnesium sulfate. The resulting sample was subjected to GC-FID analysis. All yields and ratios given during the optimization studies were determined by GC-FID analysis of the crude reaction mixture using hexamethylbenzene as an internal standard.

TABLE SI

Solvent screening for stilbene production.

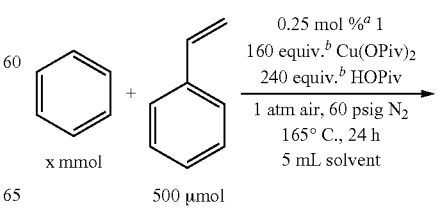

TABLE S1-continued

[Structure: stilbene (trans-1,2-diphenylethylene)]

| entry | solvent | benzene loading x | yield[c] (%) |
|---|---|---|---|
| 1 | DMF | 3 | 0 |
| 2 | MeOH | 3 | 0.2 |
| 3 | 1,4-dioxane | 3 | 3 |
| 4 | hexane | 3 | 7 |
| 5 | mesitylene | 3 | 10.9 |
| 6 | mesitylene | 5 | 17.4 |
| 7 | hexafluorobenzene | 3 | 12.1 |
| 8 | hexafluorobenzene | 5 | 21.7 |
| 9 | acetic acid | 3 | 2.6 |
| 10 | benzene | / | 81 |

[a]0.25 mol% [Rh(μ-OAc)(η$^2$-C$_2$H$_4$)$_2$]$_2$ (1) (0.5 mol% based on rhodium).
[b]Amounts of Cu(II) pivalate and pivalic acid are relative to Rh.
[c]GC yield based on calibration curve using hexamethylbenzene as internal standard.

TABLE S2

Comparison of air and dioxygen for stilbene production.

[Reaction scheme: benzene (5 mL) + styrene (500 μmol) → stilbene, with 0.25 mol%[a] 1, 160 equiv.[b] Cu(OPiv)$_2$, 240 equiv.[b] HOPiv, oxygen source, 60 psig N$_2$, 165° C., 54 h]

| entry | oxygen source | yield[c] |
|---|---|---|
| 1 | Air | 81 |
| 2 | Oxygen[d] | 82 |

[a]0.25 mol% [Rh(μ-OAc)(η$^2$-C$_2$H$_4$)$_2$]$_2$ (1) (0.5 mol% based on rhodium).
[b]Amounts of Cu(II) pivalate and pivalic acid are relative to Rh.
[c]GC yield based on calibration curve using hexamethylbenzene as internal standard.
[d]Pure oxygen was purged through the reaction mixture for one minute.

TABLE S3

Comparison of Cu(II) pivalate amount for stilbene production.

[Reaction scheme: benzene (5 mL) + styrene (500 μmol) → with 0.25 mol%[a] 1, x equiv.[b] Cu(OPiv)$_2$, 240 equiv.[b] HOPiv, 1 atm air, 60 psig N$_2$, 165° C., 54 h]

TABLE S3-continued

[Structure: stilbene]

| entry | x | yield[c] |
|---|---|---|
| 1 | 0 | 0 |
| 2 | 20 | 52 |
| 3 | 160 | 81 |
| 4 | 320[d] | 71 |

[a]0.25 mol% [Rh(μ-OAc)(η$^2$-C$_2$H$_4$)$_2$]$_2$ (1) (0.5 mol% based on rhodium).
[b]Amounts of Cu(II) pivalate and pivalic acid are relative to Rh.
[c]GC yield based on calibration curve using hexamethylbenzene as internal standard.
[d]This copper loading is beyond the copper salt's maximum solubility at room temperature.

TABLE S4

Temperature and concentration of pivalate acid.

[Reaction scheme: benzene (5 mL) + styrene (500 μmol) → with 0.25 mol%[a] 1, 160 equiv.[b] Cu(OPiv)$_2$, 1 atm air, 60 psig N$_2$, HOPiv, temp, 24 h]

[Structure: stilbene]

| entry | HOPiv (equiv.[b]) | temp (° C.) | yield[c] |
|---|---|---|---|
| 1 | 240 | 150 | 71 |
| 2 | 240 | 165 | 81 |
| 3 | 800 | 165 | 92 |
| 4 | 1600 | 165 | 20 |

[a]0.25 mol% [Rh(μ-OAc)(η$^2$-C$_2$H$_4$)$_2$]$_2$ (1) (0.5 mol% based on rhodium).
[b]Amounts of Cu(II) pivalate and pivalic acid are relative to Rh.
[c]GC yield based on a calibration curve using hexamethylbenzene as internal standard.

TABLE S5

Comparison of additives to remove water for stilbene production.

[Reaction scheme: benzene (5 mL) + styrene (500 μmol) → with 0.25 mol%[a] 1, 160 equiv.[b] Cu(OPiv)$_2$, 800 equiv.[b] HOPiv, 1 atm air, 60 psig N$_2$, 165° C., 24 h, additives]

[Structure: stilbene]

TABLE S5-continued

| entry | additives | yield[c] (%) |
|---|---|---|
| 1 | 4A molecular sieve | 91 |
| 2 | 3A molecular sieve | 72 |
| 3 | $V_2O_5$ | 90 |
| 4 | Graphene Oxide[d] | 91 |
| 5 | $Ac_2O$[e] | 5.1 |
| 6 | / | 92 |

[a]0.25 mol% [Rh(μ-OAc)(η$^2$-C$_2$H$_4$)$_2$]$_2$ (1) (0.5 mol% based on rhodium).
[b]Amounts of Cu(II) pivalate and pivalic acid are relative to Rh.
[c]GC yield based on calibration curve using hexamethylbenzene as internal standard
[d]Graphene oxide was synthesized by a modified Hummer method
[e]5 mL of Ac$_2$O (acetic anhydride) was added.

TABLE S6

Optimization of the reaction condition using 1,3-dimethoxy benzene as arene substrate.

| entry | temp (° C.) | time[c] (h) | yield[d] (%) |
|---|---|---|---|
| 1 | 165 | 24 | 31 |
| 2 | 150 | 24 | 41 |
| 3 | 150 | 48 | 47 |
| 4 | 135 | 24 | 17 |
| 5 | 135 | 48 | 37 |
| 6 | 135 | 72 | 52 |
| 7 | 135 | 96 | 71 |
| 8 | 135 | 108 | 71 |

[a]0.25 mol% [Rh(μ-OAc)(η$^2$-C$_2$H$_4$)$_2$]$_2$ (1) (0.5 mol% based on rhodium).
[b]Amounts of Cu(II) pivalate and pivalic acid are relative to Rh.
[c]Reactors were cooled down and purged with air every 24 hours
[d]Yield is GC yield based on calibration curve using hexamethylbenzene as internal standard Scope of Vinyl Arenes
General Procedure for Rh(I)-Catalyzed Oxidative Hydrophenylation of Vinyl Arenes with Benzene.

Under an atmosphere of dry nitrogen, di-μ-acetatotetrakis(dihaptoethene)dirhodium(I) (1) (2.5 μmol, 550 μg), copper (II) pivalate (400 μmol, 106 mg), and pivalic acid (2 mmol, 204 mg) were added into a dried Andrews Glass™ Lab-Crest® Fisher-Porter tube with a stir bar. Then vinyl arene (500 μmol) and benzene (5 mL) were added by syringe. Then the tube was opened to air, sealed and pressurized with dinitrogen (60 psig). The mixture was stirred at 165° C. After 24 h, the reaction was allowed to cool to room temperature. The resultant mixture was diluted with ethyl acetate (40 mL) and washed with saturated sodium carbonate solution (50 mL). The aqueous and organic layers were separated. The aqueous layer was extracted with ethyl acetate (3×40 mL) and the combined organic layers were washed with water, (3×10 mL), dried over magnesium sulfate, filtered, and concentrated under vacuum.

Alkenylation of Benzene Using Styrene (E)-Stilbene (2a)

Following the general procedure described above and using styrene as the vinyl arene, the target compound 2a was obtained as a white solid (83 mg, 92%). The product was purified by flash column chromatography using hexanes as the eluent. This compound was reported in literature.[3] $^1$H NMR (600 MHz, CDCl$_3$): δ 7.53 (d, J=7.3 Hz, 4H), 7.37 (t, J=7.7 Hz, 4H), 7.27 (t, J=7.4 Hz, 2H), 7.12 (s, 2H) ppm. $^{13}$C NMR (201 MHz, CDCl$_3$): δ 137.5, 128.8, 127.8, 126.7 ppm. HRMS (HAPCI) m/z: Calcd for=C$_{14}$H$_{12}$$^+$=180.0939, Found=180.0935.

Alkenylation of Benzene Using 4-methylstyrene (E)-4-methyl-1-styrylbenzene (2b)

Following the general procedure described above and using 4-methylstyrene as the vinyl arene, the target compound 2b was obtained as a white solid (84 mg, 87%). The product was purified by flash column chromatography using hexanes as the eluent. This compound was reported in literature.[4] $^1$H NMR (600 MHz, CDCl$_3$): δ 7.53 (m, 2H), 7.45 (m, 2H), 7.38 (m, 2H), 7.28 (m, 1H), 7.20 (m, 2H), 7.13 (d, J=16.4 Hz, 1H), 7.09 (d, J=16.4 Hz, 1H), 2.39 (s, 3H) ppm. $^{13}$C NMR (201 MHz, CDCl$_3$): δ 137.7, 134.7, 129.53, 128.8, 128.8, 128.7, 127.8, 127.5, 126.5, 21.4, 21.4 ppm. HRMS (HAPCI) m/z: Calcd for C$_{15}$H$_{14}$$^+$=194.1096, Found Mass=194.1098.

Alkenylation of Benzene Using 3-methylstyrene (E)-3-methyl-1-styrylbenzene (2c)

Following the general procedure described above and using 4-methylstyrene as the vinyl arene, the target compound 2c was obtained as a white solid (80 mg, 82%). The product was purified by flash column chromatography using hexanes as the eluent. This compound was reported in literature.[4] $^{1}$H NMR (600 MHz, CDCl$_3$): δ 7.54 (m, 2H), 7.41-7.33 (m, 4H), 7.31-7.26 (m, 2H), 7.16-7.08 (m, 3H), 2.41 (s, 3H) ppm. $^{13}$C NMR (201 MHz, CDCl$_3$): δ 138.4, 137.6, 137.4, 129.0, 128.8, 128.7, 128.7, 128.6, 128.6, 128.6, 127.7, 127.4, 126.6, 123.9, 21.6 ppm. HRMS (HAPCI) m/z: Calcd for C$_{15}$H$_{14}$$^+$=194.1096, Found Mass=194.1083.

Alkenylation of Benzene Using 2,4,6-trimethylstyrene (E)-2,4,6-trimethyl-1-styrylbenzene (2d)

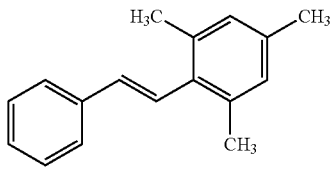 [SMILES: Cc1cc(C)c(/C=C/c2ccccc2)c(C)c1]

Following the general procedure described above and using 2,4,6-trimethylstyrene as the vinyl arene, the target compound 2d was obtained as a white solid (52 mg, 47%) after 48 hours reaction. The product was purified by flash column chromatography using hexanes as the eluent. This compound was reported in literature.[5] 1H NMR (600 MHz, CDCl$_3$): δ 7.47 (m, 2H), 7.41 (dd, J=1.9, 0.6 Hz, 1H), 7.35 (m, 2H), 7.25 (m, 1H), 7.05 (d, J=16.3 Hz, 1H), 6.91 (d, J=16.2 Hz, 1H), 6.43 (dd, J=3.3, 1.8 Hz, 1H), 6.36 (dd, J=3.3, 0.4 Hz, 1H) ppm. $^{13}$C NMR (151 MHz, CDCl$_3$): δ 153.4, 142.3, 137.2, 128.8, 127.7, 127.3, 126.5, 116.7, 111.8, 108.7 ppm. HRMS (HAPCI) m/z: Calcd for C$_{17}$H$_{19}$$^+$=223.1487, Found Mass=223.1486.

Alkenylation of Benzene Using 2-vinylnaphthalene (E)-2-styrylnaphthalene (2e)

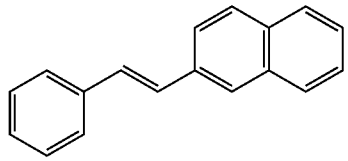 [SMILES: C(=C\c1ccc2ccccc2c1)/c1ccccc1]

Following the general procedure described above and using 2-vinylnaphthalene as the vinyl arene, the target compound 2e was obtained as a white solid (88 mg, 77%). The product was purified by flash column chromatography using hexanes as the eluent. This compound was reported in literature.[6] $^{1}$H NMR (600 MHz, CDCl$_3$): δ 7.86 (br, s, 1H), 7.85-7.79 (m, 3H), 7.75 (dd, J=8.6, 1.8 Hz, 1H), 7.57 (m, 2H), 7.50-7.42 (m, 2H), 7.38 (m, 2H), 7.29 (d, J=16.4 Hz, 2H), 7.28 (m, 2H), 7.24 (d, J=16.3 Hz, 1H) ppm. $^{13}$C NMR (151 MHz, CDCl$_3$): δ 137.5, 135.0, 133.9, 133.2, 129.2, 128.9, 128.9, 128.5, 128.1, 127.8, 127.8, 126.8, 126.7, 126.5, 126.0, 123.7 ppm. HRMS (HAPCI) m/z: Calcd for C$_{18}$H$_{15}$$^+$=231.1174, Found Mass=231.1169.

Alkenylation of Benzene Using 4-fluorostyrene (E)-4-fluoro-1-styrylbenzene (2f)

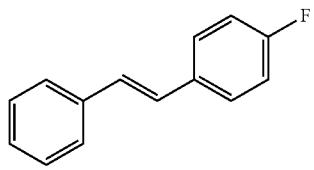 [SMILES: Fc1ccc(/C=C/c2ccccc2)cc1]

Following the general procedure described above and using 4-fluorostyrene as the vinyl arene, the target compound 2f was obtained as a white solid (64 mg, 64%). The product was purified by flash column chromatography using hexanes as the eluent. This compound was reported in literature.[4] $^{1}$H NMR (600 MHz, CDCl$_3$): δ 7.49 (m, 4H), 7.36 (t, J=7.6 Hz, 2H), 7.28 (s, 1H), 7.09-7.00 (m, 4H) ppm. $^{13}$C NMR (201 MHz, CDCl$_3$): δ 162.3 (d, J=247.3 Hz), 137.2, 133.5 (d, J=3.3 Hz), 128.70, 128.5 (d, J=2.3 Hz), 128.0 (d, J=7.9 Hz), 127.7, 127.5, 126.4, 115.6 (d, J=21.6 Hz) ppm. $^{19}$F NMR (564 MHz, CDCl$_3$): δ −112.5 (tt, J=8.6, 5.4 Hz) ppm. HRMS (HAPCI) m/z: Calcd for C$_{14}$H$_{11}$F$^+$=198.0845, Found Mass=198.0839.

Alkenylation of Benzene of 3-fluorostyrene (E)-3-fluoro-1-styrylbenzene (2g)

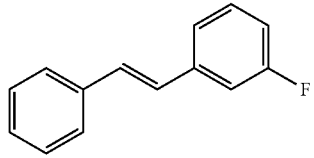 [SMILES: Fc1cccc(/C=C/c2ccccc2)c1]

Following the general procedure described above and using 3-fluorostyrene as the vinyl arene, the target compound 2g was obtained as a white solid (65 mg, 64%). The product was purified by flash column chromatography using hexanes as the eluent. This compound was reported in literature.[6] $^{1}$H NMR (600 MHz, CDCl$_3$): δ 7.52 (d, J=7.7 Hz, 2H), 7.37 (t, J=7.6 Hz, 2H), 7.33-7.27 (m, 3H), 7.22 (d, J=10.0 Hz, 1H), 7.11, 7.07 (ABq, Δv$_{AB}$=24 Hz, J$_{AB}$=18 Hz, 2H), 6.95 (t, J=7.8 Hz, 1H) ppm. $^{13}$C NMR (201 MHz, CDCl$_3$): δ 163.3 (d), 139.9 (d), 137.0, 130.2 (d), 130.2, 128.9, 128.2, 127.6 (d), 126.8, 122.6 (d), 114.5 (d), 112.9 (d) ppm. $^{19}$F NMR (564 MHz, CDCl$_3$): δ −111.8 (td, J=9.3, 6.2 Hz, 1F) ppm. HRMS (HAPCI) m/z: Calcd for C$_{14}$H$_{11}$F$^+$=198.0845, Found Mass=198.0836.

Alkenylation of Benzene Using 2-fluorostyrene (E)-2-fluoro-1-styrylbenzene (2h)

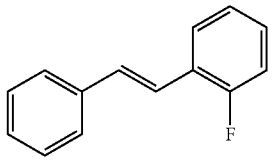 [SMILES: Fc1ccccc1/C=C/c1ccccc1]

Following the general procedure described above and using 2-fluorostyrene as the vinyl arene, the target compound 2h was obtained as a white solid (87 mg, 88%). The product was purified by flash column chromatography using hexanes as the eluent. This compound was reported in literature.[7] $^1$H NMR (600 MHz, CDCl$_3$): δ 7.63 (td, J=7.7, 1.8 Hz, 1H), 7.56 (m, 2H), 7.39 (m, 2H), 7.33-7.28 (m, 2H), 7.27-7.23 (m, 1H), 7.21 (d, J=16.5 Hz, 1H), 7.16 (td, J=7.5, 1.3 Hz, 1H), 7.10 (ddd, J=10.8, 8.2, 1.3 Hz, 1H) ppm. $^{13}$C NMR (201 MHz, CDCl$_3$): δ 159.8 (d, J=249.3 Hz), 137.4, 131.1 (d, J=4.9 Hz), 128.9 (d, J=8.5 Hz), 128.9, 128.1, 127.2 (d, J=3.9 Hz), 126.8, 125.4 (d, J=11.6 Hz), 124.3 (d, J=3.4 Hz), 121.1 (d, J=3.5 Hz), 115.9 (d, J=22.0 Hz) ppm. $^{19}$F NMR (564 MHz, CDCl$_3$): δ −116.3 (ddd, J=11.0, 7.6, 5.1 Hz, 1F) ppm. HRMS (HAPCI) m/z: Calcd for C$_{14}$H$_{11}$F$^+$=198.0845, Found Mass=198.0844.

Alkenylation of Benzene Using 4-chlorostyrene (E)-4-chloro-1-styrylbenzene (2i)

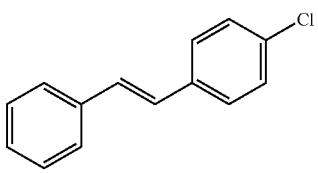 [SMILES: Clc1ccc(/C=C/c2ccccc2)cc1]

Following the general procedure described above and using 4-chlorostyrene as the vinyl arene, the target compound 2i was obtained as a white solid (79 mg, 74%). The product was purified by flash column chromatography using hexanes as the eluent. This compound was reported in literature.[4] $^1$H NMR (600 MHz, CDCl$_3$): δ 7.51 (d, J=7.6 Hz, 2H), 7.44 (d, J=8.6 Hz, 2H), 7.37 (t, J=7.7 Hz, 2H), 7.33 (d, J=8.5 Hz, 2H), 7.28 (t, J=7.3 Hz, 1H), 7.08, 7.05 (ABq, Δν$_{AB}$=13.4 Hz, J$_{AB}$=12 Hz, 2H) ppm. $^{13}$C NMR (201 MHz, CDCl$_3$): δ 137.1, 136.0, 133.3, 129.5, 129.0, 128.9, 128.0, 127.8, 127.5, 126.7 ppm. HRMS (HAPCI) m/z: Calcd for C$_{14}$H$_{11}$Cl$^+$=214.0549, Found Mass=214.0558.

Alkenylation of Benzene Using 4-bromostyrene (E)-4-bromo-1-styrylbenzene (2j)

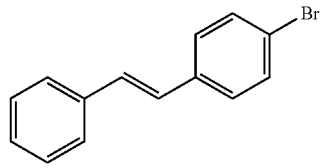 [SMILES: Brc1ccc(/C=C/c2ccccc2)cc1]

Following the general procedure described above and using 4-bromostyrene as the vinyl arene, the target compound 2j was obtained as a white solid (87 mg, 68%). The product was purified by flash column chromatography using hexanes as the eluent. This compound was reported in literature.[4] $^1$H NMR (600 MHz, CDCl$_3$): δ 7.56-7.46 (m, 4H), 7.41-7.33 (m, 4H), 7.28 (m, 1H), 7.10 (d, J=16.3 Hz, 1H), 7.04 (d, J=16.3 Hz, 1H) ppm. $^{13}$C NMR (201 MHz, CDCl$_3$): δ 137.1, 136.4, 131.9, 129.6, 128.9, 128.12, 128.05, 127.6, 126.7, 121.5 ppm.

Alkenylation of Benzene Using 4-iodostyrene (E)-4-iodo-1-styrylbenzene (2k)

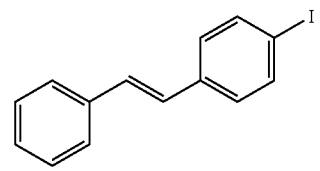 [SMILES: Ic1ccc(/C=C/c2ccccc2)cc1]

Following the general procedure described above and using 4-iodostyrene as the vinyl arene, the target compound 2k was obtained as a white solid (104 mg, 68%). The product was purified by flash column chromatography using hexanes as the eluent. This compound was reported in literature.[3] $^1$H NMR (600 MHz, CDCl$_3$): δ 7.68 (m, 1H), 7.51 (m, 1H), 7.36 (m, 2H), 7.28 (m, 1H), 7.25 (m, 2H), 7.11 (d, J=16.3 Hz, 1H), 7.02 (d, J=16.3 Hz, 1H) ppm. $^{13}$C NMR (151 MHz, CDCl$_3$): δ 137.9, 137.1, 137.0, 129.7, 128.9, 128.4, 128.1, 127.6, 126.7, 92.9 ppm.

Alkenylation of Benzene Using 4-vinylphenylacetate (E)-4-styrylphenylacetate (2l)

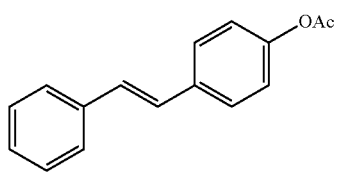 [SMILES: CC(=O)Oc1ccc(/C=C/c2ccccc2)cc1]

Following the general procedure described above and using 4-chlorostyrene as the vinyl arene, the target compound 2i was obtained as a white solid (105 mg, 88%). The product was purified by flash column chromatography using hexanes and ethyl acetate (v/v=95:5) as the eluent. This compound was reported in literature.[3] $^1$H NMR (600 MHz, CDCl$_3$): δ 7.52 (m, 4H), 7.37 (m, 2H), 7.27 (m, 2H), 7.10 (m, 3H), 7.06 (d, J=16.4 Hz, 1H), 2.31 (s, 3H) ppm. $^{13}$C NMR (151 MHz, CDCl$_3$): δ 169.60, 150.20, 137.31, 135.30, 129.10, 128.84, 127.85, 127.80, 127.56, 126.65, 121.94, 21.30 ppm.

Alkenylation of Benzene Using 4-nitrostyrene (E)-4-styryl-nitrobenzene (2m)

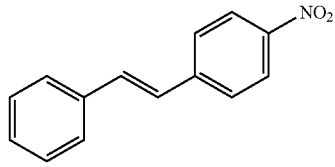 [SMILES: O=[N+]([O-])c1ccc(/C=C/c2ccccc2)cc1]

Following the general procedure described above and using 4-nitrostyrene as the vinyl arene, the target compound 2m was obtained as a yellow solid (82 mg, 73%). The product was purified by flash column chromatography using hexanes as the eluent. This compound was reported in literature.[8] $^1$H NMR (600 MHz, CDCl$_3$): δ 8.22 (td, J=8.8, 2.5 Hz, 2H), 7.63 (td, J=8.5, 2.3 Hz, 2H), 7.56 (m, 2H), 7.41 (m, 2H), 7.34 (m, 1H), 7.30-7.25 (m, 1H), 7.15 (d, J=16.3 Hz, 1H) ppm. $^{13}$C NMR (151 MHz, CDCl$_3$): δ 146.9, 144.0, 136.3, 133.5, 129.0, 129.0, 127.2, 127.0, 126.4, 124.3 ppm. HRMS (HAPCI) m/z: Calcd for C$_{14}$H$_{12}$NO$_2$$^+$=226.0868, Found Mass=226.0861.

Alkenylation of Benzene Using 4-vinylbenzonitrile (E)-4-styrylbenzonitrile (2n)

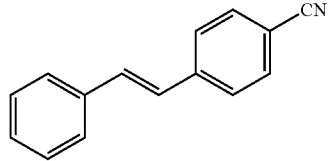 [SMILES: N#Cc1ccc(/C=C/c2ccccc2)cc1]

Following the general procedure described above and using 4-vinylbenzonitrile as the vinyl arene, the target compound 2n was obtained as a white solid (85 mg, 66%). The product was purified by flash column chromatography using hexanes and ethyl acetate (v/v=85:15) as the eluent. This compound was reported in literature.[9] $^1$H NMR (600 MHz, CDCl$_3$): δ 7.64 (m, 2H), 7.58 (m, 2H), 7.54 (m, 2H), 7.40 (m, 2H), 7.33 (m, 1H), 7.22 (d, J=16.2 Hz, 1H), 7.09 (d, J=16.3 Hz, 1H) ppm. $^{13}$C NMR (151 MHz, CDCl$_3$): δ 142.0, 136.4, 132.6, 132.5, 129.0, 128.8, 127.0, 127.0, 126.9, 119.2, 110.7 ppm. HRMS (HAPCI) m/z: Calcd for C$_{15}$H$_{11}$N$^+$=205.0891, Found Mass=205.0898.

Alkenylation of Benzene Using 4-methoxystyrene (E)-4-styrylanisole (2o)

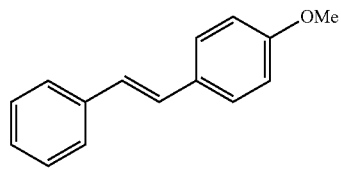 [SMILES: COc1ccc(/C=C/c2ccccc2)cc1]

Following the general procedure described above and using 4-vinylanisole as the vinyl arene, the target compound 2o was obtained as a white solid (91 mg, 87%). The product was purified by flash column chromatography using hexanes and ethyl acetate (v/v=9:1) as the eluent. This compound was reported in literature.[4] $^1$H NMR (600 MHz, CDCl$_3$): δ 7.48 (dd, J=20.1, 8.0 Hz, 4H), 7.35 (t, J=7.5 Hz, 2H), 7.24 (t, J=7.4 Hz, 1H), 7.07, 6.98 (ABq, Δv$_{AB}$=52.6 Hz, J$_{AB}$=16.3 Hz, 2H), 6.91 (d, J=8.4 Hz, 2H), 3.84 (s, 3H) ppm. $^{13}$C NMR (201 MHz, CDCl$_3$): δ 159.4, 137.8, 130.3, 128.8, 128.4, 127.9, 127.4, 126.8, 126.4, 114.3, 77.2, 55.5 ppm. HRMS (HAPCI) m/z: Calcd for C$_{15}$H$_{15}$O$^+$=211.1123, Found Mass=211.1116.

Alkenylation of Benzene Using 3-methoxystyrene (E)-3-styrylanisole (2p)

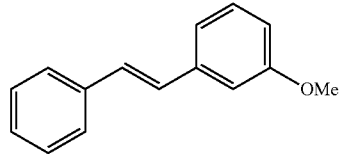 [SMILES: COc1cccc(/C=C/c2ccccc2)c1]

Following the general procedure described above and using 3-vinylanisole as the vinyl arene, the target compound 2p was obtained as a white solid (87 mg, 83%). The product was purified by flash column chromatography using hexanes and ethyl acetate (v/v=9:1) as the eluent. This compound was reported in literature.[6] $^1$H NMR (600 MHz, CDCl$_3$): δ 7.55 (m, 2H), 7.40 (m, 2H), 7.35-7.28 (m, 2H), 7.19-7.12 (m, 3H), 7.10 (dd, J=2.6, 1.0 Hz, 1H), 6.87 (ddd, J=8.2, 2.5, 0.9 Hz, 1H), 3.88 (s, 3H) ppm. $^{13}$C NMR (151 MHz, CDCl$_3$): δ 160.0, 138.9, 137.4, 129.8, 129.1, 128.8, 128.7, 127.8, 126.7, 119.4, 113.4, 111.9, 55.3 ppm. HRMS (HAPCI) m/z: Calcd for C$_5$H$_{15}$O$^+$=211.1123, Found Mass=211.1128.

Alkenylation of Benzene Using 2-methoxystyrene (E)-3-styrylanisole (2q)

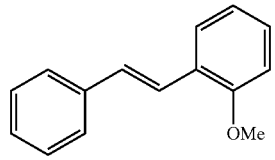 [SMILES: COc1ccccc1/C=C/c1ccccc1]

Following the general procedure described above and using 2-vinylanisole as the vinyl arene, the target compound 2q was obtained as a white solid (83 mg, 79%). The product was purified by flash column chromatography using hexanes and ethyl acetate (v/v=9:1) as the eluent. This compound was reported in literature.[10] $^1$H NMR (600 MHz, CDCl$_3$): δ 7.63 (dd, J=7.7, 1.7 Hz, 1H), 7.57 (m, 2H), 7.53 (d, J=16.4 Hz, 1H), 7.38 (m, 2H), 7.30-7.25 (m, 2H), 7.15 (d, J=16.5 Hz, 1H), 7.00 (m, 1H), 6.92 (m, 1H), 3.91 (s, 3H) ppm. $^{13}$C NMR (151 MHz, CDCl$_3$): δ 157.0, 138.1, 129.2, 128.8, 128.7, 127.5, 126.7, 126.6, 126.5, 123.6, 120.9, 111.0, 55.6 ppm. HRMS (HAPCI) m/z: Calcd for $C_{15}H_{15}O^+$=211.1123, Found Mass=211.1116.

Alkenylation of Benzene Using 3,5-dimethoxystyrene (E)-3,5-dimethoxyl-1-styrlbenzene (2r)

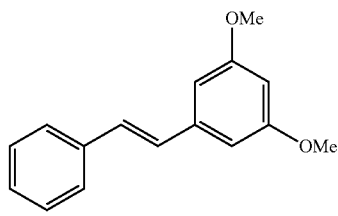 [SMILES: COc1cc(/C=C/c2ccccc2)cc(OC)c1]

Following the general procedure described above and using 3,5-dimethoxybenzene as the vinyl arene, the target compound 2r was obtained as a colorless liquid (95 mg, 84%). The product was purified by flash column chromatography using hexanes and ethyl acetate (v/v=9:1) as the eluent. This compound was reported in literature.[6] $^1$H NMR (600 MHz, CDCl$_3$): δ 7.52 (m, 2H), 7.37 (m, 2H), 7.28 (m, 1H), 7.11 (d, J=16.3 Hz, 1H), 7.05 (d, J=16.3 Hz, 1H), 6.70 (d, J=2.3 Hz, 2H), 6.42 (t, J=2.3 Hz, 1H), 3.85 (s, 6H) ppm. $^{13}$C NMR (151 MHz, CDCl$_3$): δ 161.1, 139.5, 137.3, 129.3, 128.8, 127.9, 126.7, 104.7, 100.1, 55.5 ppm. HRMS (HAPCI) m/z: Calcd for $C_{16}H_{17}O_2^+$=241.1229, Found Mass=241.1221.

Alkenylation of Benzene Using 3,5-dimethoxystyrene (E)-3,4-dimethoxyl-1-styrylbenzene (2s)

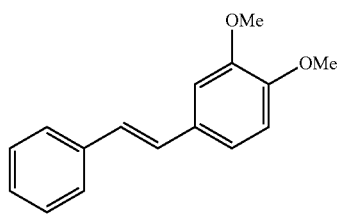 [SMILES: COc1ccc(/C=C/c2ccccc2)cc1OC]

Following the general procedure described above and using 3,4-dimethoxybenzene as the vinyl arene, the target compound 2s was obtained as a colorless liquid (92 mg, 82%). The product was purified by flash column chromatography using hexanes and ethyl acetate (v/v=9:1) as the eluent. This compound was reported in literature.[4] $^1$H NMR (600 MHz, CDCl$_3$): δ 7.50 (m, 2H), 7.35 (m, 2H), 7.25 (m, 1H), 7.09-7.03 (m, 3H), 6.98 (d, J=16.3 Hz, 1H), 6.87 (d, J=8.2 Hz, 1H), 3.95 (s, 3H), 3.91 (s, 3H) ppm. $^{13}$C NMR (151 MHz, CDCl$_3$): δ 149.3, 149.1, 137.7, 130.6, 128.8, 128.6, 127.4, 127.0, 126.4, 120.0, 111.4, 108.9, 56.1, 56.0 ppm. HRMS (HAPCI) m/z: Calcd for $C_{16}H_{16}O_2^+$=240.1150, Found Mass=240.1144.

Alkenylation of Benzene Using α-methylstyrene (E)-α-methyl stilbene (2t) and 2,3-diphenylpropene (2u)

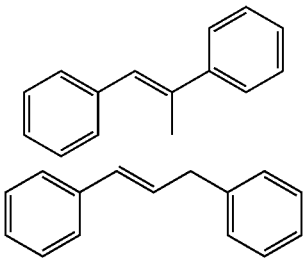

Following the general procedure described above and using α-methylstyrene as the vinyl arene, the target compound 2t and 2u were obtained as a white solid (72 mg, 74%, 2t:2u=43:31). The products were separated and purified by flash column chromatography using hexanes as the eluent. Both compounds were reported in literature.[11]

Characterizations for 2t: $^1$H NMR (600 MHz, CDCl$_3$): δ 7.54 (m, 2H), 7.42-7.35 (m, 6H), 7.30 (m, 1H), 7.28-7.22 (m, 1H), 6.85 (q, J=1.4 Hz, 1H), 2.30 (d, J=1.4 Hz, 3H) ppm. $^{13}$C NMR (151 MHz, CDCl$_3$): δ 144.12, 138.51, 137.57, 129.29, 128.47, 128.32, 127.85, 127.33, 126.61, 126.15, 17.63 ppm.

Characterizations for 2u: $^1$H NMR (600 MHz, CDCl$_3$): δ 7.44 (m, 2H), 7.32-7.27 (m, 4H), 7.25-7.21 (m, 3H), 7.19 (m, 1H), 5.50 (d, J=1.3 Hz, 1H), 5.02 (q, J=1.3 Hz, 1H), 3.84 (d, J=1.3 Hz, 2H) ppm.

HRMS (HAPCI) m/z: Calcd for $C_{15}H_{14}^+$=194.1096, Found Mass=194.1093.

Alkenylation of Benzene Using β-transmethylstyrene (E)-α-methyl stilbene (2t) and (E)-1,3-diphenylpropene (2v)

Following the general procedure described above and using b-methylstyrene as the vinyl arene, the target compound 2u and 2v were obtained as a white solid (72 mg, 74%, 2u:2w=39:29). The products were separated and purified by flash column chromatography using hexanes as the eluent. Both compounds were reported in literature.[11, 12]

Characterizations for 1v: $^1$H NMR (600 MHz, CDCl$_3$): δ 7.37 (m, 2H), 7.34-7.27 (m, 4H), 7.27-7.23 (m, 2H), 7.23-7.18 (m, 2H), 6.47 (dt, J=15.9, 1.5 Hz, 1H), 6.37 (dt, J=15.7, 6.8 Hz, 1H), 3.58-3.54 (m, 2H) ppm.

HRMS (HAPCI) m/z: Calcd for $C_{15}H_{14}^+$=194.1096, Found Mass=194.1098.

Scope of Arenes

General procedure for Rh(I)-catalyzed oxidative hydroarylation of styrene with arenes. Under an atmosphere of dry nitrogen, di-μ-acetatotetrakis(dihaptoethene)dirhodium(I) (1) (2.5 mol, 550 μg), copper(II) pivalate (400 μmol, 106 mg) and pivalic acid (2 mmol, 204 mg) were added to a dried Andrews Glass™ Lab-Crest® Fisher-Porter tube with a stir bar. Then styrene (500 μmol) and arene (5 mL) were added by syringe. The tube was opened to air, sealed and pressurized with dinitrogen (60 psig). The mixture was stirred at 165° C. After 24 h, the reaction was allowed to cool to room temperature. The resultant mixture was diluted with ethyl acetate (40 mL) and washed with saturated sodium carbonate solution (50 mL). The aqueous and organic layers were separated. The aqueous layer was extracted with ethyl acetate (3×40 mL), and the combined organic layers were washed with water (3×10 mL) and dried over magnesium sulfate, filtered, and concentrated under vacuum. The concentrate was purified by column chromatography using hexanes as eluent.

Alkenylation of Toluene 3a-ortho 3a-meta 3a-para

Following the general procedure described above and using toluene as the arene, the target compounds mixture of 3a were obtained as a white solid (74 mg, 76%, ortho:para:meta=1:28:13). The products were separated and purified by flash column chromatography using hexanes as the eluent. However, due to the production of only a small quantity of 3a-ortho, we were unable to isolate this compound. Characterization of 3a-meta (2c) (This compound was reported in literature.[4]): $^1$H NMR (600 MHz, CDCl$_3$): δ 7.54 (m, 2H), 7.41-7.33 (m, 4H), 7.31-7.26 (m, 2H), 7.16-7.08 (m, 3H), 2.41 (s, 3H) ppm. $^{13}$C NMR (201 MHz, CDCl$_3$): δ 138.4, 137.6, 137.4, 129.0, 128.8, 128.7, 128.7, 128.6, 128.6, 128.6, 127.7, 127.4, 126.6, 123.9, 21.6 ppm.

Characterization of 3a-para (2b) (This compound was reported in literature.[4]): $^1$H NMR (600 MHz, CDCl$_3$): δ 7.53 (m, 2H), 7.45 (m, 2H), 7.38 (m, 2H), 7.28 (m, 1H), 7.20 (m, 2H), 7.13 (d, J=16.4 Hz, 1H), 7.09 (d, J=16.4 Hz, 1H), 2.39 (s, 3H) ppm. $^{13}$C NMR (201 MHz, CDCl$_3$): δ 137.7, 134.7, 129.5, 128.8, 128.8, 128.7, 127.8, 127.5, 126.5, 21.4, 21.4 ppm.

Alkenylation of Ethylbenzene

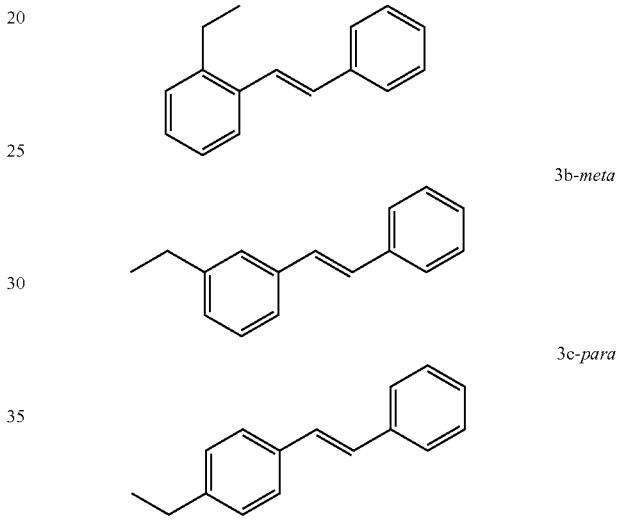

3b-ortho 3b-meta 3c-para

Following the general procedure described above and using ethylbenzene as the arene, the target compounds mixture of 3b were obtained as a white solid (82 mg, 81%, ortho:para:meta=0:3:1). The product mixture was purified by flash column chromatography using hexanes as the eluent. However, due to the production of only a small quantity of 3b-ortho, we were unable to see this compound from NMR.

Characterization of 3b mixture (3b-meta+3b-para): $^1$H NMR (600 MHz, CDCl$_3$) δ 7.54-7.48 (m, 2H$^{meta}$+2H$^{para}$), 7.45 (m, 2H$^{para}$), 7.39-7.33 (m, 3H$^{meta}$+2H$^{para}$), 7.30-7.23 (m, 3H$^{meta}$+1H$^{para}$), 7.20 (m, 2H$^{para}$), 7.14-7.04 (m, 3H$^{meta}$+2H$^{para}$), 2.72-2.63 (m, 4H$^{meta}$+4H$^{para}$), 1.30-1.23 (m, 6H$^{meta}$+6H$^{para}$) ppm. HRMS (HAPCI) m/z: Calcd for $C_{16}H_{16}^+$=208.1252, Found Mass=208.1232.

Alkenylation of Cumene

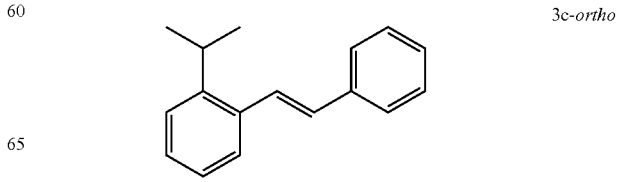

3c-ortho

3c-*meta*

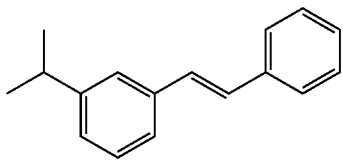

3c-*para*

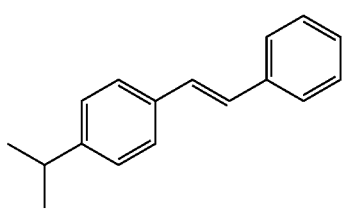

Following the general procedure described above and using cumene as the arene, the target compounds mixture of 3c were obtained as a white solid (88 mg, 77%, ortho:para:meta=0:2:1). The products mixture was purified by flash column chromatography using hexanes as the eluent. However, due to the production of only a small quantity of 3c-ortho, we were unable to see this compound from NMR.

Characterization of 3c mixture (3c-meta+3c-para): $^1$H NMR (600 MHz, CDCl$_3$): δ 7.54-7.49 (m, 2H$^{meta}$+2H$^{para}$), 7.46 (m, 2H$^{para}$), 7.39-7.33 (m, 3H$^{meta}$+2H$^{para}$), 7.31-7.21 (m, 3H$^{meta}$+3H$^{para}$), 7.17-7.14 (m, 1H$^{meta}$), 7.14-7.05 (m, 2H$^{meta}$+2H$^{para}$), 2.94 (m, 1H$^{meta}$+1H$^{para}$), 1.30 (d, J=6.9 Hz, 6H$^{para}$), 1.27 (d, J=7.0 Hz, 6H$^{meta}$) ppm. HRMS (HAPCI) m/z: Calcd for C$_{17}$H$_{19}$$^+$=223.1487, Found Mass=223.1476.

Alkenylation of Tert-Butylbenzene

3d-*ortho*

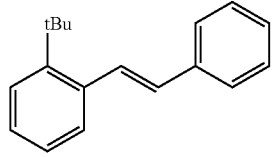

3d-*meta*

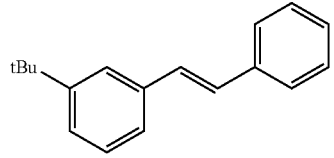

3d-*para*

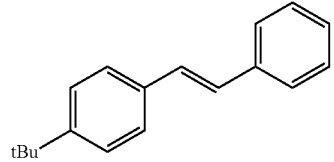

Following the general procedure described above and using tert-butylbenzene as the arene, the target compounds mixture of 3d were obtained as a white solid (96 mg, 81%, ortho:para:meta=0:2:1). The products mixture was purified by flash column chromatography using hexanes as the eluent. However, due to the production of only a small quantity of 3d-ortho, we were unable to see this compound from NMR. The assignment of peaks was achieved by comparison with the literature.[3]

Characterization of 3d mixture (3d-meta+3d-para): $^1$H NMR (600 MHz, CDCl$_3$): δ 7.57-7.49 (m, 2H$^{meta}$+2H$^{para}$), 7.48-7.44 (m, 2H$^{para}$), 7.43-7.33 (m, 4H$^{meta}$+2H$^{para}$), 7.33-7.28 (m, 2H$^{para}$), 7.28-7.23 (m, 1H$^{meta}$+1H$^{para}$), 7.18-7.03 (m, 2H$^{meta}$+2H$^{para}$), 1.36 (s, 9H$^{meta}$), 1.34 (s, 9H$^{para}$) ppm. HRMS (HAPCI) m/z: Calcd for C$_{17}$H$_{19}$$^+$=223.1487, Found Mass=223.1476.

Alkenylation of Para-Xylene (E)-2,5-dimethyl-1-styrylbenzene (3e)

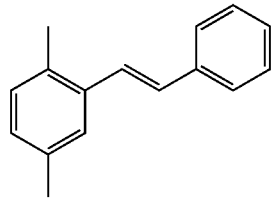 [SMILES: Cc1ccc(C)c(/C=C/c2ccccc2)c1]

Following the general procedure described above and using para-xylene as the arene, the target compound 3e was obtained as a white solid (23 mg, 22%) after 48 hours reaction. The product was purified by flash column chromatography using hexanes as the eluent. This compound was reported in literature.[5]

$^1$H NMR (600 MHz, CDCl$_3$): δ 7.53 (m, 2H), 7.42 (d, J=1.8 Hz, 1H), 7.37 (m, 2H), 7.32 (d, J=16.2 Hz, 1H), 7.26 (m, 2H), 7.08 (d, J=7.7 Hz, 1H), 7.03-6.97 (m, 2H), 2.39 (s, 3H), 2.36 (s, 3H) ppm. 13C NMR (151 MHz, CDCl$_3$): δ 137.9, 136.3, 135.7, 132.9, 130.5, 129.8, 128.8, 128.5, 127.7, 126.8, 126.7, 126.1, 21.2, 19.6 ppm. HRMS (HAPCI) m/z: Calcd for C$_{16}$H$_{16}$$^+$=208.1252, Found Mass=208.1243.

Alkenylation of Meta-Xylene (E)-3,5-dimethyl-1-styrylbenzene (3f)

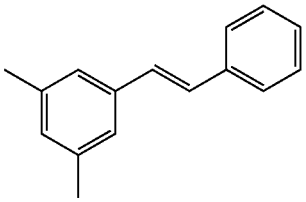 [SMILES: Cc1cc(C)cc(/C=C/c2ccccc2)c1]

Following the general procedure described above and using meta-xylene as the arene, the target compound 3f was obtained as a white solid (88 mg, 77%) after 48 hours reaction. The product was purified by flash column chromatography using hexanes as the eluent. This compound was reported in literature.[4] $^1$H NMR (600 MHz, CDCl$_3$): δ 7.53 (m, 2H), 7.38 (m, 2H), 7.27 (tt, J=7.3, 1.3 Hz, 1H), 7.17 (s, 2H), 7.11 (s, J=16.3 Hz, 1H), 7.07 (d, J=16.4 Hz, 1H), 6.93 (s, 1H), 2.36 (s, 6H). $^{13}$C NMR (151 MHz, CDCl$_3$): δ 138.2, 137.7, 137.4, 129.6, 129.0, 128.8, 127.6, 126.6, 124.6, 21.5 ppm. HRMS (HAPCI) m/z: Calcd for C$_{16}$H$_{16}$$^+$=208.1252, Found Mass=208.1246.

Alkenylation of Ortho-Xylene (E)-3,4-dimethyl-1-styrylbenzene (3g)

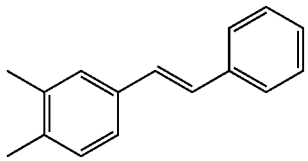 [SMILES: Cc1ccc(/C=C/c2ccccc2)cc1C]

Following the general procedure described above and using ortho-xylene as the arene, the target compound 3g was obtained as a white solid (81 mg, 71%). The product was purified by flash column chromatography using hexanes as the eluent. This compound was reported in literature.[13] $^1$H NMR (600 MHz, CDCl$_3$): δ 7.53 (m, 2H), 7.38 (m, 2H), 7.33 (s, 1H), 7.29 (dd, J=7.5, 1H), 7.27 (m, 1H), 7.15 (d, J=7.7 Hz, 1H), 7.09 (m, 2H), 2.32 (s, 3H), 2.30 (s, 3H) ppm. $^{13}$C NMR (151 MHz, CDCl$_3$): δ 137.7, 136.9, 136.4, 135.1, 130.1, 128.9, 128.8, 127.9, 127.7, 127.5, 126.5, 124.2, 20.0, 19.7 ppm. HRMS (HAPCI) m/z: Calcd for C$_{16}$H$_{16}$$^+$=208.1252, Found Mass=208.1239.

Alkenylation of 1,2,3-trimethylbenzene (E)-3,4,5-trimethyl-1-styrylbenzene (3h)

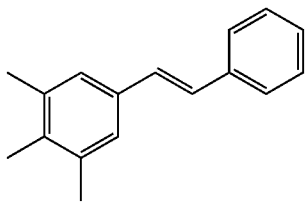 [SMILES: Cc1cc(/C=C/c2ccccc2)cc(C)c1C]

Following the general procedure described above and using 1,2,3-trimethylbenzene as the arene, the target compound 3h was obtained as a white solid (75 mg, 67%). The product was purified by flash column chromatography using hexanes as the eluent. This compound was reported in literature.[14] $^1$H NMR (600 MHz, CDCl$_3$): δ 7.51 (m, 2H), 7.35 (m, 2H), 7.25 (m, 2H), 7.19 (s, 2H), 7.07 (d, J=16.2 Hz, 1H), 7.04 (d, J=16.3 Hz, 1H), 2.33 (s, 6H), 2.20 (s, 3H) ppm. $^{13}$C NMR (151 MHz, CDCl$_3$): δ 137.8, 136.8, 135.0, 134.4, 128.9, 128.8, 127.5, 127.4, 126.5, 125.9, 20.8, 15.5 ppm. HRMS (HAPCI) m/z: Calcd for C$_{17}$H$_{19}$$^+$=223.1487, Found Mass=223.1481.

Alkenylation of Cyclohexylbenzene

3i-*ortho*

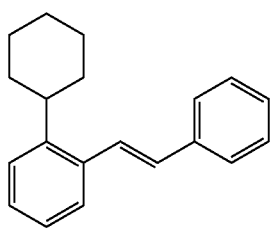

3i-*meta*

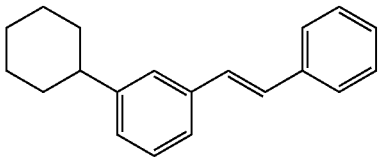

3i-*para*

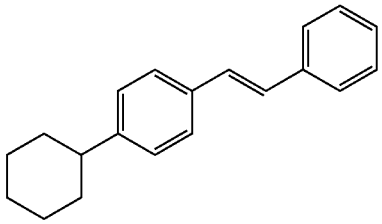

Following the general procedure described above and using cyclohexylbenzene as the arene, the target compounds mixture of 3i were obtained as a white solid (106 mg, 81%, ortho:para:meta=0:3:1). The products mixture was purified by flash column chromatography using hexanes as the eluent. However, due to the production of only a small quantity of 3i-ortho, we were unable to see this compound from NMR.

Characterization of 3i Mixture (3i-Meta+3i-Para):

$^1$H NMR (600 MHz, CDCl$_3$) δ 7.56-7.51 (m, 2H$^{meta}$+2H$^{para}$), 7.46 (m, 2H$^{para}$), 7.41-7.25 (m, 6H$^{meta}$+3H$^{para}$), 7.23 (m, 2H$^{para}$), 7.17-7.04 (m, 3H$^{meta}$+2H$^{para}$), 2.55 (m, 1H$^{meta}$+1 H$^{para}$), 2.02-1.73 (m, 5H$^{meta}$+5H$^{para}$), 1.53-1.21 (m, 5H$^{meta}$+5H$^{para}$) ppm. HRMS (HAPCI) m/z: Calcd for C$_{20}$H$_{22}$$^+$=262.1722, Found Mass=262.1709.

Alkenylation of Biphenyl

3j-*ortho*

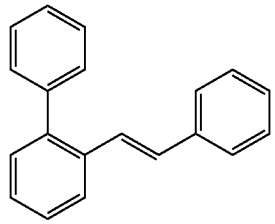

3j-*meta*

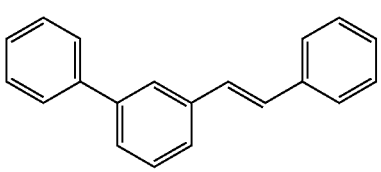

3j-*para*

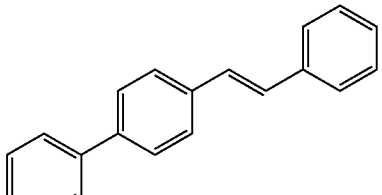

Following the general procedure described above and using biphenyl as the arene, 2.5 mL of mesitylene was added to the reaction mixture as the co-solvent, the target compounds mixture of 3j were obtained as a white solid (96 mg, 81%, ortho:para:meta=0:2:1). The products were separated and purified by flash column chromatography using hexanes as the eluent. However, due to the production of only a small quantity of 3j-ortho, we were unable to isolate this compound.

Characterization of 3j-meta (This compound was reported in literature.[6]): $^1$H NMR (600 MHz, CDCl$_3$): δ 7.74 (t, J=1.8 Hz, 1H), 7.64 (m, 2H), 7.55 (m, 2H), 7.53-7.43 (m, 5H), 7.38 (m, 3H), 7.29 (m, 1H), 7.19 (s, 2H) ppm. $^{13}$C NMR (151 MHz, CDCl$_3$): δ 141.9, 141.3, 138.0, 137.4, 129.24, 129.22, 128.93, 128.86, 128.8, 127.9, 127.6, 127.4, 126.71, 126.68, 125.6, 125.5 ppm.

Characterization of 3j-para (This compound was reported in literature.[15]): $^1$H NMR (600 MHz, CDCl$_3$): δ 7.65-7.57 (m, 6H), 7.54 (m, 2H), 7.48 (m, 2H), 7.40-7.34 (m, 3H), 7.38 (m, 1H), 7.16 (s, 2H) ppm. $^{13}$C NMR (151 MHz, CDCl$_3$): δ 140.8, 140.5, 137.5, 136.6, 129.0 (d, J=1.8 Hz), 128.92, 128.86, 128.4, 127.51, 127.48, 127.1, 127.1, 126.7 ppm. HRMS (HAPCI) m/z: Calcd for C$_{20}$H$_{16}$$^+$=256.1252, Found Mass=256.1250.

Alkenylation of Fluorobenzene

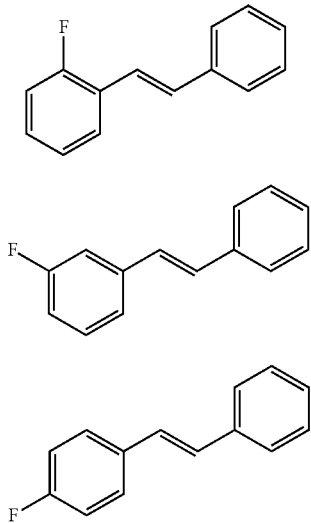

3k-ortho 3k-meta 3k-para

Following the general procedure described above and using fluorobenzene as the arene, the target compounds mixture of 3k were obtained as a white solid (81 mg, 82%, ortho:para:meta=1:28:23). The products mixture was purified by flash column chromatography using hexanes as the eluent. However, due to the production of only a small quantity of 3k-ortho, we were unable to see this compound in NMR.

Characterization of 3k-meta: $^1$H NMR (600 MHz, CDCl$_3$): δ 7.52 (d, J=7.7 Hz, 2H), 7.37 (t, J=7.6 Hz, 2H), 7.33-7.27 (m, 3H), 7.22 (d, J=10.0 Hz, 1H), 7.11, 7.07 (ABq, Δv$_{AB}$=24 Hz, J$_{AB}$=18 Hz, 2H), 6.95 (t, J=7.8 Hz, 1H) ppm. $^{13}$C NMR (201 MHz, CDCl$_3$): δ 163.3 (d), 139.9 (d), 137.0, 130.2 (d), 130.2, 128.9, 128.2, 127.6 (d), 126.8, 122.6 (d), 114.5 (d), 112.9 (d) ppm. $^{19}$F NMR (564 MHz, CDCl$_3$): δ −111.8 (td, J=9.3, 6.2 Hz, 1H) ppm.

Characterization of 3k-para: $^1$H NMR (600 MHz, CDCl$_3$): δ 7.49 (m, 4H), 7.36 (t, J=7.6 Hz, 2H), 7.28 (s, 1H), 7.09-7.00 (m, 4H) ppm. $^{13}$C NMR (201 MHz, CDCl$_3$): δ 162.3 (d, J=247.3 Hz), 137.2, 133.5 (d, J=3.3 Hz), 128.7, 128.5 (d, J=2.3 Hz), 128.0 (d, J=7.9 Hz), 127.7, 127.5, 126.4, 115.6 (d, J=21.6 Hz) ppm. $^{19}$F NMR (564 MHz, CDCl$_3$): δ −112.5 (tt, J=8.6, 5.4 Hz) ppm.

HRMS (HAPCI) m/z: Calcd for C$_{14}$H$_{11}$F$^+$=198.0845, Found Mass=198.0842.

Alkenylation of Chlorobenzene

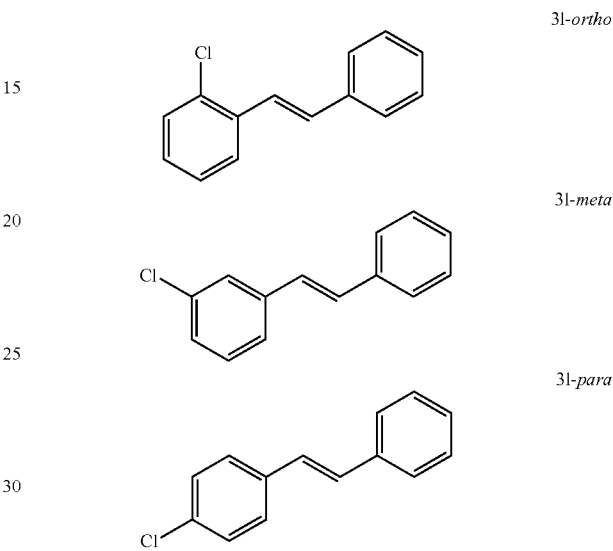

3l-ortho 3l-meta 3l-para

Following the general procedure described above and using chlorobenzene as the arene, the target compounds mixture of 3l were obtained as a white solid (94 mg, 87%, ortho:para:meta=0:2:1). The products were separated and purified by flash column chromatography using hexanes as the eluent. However, due to the production of only a small quantity of 3l-ortho, we were unable to isolate this compound.

Characterization of 3l-meta: $^1$H NMR (600 MHz, CDCl$_3$): δ 7.55-7.50 (m, 3H), 7.42-7.36 (m, 3H), 7.33-7.28 (m, 2H), 7.25 (ddd, J=7.9, 2.1, 1.2 Hz, 1H), 7.13 (d, J=16.3 Hz, 1H), 7.05 (d, J=16.3 Hz, 1H) ppm. $^{13}$C NMR (201 MHz, CDCl$_3$): δ 139.4, 136.9, 134.8, 130.3, 130.0, 128.9, 128.2, 127.6, 127.3, 126.8, 126.4, 124.9 ppm.

Characterization of 3l-para: $^1$H NMR (600 MHz, CDCl$_3$): δ 7.51 (d, J=7.6 Hz, 2H), 7.44 (d, J=8.6 Hz, 2H), 7.37 (t, J=7.7 Hz, 2H), 7.33 (d, J=8.5 Hz, 2H), 7.28 (t, J=7.3 Hz, 1H), 7.08, 7.05 (ABq, Δv$_{AB}$=13.4 Hz, J$_{AB}$=12 Hz, 2H) ppm. $^{13}$C NMR (201 MHz, CDCl$_3$): δ 137.1, 136.0, 133.3, 129.5, 129.0, 128.9, 128.0, 127.8, 127.5, 126.7 ppm.

HRMS (HAPCI) m/z: Calcd for C$_{14}$H$_{11}$Cl$^+$=214.0549, Found Mass=214.0539.

Alkenylation of Bromobenzene

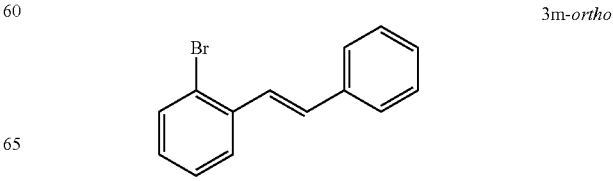

3m-ortho

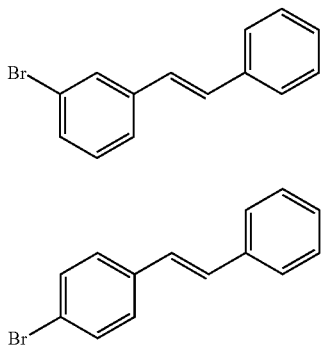

3m-*meta*

3m-*para*

Following the general procedure described above and using bromobenzene as the arene, the target compounds mixture of 3m and undesired product stilbene 2a were obtained as a white solid. The products were separated and purified by flash column chromatography using hexanes as the eluent. Only 21 mg 21% of 3m-para was cleanly separated.

Figure 5:
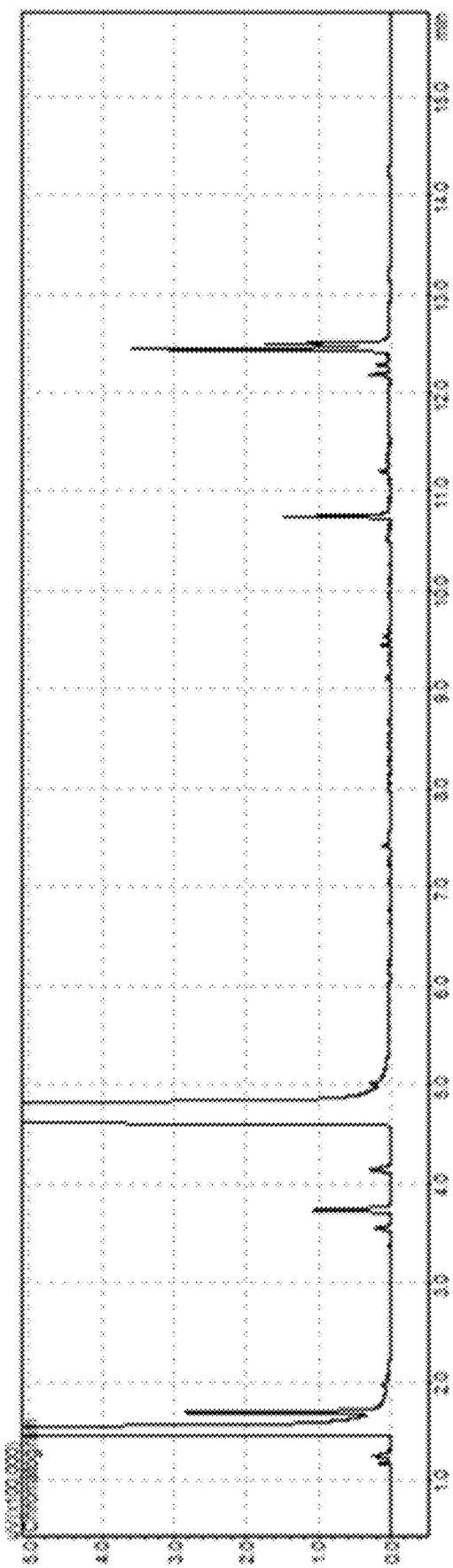
FIG. 5 illustrates a representative GC-FID chromatogram of a reaction mixture from the reaction between bromobenzene and styrene.

Representative GC-FID chromatogram (FIG. 5) of a reaction mixture from the reaction between bromobenzene and styrene. Peak assignments: 1-2 minutes dichloromethane, acetone and benzene; 4.1 minutes styrene; 4.6-5 minutes bromobenzene; 10.8 minutes trans-stilbene; 12-13 minutes mixture of bromostilbenes. GC-FID Parameters: starting temperature: 50° C.; time at starting temp: 2.5 min; ramp1: 20° C./min up to 240° C.; hold for 6 min; flow rate (carrier): 3.01 mL/min (He); split ratio: 35:1; inlet temperature: 200° C.; detector temperature: 240° C.

Characterization of 3m-Para:

$^1$H NMR (600 MHz, CDCl$_3$): δ 7.56-7.46 (m, 4H), 7.41-7.33 (m, 4H), 7.28 (m, 1H), 7.10 (d, J=16.3 Hz, 1H), 7.04 (d, J=16.3 Hz, 1H) ppm. $^{13}$C NMR (201 MHz, CDCl$_3$): δ 137.1, 136.4, 131.9, 129.6, 128.9, 128.12, 128.05, 127.6, 126.7, 121.5 ppm.

Alkenylation of Iodobenzene

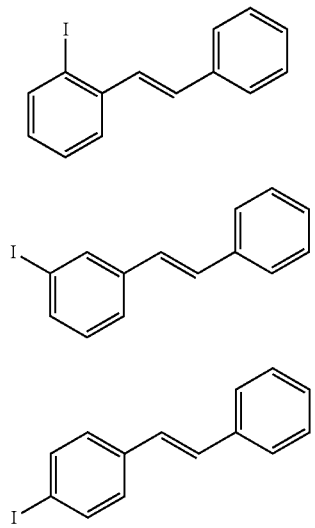

3n-*ortho*

3n-*meta*

3n-*para*

Following the general procedure described above and using iodobenzene as the arene, the target compounds mixture of 3n and undesired product stilbene 2a were obtained as a white solid. The products were separated and purified by flash column chromatography using hexanes as the eluent.

Figure 6:
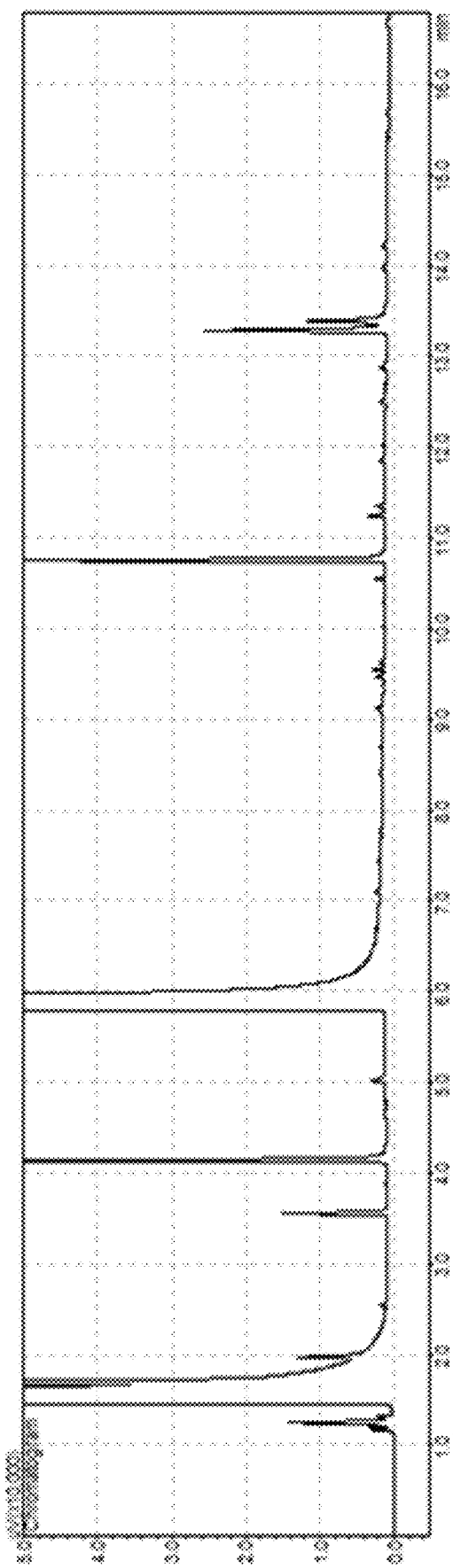
FIG. 6 illustrates a representative GC-FID chromatogram (FIG. 6) of a reaction mixture from the reaction between iodobenzene and styrene.

Representative GC-FID chromatogram (FIG. 6) of a reaction mixture from the reaction between iodobenzene and styrene. Peak assignments: 1-2 minutes dichloromethane, acetone and benzene; 4.1 minutes styrene; 5.6-7 minutes iodobenzene; 10.8 minutes trans-stilbene; 13-14 minutes mixture of iodostilbenes. GC-FID Parameters: starting temperature: 50° C.; time at starting temp: 2.5 min; ramp1: 20° C./min up to 240° C.; hold for 6 min; flow rate (carrier): 3.01 mL/min (He); split ratio: 35:1; inlet temperature: 200° C.; detector temperature: 240° C.

Alkenylation of Pentafluorobenzene (E)-2,3,4,5,6-pentafluoro-1-styrylbenzene (3o)

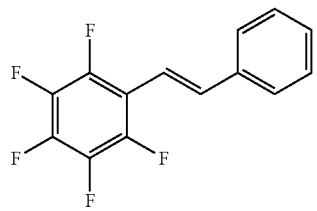 [SMILES: Fc1c(F)c(F)c(/C=C/c2ccccc2)c(F)c1F]

Following the general procedure described above and using pentafluorobenzene as arene, the target compound 3o was obtained as a white solid (82 mg, 61%). The product was purified by flash column chromatography using hexanes as the eluent. $^1$H NMR (600 MHz, CDCl$_3$): δ 7.54 (m, 2H), 7.46-7.38 (m, 3H), 7.35 (m, 1H), 6.99 (d, J=16.8 Hz, 1H). $^{13}$C NMR (201 MHz, CDCl$_3$): δ 145.2 (dm, J=250.1 Hz), 139.5 (dm, J=254.9 Hz), 137.8 (dm, J=252.1 Hz), 137.2 (t, J=8.2 Hz), 136.5, 129.0, 128.9, 126.9, 112.7, 112.4 (td, J=13.7, 4.5 Hz) ppm. $^{19}$F NMR (564 MHz, CDCl$_3$): δ −143.3 (dd, J=21.2 Hz, 7.1 Hz, 2F), −157.2 (t, J=20.8 Hz, 1F), −163.6 (td, J=20.8 Hz, 6.8 Hz, 2F) ppm. HRMS (HAPCI) m/z: Calcd for=C$_{14}$H$_7$F$_5^+$=270.0468, Found Mass=270.0465.

Alkenylation of 1,2-dichlorobenzene (E)-3,4-dichloro-1-styrylbenzene (3p)

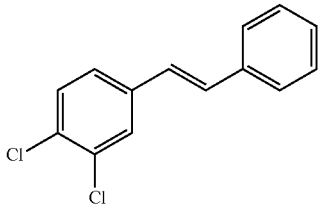 [SMILES: Clc1ccc(/C=C/c2ccccc2)cc1Cl]

Following the general procedure described above and using pentafluorobenzene as arene, the target compound 3p was obtained as a white solid (81 mg, 74%). The product was purified by flash column chromatography using hexanes as the eluent. This compound was reported in literature.[8] $^1$H NMR (600 MHz, CDCl$_3$): δ 7.59 (d, J=2.1, 1H), 7.50 (m, 2H), 7.42 (d, J=8.3 Hz, 1H), 7.38 (m, 2H), 7.33 (dd, J=8.3, 2.1, 1H), 7.30 (m, 1H), 7.09 (d, J=16.3 Hz, 1H), 6.99 (d, J=16.3 Hz, 1H) ppm. $^{13}$C NMR (151 MHz, CDCl$_3$): δ 137.6, 136.7, 132.9, 131.3, 130.7, 130.7, 128.9, 128.4, 128.2, 126.8, 126.3, 125.8 ppm. HRMS (HAPCI) m/z: Calcd for C$_{14}$H$_{10}$Cl$_2$$^+$=248.0160, Found Mass=248.0163.

Alkenylation of 1,3-dibromobenzene (E)-3,5-dibromo-1-styrylbenzene (3q)

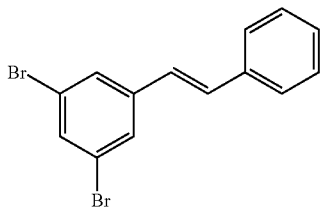 [SMILES: Brc1cc(Br)cc(/C=C/c2ccccc2)c1]

Following the general procedure described above and using 1,3-dibromobenzene as arene, the target compound 3q was obtained as a white solid (125 mg, 74%). The product was purified by flash column chromatography using hexanes as the eluent. This compound was reported in literature.[16] $^1$H NMR (600 MHz, CDCl$_3$): δ 7.57 (d, J=1.6 Hz, 2H), 7.54 (t, J=1.7 Hz, 1H), 7.50 (m, 2H), 7.38 (m, 2H), 7.31 (m, 1H), 7.10 (d, J=16.3 Hz, 1H), 6.93 (d, J=16.3 Hz, 1H) ppm. $^{13}$C NMR (151 MHz, CDCl$_3$): δ 141.2, 136.4, 132.8, 131.7, 129.0, 128.6, 128.2, 127.0, 125.8, 123.4 ppm. HRMS (HAPCI) m/z: Calcd for C$_{14}$H$_{10}$Br$_2$$^+$=335.9149, Found Mass=335.9142.

Alkenylation of α,α,α-trifluorotoluene

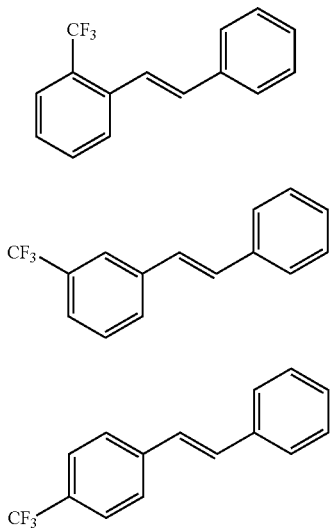

3r-ortho 3r-meta 3r-para

Following the general procedure described above and using α, α, α-trifluorotoluene as the arene, the target compounds mixture of 3r were obtained as a white solid (108 mg, 87%, ortho:para:meta=0:2:1). The product was purified by flash column chromatography using hexanes as the eluent. The assignment of peaks was achieved by comparison with the literature.[3] $^1$H NMR (600 MHz, CDCl$_3$): δ 7.78 (s, 1H$^{meta}$), 7.69 (d, J=7.0, 1H$^{meta}$), 7.65-7.59 (m, 4H$^{para}$), 7.58-7.51 (m, 3H$^{meta}$+2H$^{para}$), 7.48 (t, J=7.7 Hz, 1H$^{meta}$), 7.43-7.37 (m, 2H$^{meta}$+2H$^{para}$), 7.35-7.29 (m, 1H$^{meta}$+1H$^{para}$), 7.23-7.09 (m, 2H$^{meta}$+2H$^{para}$) $^{19}$F NMR (564 MHz, CDCl$_3$): δ −60.84 (s, 3F$^{para}$), −61.14 (s, 3F$^{meta}$) ppm.

HRMS (HAPCI) m/z: Calcd for=C$_{15}$H$_{11}$F$_3$$^+$=248.0813, Found Mass=248.0813.

Alkenylation of Naphathalene (E)-2-styrylnaphthalene (3s)

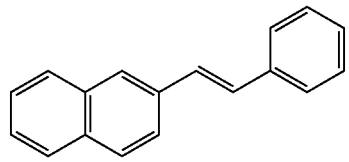 [SMILES: C(=C\c1ccc2ccccc2c1)/c1ccccc1]

Following the general procedure described above and using naphthalene as the arene, 2.5 mL of mesitylene was added to the reaction mixture as the co-solvent, the target compound 3s was obtained as a white solid (86 mg, 75%). The product was purified by flash column chromatography using hexanes as the eluent. This compound was reported in literature.[6]

$^1$H NMR (600 MHz, CDCl$_3$): δ 7.86 (br, s, 1H), 7.85-7.79 (m, 2H), 7.75 (dd, J=8.6, 1.8 Hz, 1H), 7.57 (m, 2H), 7.50-7.42 (m, 2H), 7.38 (m, 2H), 7.29 (d, J=16.4 Hz, 1H), 7.28 (m, 2H). 7.24 (d, J=16.3 Hz, 1H) ppm. $^{13}$C NMR (151 MHz, CDCl$_3$): δ 137.5, 135.0, 133.9, 133.2, 129.2, 128.9, 128.9, 128.5, 128.1, 127.8, 127.8, 126.8, 126.7. 126.5, 126.0, 123.7 ppm. HRMS (HAPCI) m/z: Calcd for C$_{18}$H$_{14}$$^+$=230.1096, Found Mass=230.1084.

Alkenylation of Furan (E)-2-styrylfuran (3t)

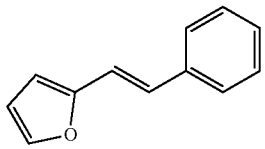 [SMILES: C(=C\c1ccco1)/c1ccccc1]

Following the general procedure described above and using furan as the arene, the target compound 3t was obtained as a white solid (42 mg, 49%). The product was purified by flash column chromatography using hexanes as the eluent. This compound was reported in literature.[4]

$^1$H NMR (600 MHz, CDCl$_3$): δ 7.47 (m, 2H), 7.41 (dd, J=1.8, 0.7 Hz, 1H), 7.35 (m, 2H), 7.26 (m, 1H), 7.05 (d, J=16.3 Hz, 1H), 6.91 (d, J=16.3 Hz, 1H), 6.43 (dd, J=3.3, 1.8 Hz, 1H), 6.36 (dd, J=3.3, 0.7 Hz, 1H). HRMS (HAPCI) m/z: Calcd for C$_{12}$H$_{11}$O$^+$=171.0810, Found Mass=171.0787.

Alkenylation of Trimethylsilyl Benzene

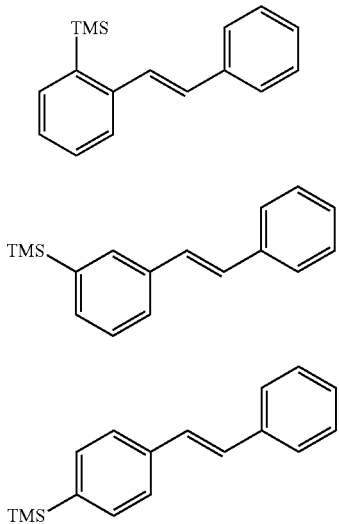

3u-ortho 3u-meta 3u-para

Following the general procedure described above and using trimethylsilyl benzene as the arene, the target compounds mixture of 3u were obtained as a white solid (115 mg, 91%, ortho:para:meta=0:2:1). The product was purified by flash column chromatography using hexanes as the eluent.

Characterization of 3u Mixture (3u-Meta+3u-Para):

$^1$H NMR (600 MHz, CDCl$_3$): δ 7.70 (m, 1H$^{meta}$), 7.61-7.52 (m, 2H$^{meta}$+6H$^{para}$), 7.48 (dt, J=7.3, 1.2 Hz, 1H$^{meta}$), 7.41 (m, 3H$^{meta}$+2H$^{para}$), 7.33-7.29 (m, 1H$^{meta}$+1H$^{para}$), 7.22-7.13 (m, 3H$^{meta}$+2H$^{para}$), 0.37 (s, 9H$^{meta}$), 0.34 (s, 9H$^{para}$) ppm.

HRMS (HAPCI) m/z: Calcd for C$_{17}$H$_{20}$Si$^+$=252.1334, Found Mass=252.1329.

Alkenylation of Anisole

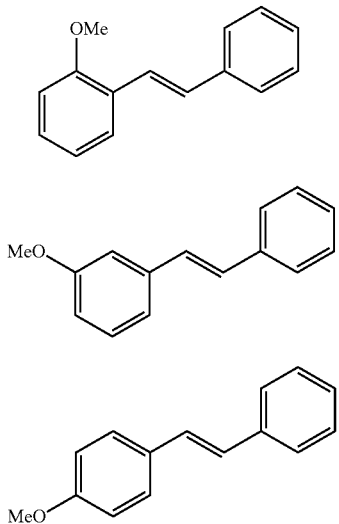

3v-ortho 3v-meta 3v-para

Following the general procedure described above and using anisole as the arene, reaction was run under 135° C. for 96 hours, the reactor was cooled down and purge by fresh air every 24 hours, the target compounds mixture of 3v were obtained as a colorless liquid (85 mg, 81%, ortho:para:meta=0.3:1.7:1) The product was purified by flash column chromatography using hexanes and ethyl acetate (v/v=9:1) as the eluent. However, due to the production of only a small quantity of 3v-ortho, we were unable to isolate this compound.

Characterization of 3v-Meta:

$^1$H NMR (600 MHz, CDCl$_3$): δ 7.55 (m, 2H), 7.40 (m, 2H), 7.35-7.28 (m, 2H), 7.19-7.12 (m, 3H), 7.10 (dd, J=2.6, 1.0 Hz, 1H), 6.87 (ddd, J=8.2, 2.5, 0.9 Hz, 1H), 3.88 (s, 3H) ppm. $^{13}$C NMR (151 MHz, CDCl$_3$): δ 160.0, 138.9, 137.4, 129.8, 129.1, 128.8, 128.7, 127.8, 126.7, 119.4, 113.4, 111.9, 55.3 ppm.

Characterization of 3v-Para:

$^1$H NMR (600 MHz, CDCl$_3$): δ 7.48 (dd, J=20.1, 8.0 Hz, 4H), 7.35 (t, J=7.5 Hz, 2H), 7.24 (t, J=7.4 Hz, 1H), 7.07, 6.98 (ABq, Δv$_{AB}$=52.6 Hz, J$_{AB}$=16.3 Hz, 2H), 6.91 (d, J=8.4 Hz, 2H), 3.84 (s, 3H) ppm. $^{13}$C NMR (201 MHz, CDCl$_3$): δ 159.4, 137.8, 130.3, 128.78, 128.4, 127.9, 127.4, 126.8, 126.4, 114.3, 77.2, 55.5 ppm.

Characterization of 3v Mixture:

HRMS (HAPCI) m/z: Calcd for C$_{15}$H$_{15}$O$^+$=211.1123, Found Mass=211.1122.

Alkenylation of 1,3-dimethoxybenzene (E)-3,5-dimethoxyl-1-styrylbenzene (3w)

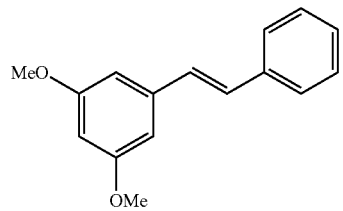 [SMILES: COc1cc(/C=C/c2ccccc2)cc(OC)c1]

Following the general procedure described above and using 1,3-dimethoxybenzene as the arene, reaction was run under 135° C. for 96 hours, the reactor was cooled down and purge by fresh air every 24 hours, the target compound of 3w were obtained as a colorless liquid (89 mg, 74%). The product was purified by flash column chromatography using hexanes and ethyl acetate (v/v=9:1) as the eluent. This compound was reported in literature.[4] $^1$H NMR (600 MHz, CDCl$_3$): δ 7.52 (m, 2H), 7.37 (m, 2H), 7.28 (m, 1H), 7.11 (d, J=16.3 Hz, 1H), 7.05 (d, J=16.3 Hz, 1H), 6.70 (d, J=2.3 Hz, 2H), 6.42 (t, J=2.3 Hz, 1H), 3.85 (s, 6H) ppm. $^{13}$C NMR (151 MHz, CDCl$_3$): δ 161.1, 139.5, 137.3, 129.3, 128.8, 127.9, 126.7, 104.7, 100.1, 55.5 ppm. HRMS (HAPCI) m/z: Calcd for C$_{16}$H$_{16}$O$_2$$^+$=240.1150, Found Mass=240.1158.

Alkenylation of 1,2-dimethoxybenzene (E)-3,4-dimethoxyl-1-styrylbenzene (3x)

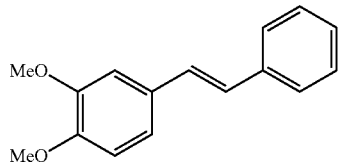 [SMILES: COc1ccc(/C=C/c2ccccc2)cc1OC]

Following the general procedure described above and using 1,2-dimethoxybenzene as the arene, reaction was run under 135° C. for 96 hours, the reactor was cooled down and purge by fresh air every 24 hours, the target compound of 3x were obtained as a colorless liquid (88 mg, 73%). The product was purified by flash column chromatography using hexanes and ethyl acetate (v/v=9:1) as the eluent. This compound was reported in literature.[4] $^1$H NMR (600 MHz, CDCl$_3$): δ 7.50 (m, 2H), 7.35 (m, 2H), 7.25 (m, 1H), 7.09-7.03 (m, 3H), 6.98 (d, J=16.3 Hz, 1H), 6.87 (d, J=8.2 Hz, 1H), 3.95 (s, 3H), 3.91 (s, 3H) ppm. 13C NMR (151 MHz, CDCl$_3$): δ 149.3, 149.1, 137.7, 130.6, 128.8, 128.6, 127.4, 127.0, 126.4, 120.0, 111.4, 108.9, 56.1, 56.0 ppm. HRMS (HAPCI) m/z: Calcd for $C_{16}H_{16}O_2^+$=240.1150, Found Mass=240.1149.

Alkenylation of 1,2,3-trimethoxybenzene (E)-3,4,5-trimethoxyl-1-styrylbenzene (3y)

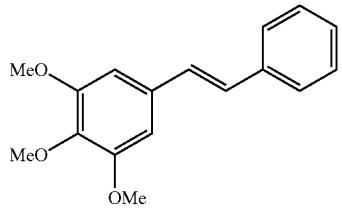 [SMILES: COc1cc(/C=C/c2ccccc2)cc(OC)c1OC]

Following the general procedure described above and using 1,2,3-trimethoxybenzene as the arene, reaction was run under 135° C. for 96 hours, the reactor was cooled down and purge by fresh air every 24 hours, the target compound of 3y were obtained as a light yellow liquid (99 mg, 73%). The product was purified by flash column chromatography using hexanes and ethyl acetate (v/v=9:1) as the eluent. This compound was reported in literature.[4] $^1$H NMR (600 MHz, CDCl$_3$): δ 7.51 (m, 2H), 7.36 (m, 2H), 7.27 (m, 1H), 7.05 (d, J=16.3 Hz, 1H), 7.01 (d, J=16.2 Hz, 1H), 3.92 (s, 6H), 3.88 (s, 3H) ppm. $^{13}$C NMR (151 MHz, CDCl$_3$): δ 153.6, 137.4, 133.2, 128.9, 128.8, 128.4, 127.8, 126.6, 103.8, 81.0, 61.1, 56.3 ppm. HRMS (HAPCI) m/z: Calcd for $C_{17}H_{18}O_3^+$=270.1256, Found Mass=270.1254.

Synthesis of bioactive stilbenes derivatives. Under an atmosphere of dry nitrogen, di-µ-acetatotetrakis(dihaptoethene)dirhodium(I) (1) (2.5 µmol, 550 µg), copper(II) pivalate (400 µmol, 106 mg) and pivalic acid (2 mmol, 204 mg) were added to a dried Andrews Glass™ Lab-Crest® Fisher-Porter tube with a stir bar. Then, vinyl arene (500 µmol) and arene (5 mL) were added by syringe. The tube was opened to air, sealed and pressurized with dinitrogen (60 psig). The mixture was stirred at 135° C. for 96 hours. After every 24 h, the reaction was allowed to cool to room temperature and fresh air was purged into the reactor via a long needle. After the reaction finished, the resultant mixture was diluted with ethyl acetate (40 mL) and washed with saturated sodium carbonate solution (50 mL). The aqueous and organic layers were separated. The aqueous layer was extracted with ethyl acetate (3×40 mL), and the combined organic layers were washed with water (3×10 mL), dried over magnesium sulfate, filtered and concentrated under vacuum. The concentrate was purified by column chromatography using 9:1 hexanes:ethyl acetate as eluent.

Alkenylation of 1,3-dimethoxybenzene Using 4-methoxystyrene, Synthesis of (E)-1,3-dimethoxy-5-(4-methoxystyryl)benzene

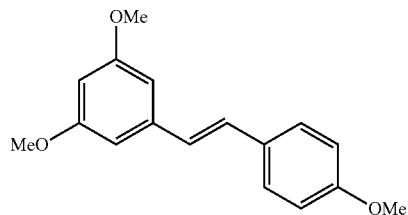 [SMILES: COc1ccc(/C=C/c2cc(OC)cc(OC)c2)cc1]

Following the general procedure described above and using 1,3-dimethoxybenzene as the arene, 4-vinylanisole as the vinylarene, reaction was run under 135° C. for 96 hours, the reactor was cooled down and purge by fresh air every 24 hours, the target compound of (E)-1,3-dimethoxy-5-(4-methoxystyryl)benzene was obtained as a light yellow liquid (92 mg, 68%). The product was purified by flash column chromatography using hexanes and ethyl acetate (v/v=9:1) as the eluent. This compound was reported in literature.[6]
$^1$H NMR (600 MHz, CDCl$_3$): δ 7.45 (m, 2H), 7.04 (d, J=16.3 Hz, 1H), 6.93-6.89 (m, 3H), 6.66 (d, J=2.3 Hz, 2H), 6.38 (t, J=2.2 Hz, 1H), 3.83 (s, 9H) ppm. $^{13}$C NMR (151 MHz, CDCl$_3$): δ 161.1, 159.6, 139.9, 130.1, 128.9, 127.9, 126.7, 114.3, 104.5, 99.8, 55.50, 55.47 ppm. HRMS (HAPCI) m/z: Calcd for $C_{17}H_{18}O_3^+$=270.1256, Found Mass=270.1259.

Deprotection of Trimethyl Resveratrol

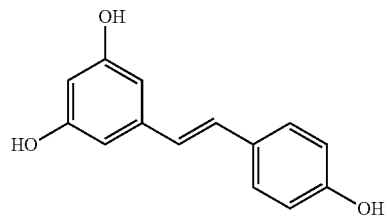 [SMILES: Oc1ccc(/C=C/c2cc(O)cc(O)c2)cc1]

We followed a published with some modification.[4] (E)-1,3-dimethoxy-5-(4-methoxystyryl)benzene (92 mg, 340 gmol, 1.0 equiv) was dissolved in CH$_2$Cl$_2$ (15 mL) and a solution of BBr$_3$ (1.0 M in CH$_2$Cl$_2$, 3.3 mmol, 3.3 mL, 9.0 equiv) was added at −78° C. The mixture was stirred for 1 h at −78° C. Then the reaction was allowed to warm to room temperature, H$_2$O (25 mL) was added and the mixture was poured into H$_2$O (25 mL). Extraction with EtOAc (3×25 mL), washing of the combined organic layers with $H_2O$ (25 mL), brine (25 mL), drying over $MgSO_4$ and concentration under reduced pressure gave the crude product which was purified by flash column chromatography using hexanes and ethyl acetate (v/v=9:1) as the eluent. The target compound of resveratrol was obtained as a white solid (74 mg, 96%).

$^1$H NMR (600 MHz, DMSO-$d_6$): δ 9.53 (s, 1H), 9.17 (s, 2H), 7.39 (m, 2H), 6.92 (d, J=16.3 Hz, 1H), 6.81 (d, J=16.3 Hz, 1H), 6.75 (m, 2H), 6.37 (d, J=2.1 Hz, 2H), 6.11 (t, J=2.1 Hz, 1H) ppm. $^{13}$C NMR (201 MHz, DMSO-$d_6$): δ 158.5, 157.2, 139.2, 128.1, 127.8, 127.8, 125.6, 115.5, 104.3, 101.7 ppm.

Synthesis of (E)-1,2,3-trimethoxy-5-(4-methoxystyryl)benzene (DMU-212)

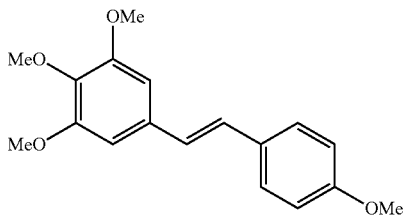 [SMILES: COc1ccc(/C=C/c2cc(OC)c(OC)c(OC)c2)cc1]

Following the general procedure described above and using 1,2,3-trimethoxybenzene as the arene, reaction was performed at 135° C. for 96 hours, the reactor was allowed to cool to room temperature and purged with air every 24 hours. The target compound DMU-212 was obtained as a light yellow liquid (106.6 mg, 71%). The product was purified by flash column chromatography using hexanes and ethyl acetate (v/v=9:1) as the eluent. This compound was reported in literature.[17] $^1$H NMR (600 MHz, CDCl$_3$): δ 7.45 (m, 2H), 6.97 (d, J=16.2 Hz, 1H), 6.94-6.87 (m, 3H), 6.72 (s, 2H), 3.92 (s, 6H), 3.87 (s, 3H), 3.83 (s, 3H) ppm. $^{13}$C NMR (151 MHz, CDCl$_3$): δ 159.4, 153.5, 137.8, 133.6, 130.2, 127.9, 127.8, 126.7, 114.3, 103.4, 61.1, 56.5, 55.5 ppm.

Synthesis of (E)-1,3-dimethoxy-5-(4-methoxystyryl)benzene—gram scale. An oven dried 250 mL two-neck round bottom flask was charge with di-μ-acetatotetrakis(dihaptoethene)dirhodium(I) (25 μmol, 5.5 mg, 0.5 mol %), copper (II) pivalate (4 mmol, 1.06 g) and pivalic acid (20 mmol, 2.04 g). To the flask 50 mL of 1,3-dimethoxybenzene were added. The solution was stirred at room temperature for 10 minutes to dissolve all of the copper salt. Then, 0.665 mL of 4-methoxystyrene (5 mmol) were added to the reaction mixture. The reaction flask was connected to compressed air via an adapter and a condenser (note: the air flow will facilitate the removal of the reaction solvent, thus a long condenser is needed). The reaction mixture was stirred at 135° C. for 96 hours. After completion of the reaction, the flask was allowed to cool to room temperature. The resultant mixture was diluted with ethyl acetate (150 mL) and washed with saturated sodium carbonate solution (200 mL). The aqueous and organic layers were separated. The aqueous layer was extracted with ethyl acetate (3×200 mL), and the combined organic layers were washed with water (3×200 mL), dried over magnesium sulfate, filtered, and concentrated under vacuum. The product was purified by flash column chromatography using hexanes and ethyl acetate (v/v=9:1) as the eluent. 838 mg of desired product (E)-1,3-dimethoxy-5-(4-methoxystyryl)benzene (62%) was isolated.

Synthesis of (E)-1,2-dichloro-4-styrylbenzene—gram scale An oven dried 250 mL two-neck round bottom flask was charge with di-μ-acetatotetrakis(dihaptoethene)dirhodium(I) (1) (25 mol, 5.5 mg, 0.5 mol %), copper(II) pivalate (0.2 mmol, 53 mg) and pivalic acid (20 mmol, 2.04 g). To the flask 50 mL of 1,2-dichlororbenzene were added. The solution was stirred at room temperature for 10 minutes to dissolve all of the copper salt. Then, 0.573 mL of styrene (5 mmol) were added to the reaction mixture. The reaction flask was connected to compressed air via an adapter and a condenser (note: the air flow will facilitate the removal of the reaction solvent, thus a long condenser is needed). The reaction mixture was stirred at 135° C. for 96 hours. After completion of the reaction, the flask was allowed to cool to room temperature. The resultant mixture was diluted with ethyl acetate (150 mL) and washed with saturated sodium carbonate solution (200 mL). The aqueous and organic layers were separated. The aqueous layer was extracted with ethyl acetate (3×200 mL), and the combined organic layers were washed with water (3×200 mL), dried over magnesium sulfate, filtered, and concentrated under vacuum. The product was purified by flash column chromatography using hexanes as the eluent. 1.05g of the desired product (E)-1,2-dichloro-4-styrylbenzene was isolated (84%).

REFERENCES FOR SUPPLEMENTAL INFORMATION FOR EXAMPLE 1

1. Xie, L. H.; Suh, M. P., Flexible metal-organic framework with hydrophobic pores. *Chem. Eur. J* 2011, 17(49), 13653-6.
2. Werner, H.; Poelsma, S.; Schneider, M. E.; Windmüller, B.; Barth, D., Synthesis and Reactivity of Bis(ethene) Rhodium(I) and Iridium(I) Carboxylato Complexes. *Chem. Ber.* 1996, 129 (6), 647-652.
3. Wang, S.-M.; Song, H.-X.; Wang, X.-Y.; Liu, N.; Qin, H.-L.; Zhang, C.-P., Palladium-catalyzed Mizoroki-Heck-type reactions of [Ph2SRfn][OTf] with alkenes at room temperature. *Chem. Commun.* 2016, 52 (80), 11893-11896.
4. Landge, V. G.; Yadav, V.; Subaramanian, M.; Dangarh, P.; Balaraman, E., Nickel(ii)-catalyzed direct olefination of benzyl alcohols with sulfones with the liberation of H2. *Chem. Commun.* 2019, 55 (43), 6130-6133.
5. Bhunia, A.; Studer, A., Synthesis of Highly Substituted Arenes via Cyclohexadiene-Alkene C—H Cross Coupling and Aromatization. *ACS Catal.* 2018, 8 (2), 1213-1217.
6. Mochida, S.; Hirano, K.; Satoh, T.; Miura, M., Synthesis of stilbene and distyrylbenzene derivatives through rhodium-catalyzed ortho-olefination and decarboxylation of benzoic acids. *Org. Lett.* 2010, 12 (24), 5776-9.
7. Kothandaraman, P.; Foo, S. J.; Chan, P. W. H., Gold-Catalyzed Intramolecular Allylic Amination of 2-Tosylaminophenylprop-1-en-3-ols. A Concise Synthesis of (±)-Angustureine. *The Journal of Organic Chemistry* 2009, 74 (16), 5947-5952.
8. Xiao, Q.; Ma, J.; Yang, Y.; Zhang, Y.; Wang, J., Pd-Catalyzed C═C Double-Bond Formation by Coupling of N-Tosylhydrazones with Benzyl Halides. *Org. Lett.* 2009, 11 (20), 4732-4735.
9. Girase, T. R.; Kapdi, A. R., Novel Carbazole-Based N-Heterocyclic Carbene Ligands to Access Synthetically Relevant Stilbenes in Pd-Catalyzed Coupling Processes. *Chem. Asian J.* 2019, 14 (15), 2611-2619.
10. Prasanna, R.; Guha, S.; Sekar, G., Proton-Coupled Electron Transfer: Transition-Metal-Free Selective Reduction of Chalcones and Alkynes Using Xanthate/Formic Acid. *Org. Lett.* 2019, 21 (8), 2650-2653.

11. Zhou, Z.; Hou, Z.-L.; Yang, F.; Yao, B., Oxidative cross-coupling of allyl(trimethyl)silanes with aryl boronic acids by palladium catalysis. *Tetrahedron* 2018, 74 (50), 7228-7236.

12. Ainembabazi, D.; Reid, C.; Chen, A.; An, N.; Kostal, J.; Voutchkova-Kostal, A., Decarbonylative Olefination of Aldehydes to Alkenes. *Journal of the American Chemical Society* 2020, 142 (2), 696-699.

13. Kumar, B. S.; Anbarasan, R.; Amali, A. J.; Pitchumani, K., Isolable C@Fe3O4 nanospheres supported cubical Pd nanoparticles as reusable catalysts for Stille and Mizoroki-Heck coupling reactions. *Tetrahedron Lett.* 2017, 58 (33), 3276-3282.

14. Wang, Y.-P.; Lee, H. M., Catalytic application of zwitterionic palladium complexes in Mizoroki-Heck reactions using ionic liquid as solvent. *J. Organomet. Chem.* 2015, 791, 90-98.

15. Zhou, A.; Guo, R.-M.; Zhou, J.; Dou, Y.; Chen, Y.; Li, J.-R., Pd@ZIF-67 Derived Recyclable Pd-Based Catalysts with Hierarchical Pores for High-Performance Heck Reaction. *ACS Sustainable Chemistry & Engineering* 2018, 6 (2), 2103-2111.

16. Baggi, N.; Garoni, E.; Colombo, A.; Dragonetti, C.; Righetto, S.; Roberto, D.; Boixel, J.; Guerchais, V.; Fantacci, S., Design of cyclometallated 5-π-delocalized donor-1,3-di(2-pyridyl)benzene platinum(II) complexes with second-order nonlinear optical properties. *Polyhedron* 2018, 140, 74-77.

17. Moro, A. V.; Cardoso, F. S. P.; Correia, C. R. D., Heck arylation of styrenes with arenediazonium salts: short, efficient, and stereoselective synthesis of resveratrol, DMU-212, and analogues. *Tetrahedron Lett.* 2008, 49 (39), 5668-5671.

18. Carole, W. A.; Colacot, T. J., Understanding Palladium Acetate from a User Perspective. *Chem. Eur. J* 2016, 22 (23), 7686-95.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, the term "about" can include traditional rounding according to significant figures of the numerical value. In addition, the phrase "about 'x' to 'y'" includes "about 'x' to about 'y'".

It should be emphasized that the above-described embodiments of the present disclosure are merely possible examples of implementations, and are set forth only for a clear understanding of the principles of the disclosure. Many variations and modifications may be made to the above-described embodiments of the disclosure without departing substantially from the spirit and principles of the disclosure. All such modifications and variations are intended to be included herein within the scope of this disclosure.

The invention claimed is:

1. A method of making a substituted arene, comprising:

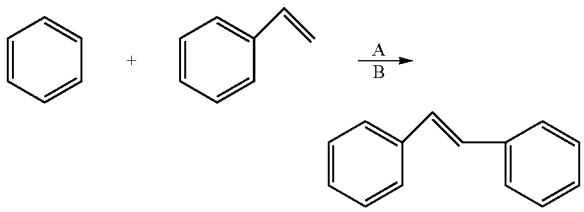

wherein A is a Rh catalyst or Rh pre-catalyst material, wherein the Rh catalyst selectively functionalizes CH bond on the arene compound, wherein B is an oxidant, wherein the Rh catalyst is a composition comprising:

a rhodium (I) catalyst having one of the following formula: $L_2Rh(L')X$, $L_3RhX$, $(L_1X_1)Rh(L')$, $[(L)_2Rh(\mu-X)]_2$, $RhX_3$, $[L_nRh_y(m-X)_m]$, or $(L)_nRh_m$ wherein $L_2$ is selected from:

two independent and neutral first ligands each coordinated to Rh(I) through a carbon donor, nitrogen donor, a phosphorus donor, an oxygen donor, or a sulfur donor, a neutral bidentate ligand coordinated to Rh(I) through either a carbon donor, nitrogen donor, a phosphorus donor, an oxygen donor, or a sulfur donor, or a combination of the neutral first ligand and the neutral bidentate ligand;

wherein L' is a neutral second ligand coordinated to Rh(I), wherein X is a mono-anionic group, either coordinated to the metal or not, wherein $L_3$ is a tridentate first ligand coordinated to Rh(I) in a $\kappa^2$ or $\kappa^3$ fashion through a carbon donor, a nitrogen donor, a phosphorus donor, an oxygen donor, a sulfur donor, or a combination thereof, wherein $L_1X_1$ is a monoanionic bidentate or tridentate second ligand coordinated to Rh(I) in a $\kappa^2$ or $\kappa^3$ fashion through a carbon donor, a nitrogen donor, a phosphorus donor, an oxygen donor, a sulfur donor, or a combination thereof, wherein L is a neutral, two-electron donating third ligand coordinated to Rh(I), and wherein y is 1 to 4, m is 1 to 4 and n is 3(m).

2. The method of claim 1, wherein the oxidant is selected from the group consisting of a copper(II) salt, iodates, periodates, nitrogen oxide, silver salt, peroxide, dioxygen, copper(I) salt and one or both of dioxygen and air, and a combination thereof.

3. The method of claim 1, wherein the Rh pre-catalyst material comprises Rh nanoparticles on a support or single atom Rh material on the support.

4. The method of claim 1, wherein the ratio of the benzene to styrene is about 1:100 to 1000:1, wherein the amount of Rh catalyst is about 20 mol % to 0.000000001 mol %, wherein the amount of oxidant is about 2 to 10,000 equivalents relative to Rh catalyst.

5. The method of claim 1, wherein the reaction temperature is about 125-205° C. for about 1 to 72 hours.

6. A method of making a substituted arene, comprising:

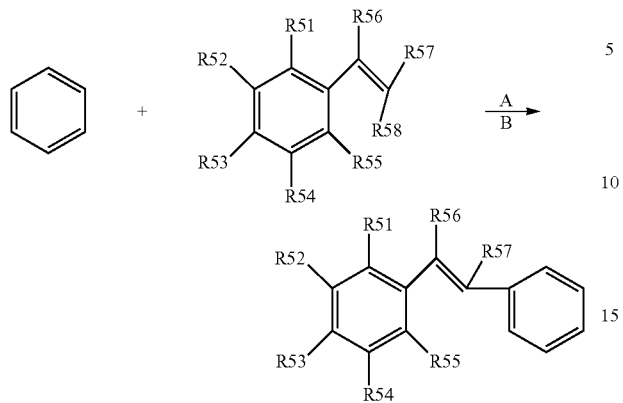

wherein A is a Rh catalyst or Rh pre-catalyst material, wherein the Rh catalyst selectively functionalizes CH bond on the benzene compound, wherein B is an oxidant, wherein R51 to R58 are each independently selected from the group consisting of: hydrogen, a halide, an alkyl, an alkenyl, a —O—R', a carbocycle group, a heterocyclo, an aryl, a heteroaryl, —NO$_2$, —C(O)OR', —CN, SiR'$_3$, and —OR', wherein each R' is independently selected from H and an alkyl, wherein the Rh catalyst is a composition comprising:
a rhodium (I) catalyst having one of the following formula: L$_2$Rh(L')X, L$_3$RhX, (L$_1$X$_1$)Rh(L'), [(L)$_2$Rh(μ-X)]$_2$, RhX$_3$, [L$_n$Rh$_y$(m-X)$_m$], or (L)$_n$Rh$_m$
wherein L$_2$ is selected from:
two independent and neutral first ligands each coordinated to Rh(I) through a carbon donor, nitrogen donor, a phosphorus donor, an oxygen donor, or a sulfur donor,
a neutral bidentate ligand coordinated to Rh(I) through either a carbon donor, nitrogen donor, a phosphorus donor, an oxygen donor, or a sulfur donor, or
a combination of the neutral first ligand and the neutral bidentate ligand;
wherein L' is a neutral second ligand coordinated to Rh(I),
wherein X is a mono-anionic group, either coordinated to the metal or not,
wherein L$_3$ is a tridentate first ligand coordinated to Rh(I) in a κ$^2$ or κ$^3$ fashion through a carbon donor, a nitrogen donor, a phosphorus donor, an oxygen donor, a sulfur donor, or a combination thereof,
wherein L$_1$X$_1$ is a monoanionic bidentate or tridentate second ligand coordinated to Rh(I) in a κ$^2$ or κ$^3$ fashion through a carbon donor, a nitrogen donor, a phosphorus donor, an oxygen donor, a sulfur donor, or a combination thereof,
wherein L is a neutral, two-electron donating third ligand coordinated to Rh(I), and
wherein y is 1 to 4, m is 1 to 4 and n is 3(m).

7. The method of claim 6, wherein the oxidant is selected from the group consisting of a copper(II) salt, iodates, periodates, nitrogen dioxide, silver salt, peroxide, dioxygen, copper(I) salt and one or both of dioxygen and air, and a combination thereof.

8. The method of claim 6, wherein the Rh pre-catalyst material comprises a Rh nanoparticles on a support or single atom Rh material on the support.

9. The method of claim 6, wherein the ratio of the benzene to styrene is about 1:100 to 1000:1, wherein the amount of Rh catalyst is about 20 mol % to 0.000000001 mol %, wherein the amount of oxidant is about 2 to 10,000 equivalents relative to Rh catalyst.

10. The method of claim 6, wherein the reaction temperature is about 125-205° C. for about 2 to 72 hours.

11. A method of making a substituted arene, comprising:

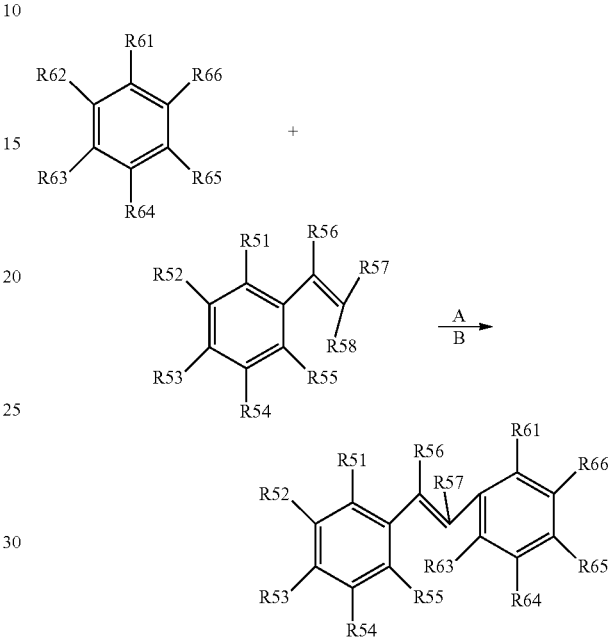

wherein A is a Rh catalyst or Rh pre-catalyst material, wherein the Rh catalyst selectively functionalizes a CH bond in meta and para positions of the substituted benezene relative to the functional group, wherein B is an oxidant,
wherein R51 to R58 are each independently selected from the group consisting of: hydrogen, a halide, an alkyl, an alkenyl, a —O—R', a carbocycle group, a heterocyclo, an aryl, a heteroaryl, —NO$_2$, —C(O)OR', —CN, SiR'$_3$, and —OR', wherein each R' is independently selected from H and an alkyl,
wherein R61 to R66 are each independently selected from the group consisting of: hydrogen, a halide, an alkyl, an alkenyl, a —O—R", a carbocycle group, a heterocyclo, an aryl, a heteroaryl, —NO$_2$, —C(O)OR", —CN, SiR"$_3$ and —OR", wherein each R" is independently selected from H and an alkyl,
wherein the Rh catalyst is a composition comprising:
a rhodium (I) catalyst having one of the following formula: L$_2$Rh(L')X, L$_3$RhX, (L$_1$X$_1$)Rh(L'), [(L)$_2$Rh(μ-X)]$_2$, RhX$_3$, [L$_n$Rh$_y$(m-X)$_m$], or (L)$_n$Rh$_m$
wherein L$_2$ is selected from:
two independent and neutral first ligands each coordinated to Rh(I) through a carbon donor, nitrogen donor, a phosphorus donor, an oxygen donor, or a sulfur donor,
a neutral bidentate ligand coordinated to Rh(I) through either a carbon donor, nitrogen donor, a phosphorus donor, an oxygen donor, or a sulfur donor, or
a combination of the neutral first ligand and the neutral bidentate ligand;

wherein L' is a neutral second ligand coordinated to Rh(I), wherein X is a mono-anionic group, either coordinated to the metal or not, wherein $L_3$ is a tridentate first ligand coordinated to Rh(I) in a $\kappa^2$ or $\kappa^3$ fashion through a carbon donor, a nitrogen donor, a phosphorus donor, an oxygen donor, a sulfur donor, or a combination thereof, wherein $L_1X_1$ is a monoanionic bidentate or tridentate second ligand coordinated to Rh(I) in a $\kappa^2$ or $\kappa^3$ fashion through a carbon donor, a nitrogen donor, a phosphorus donor, an oxygen donor, a sulfur donor, or a combination thereof, wherein L is a neutral, two-electron donating third ligand coordinated to Rh(I), and wherein y is 1 to 4, m is 1 to 4 and n is 3(m).

12. The method of claim 11, wherein the oxidant is selected from the group consisting of a copper(II) salt, iodates, periodates, nitrogen dioxide, silver salt, peroxide, dioxygen, copper(I) salt and one or both of dioxygen and air, and a combination thereof.

13. A method of making a substituted arene, comprising:

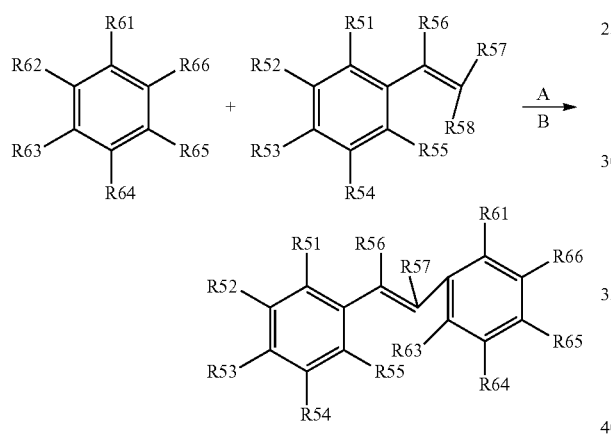

wherein A is a Rh catalyst or Rh pre-catalyst material, wherein the Rh catalyst selectively functionalizes a CH bond in meta and para positions of the substituted benzene relative to the functional group, wherein B is an oxidant, wherein R51 to R58 are each independently selected from the group consisting of: hydrogen, a halide, an alkyl, an alkenyl, a —O—R', a carbocycle group, a heterocyclo, an aryl, a heteroaryl, —NO$_2$, —C(O)OR', —CN, SiR'$_3$, and —OR', wherein each R' is independently selected from H and an alkyl, wherein R61 to R66 are each independently selected from the group consisting of: hydrogen, a halide, an alkyl, an alkenyl, a —O—R", a carbocycle group, a heterocyclo, an aryl, a heteroaryl, —NO$_2$, —C(O)OR", —CN, SiR"$_3$ and —OR", wherein each R" is independently selected from H and an alkyl, wherein the Rh catalyst is a composition comprising: a rhodium (I) catalyst having the following structure:

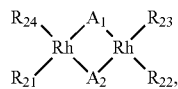

wherein $A_1$ and $A_2$ are independently selected from the group consisting of: a halogen, an acetate group, a sulfur-based ligand, a carbon-based ligand, hydroxyl, alkoxy, oxide, an amido, a phosphide, a phosphido, a nitride, a hydride, a phosphate (PF$_6$), and a borate (BPh$_4$), wherein $R_{21}$, $R_{22}$, $R_{23}$, and $R_{24}$ are independently selected from the group consisting of: an alkyl, an aryl, an acetate, a cyano group, an olefin, an imine, an ether, a nitrile, a ketone, water, a sulfur based ligand, a phosphine, a carbonyl, a phosphite, and a silicon based ligand.

14. A method of making a substituted arene, comprising:

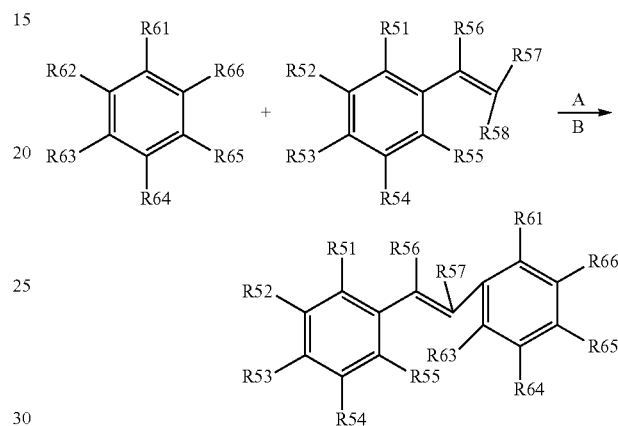

wherein A is a Rh catalyst or Rh pre-catalyst material, wherein the Rh catalyst selectively functionalizes a CH bond in meta and para positions of the substituted benzene relative to the functional group, wherein B is an oxidant, wherein R51 to R58 are each independently selected from the group consisting of: hydrogen, a halide, an alkyl, an alkenyl, a —O—R', a carbocycle group, a heterocyclo, an aryl, a heteroaryl, —NO$_2$, —C(O)OR', —CN, SiR'$_3$, and —OR', wherein each R' is independently selected from H and an alkyl, wherein R61 to R66 are each independently selected from the group consisting of: hydrogen, a halide, an alkyl, an alkenyl, a —O—R", a carbocycle group, a heterocyclo, an aryl, a heteroaryl, —NO$_2$, —C(O)OR", —CN, SiR"$_3$ and —OR", wherein each R" is independently selected from H and an alkyl, wherein the Rh catalyst is a composition comprising: a rhodium (I) catalyst having the following structure:

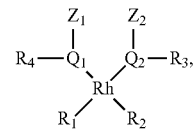

wherein $Q_1$ and $Q_2$ are independently selected from the group consisting of: N, O, P, S, Si, and C, wherein $Z_1$ and $Z_2$ are independently selected from the group consisting of: a halide, an alkyl, an alkenyl, a carbocycle group, a heterocyclo, an aryl, a heteroaryl, an acetate, a nitrile, a phosphite, a carbonyl, and a carboxylate, optionally, $Z_1$ and $Z_2$ are joined together with a bond to form a 5, 6, or 7-membered ring, wherein $R_1$ and $R_2$ are independently selected from the group consisting of: hydrogen, an alkyl, an aryl, an acetate, a cyano group, an olefin, an imine, an ether, a nitrile, a ketone, water, a sulfur based ligand, a phosphine, a carbonyl, a nitrosyl, a silane, and an N-Heterocyclic carbene, wherein $R_3$ and $R_4$ are independently selected from the group consisting of: a halide, an alkyl, an alkenyl, a carbocycle group, a heterocyclo, an aryl, a heteroaryl, an acetate, a cyano group, a nitrile, and a phosphite.

15. A method of making a substituted arene, comprising:

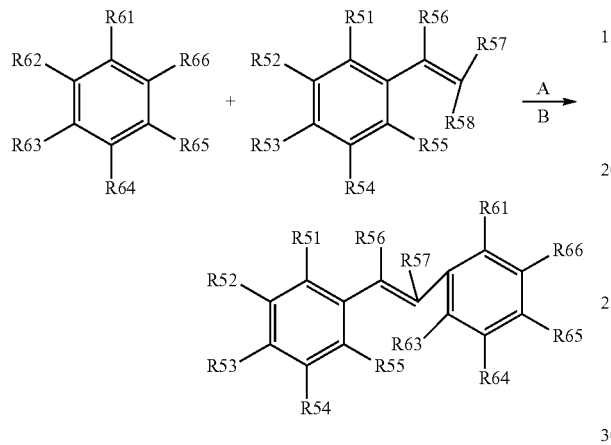

wherein A is a Rh catalyst or Rh pre-catalyst material, wherein the Rh catalyst selectively functionalizes a CH bond in meta and para positions of the substituted benezene relative to the functional group, wherein B is an oxidant, wherein R51 to R58 are each independently selected from the group consisting of: hydrogen, a halide, an alkyl, an alkenyl, a —O—R', a carbocycle group, a heterocyclo, an aryl, a heteroaryl, —$NO_2$, —C(O)OR', —CN, $SiR'_3$, and —OR', wherein each R' is independently selected from H and an alkyl, wherein R61 to R66 are each independently selected from the group consisting of: hydrogen, a halide, an alkyl, an alkenyl, a —O—R", a carbocycle group, a heterocyclo, an aryl, a heteroaryl, —$NO_2$, —C(O)OR", —CN, $SiR"_3$ and —OR", wherein each R" is independently selected from H and an alkyl, wherein the Rh catalyst is a composition comprising: a rhodium (I) catalyst having the following structure:

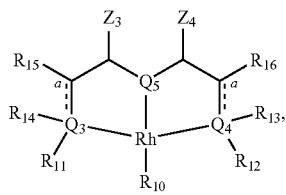

wherein $Q_3$, $Q_4$, and $Q_5$ are independently selected from the group consisting of: N, O, P, S, and Si, wherein $Z_3$ and $Z_4$ are independently selected from the group consisting of: a halide, an alkyl, an alkenyl, a carbocycle group, a heterocyclo, an aryl, a heteroaryl, an acetate, a cyano group, a carbonyl, and a silyl group, optionally, $Z_3$ and $Z_4$ are joined together with a bond to form a 5, 6, or 7-membered ring, wherein $R_{11}$ and $R_{12}$ are independently selected from the group consisting of: hydrogen, an alkyl, an aryl, an acetate, a cyano group, an olefin, an imine, an ether, a nitrile, a ketone, water, a sulfur based ligand, a phosphine, a silyl group, and an N-heterocyclic carbene, wherein $R_{10}$, $R_{13}$, $R_{14}$ $R_{15}$, and $R_{16}$ are independently selected from the group consisting of: a halide, an alkyl, an alkenyl, a carbocycle group, a heterocyclo, an aryl, a heteroaryl, an acetate, a cyano group, a nitrile, and a phosphite wherein, optionally, $R_{15}$ and $R_{14}$, $R_{14}$ and $R_{11}$, or $R_{11}$, $R_{14}$, and $R_{15}$ are joined together with a bond(s) to form a 5, 6, or 7-membered ring, wherein, optionally, $R_{16}$ and $R_{13}$, $R_{13}$ and $R_{12}$, or $R_{12}$, $R_{13}$, and $R_{16}$ are joined together with a bond(s) to form a 5, 6, or 7-membered ring.

16. A method of making a substituted arene, comprising:

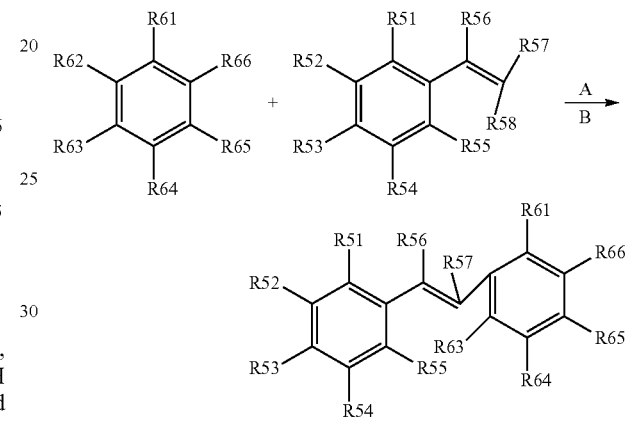

wherein A is a Rh catalyst or Rh pre-catalyst material, wherein the Rh catalyst selectively functionalizes a CH bond in meta and para positions of the substituted benezene relative to the functional group, wherein B is an oxidant, wherein R51 to R58 are each independently selected from the group consisting of: hydrogen, a halide, an alkyl, an alkenyl, a —O—R', a carbocycle group, a heterocyclo, an aryl, a heteroaryl, —$NO_2$, —C(O)OR', —CN, $SiR'_3$, and —OR', wherein each R' is independently selected from H and an alkyl, wherein R61 to R66 are each independently selected from the group consisting of: hydrogen, a halide, an alkyl, an alkenyl, a —O—R", a carbocycle group, a heterocyclo, an aryl, a heteroaryl, —$NO_2$, —C(O)OR", —CN, $SiR"_3$ and —OR", wherein each R" is independently selected from H and an alkyl, wherein the Rh pre-catalyst material comprises Rh nanoparticles on a support or single atom Rh material on the support.

17. A method of making a substituted arene, comprising:

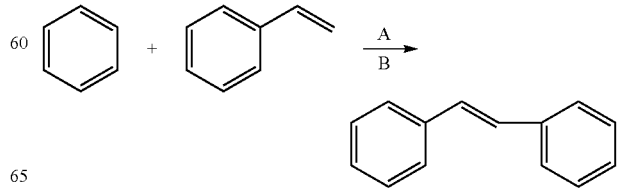

wherein A is a Rh catalyst or Rh pre-catalyst material, wherein the Rh catalyst selectively functionalizes CH bond on the arene compound, wherein B is an oxidant, wherein the Rh catalyst is a composition comprising: a rhodium (I) catalyst having the following structure:

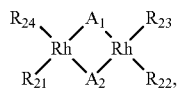

wherein $A_1$ and $A_2$ are independently selected from the group consisting of: a halogen, an acetate group, a sulfur-based ligand, a carbon-based ligand, hydroxyl, alkoxy, oxide, an amido, a phosphide, a phosphido, a nitride, a hydride, a phosphate ($PF_6$), and a borate ($BPh_4$), wherein $R_{21}$, $R_{22}$, $R_{23}$, and $R_{24}$ are independently selected from the group consisting of: an alkyl, an aryl, an acetate, a cyano group, an olefin, an imine, an ether, a nitrile, a ketone, water, a sulfur based ligand, a phosphine, a carbonyl, a phosphite, and a silicon based ligand.

18. A method of making a substituted arene, comprising:

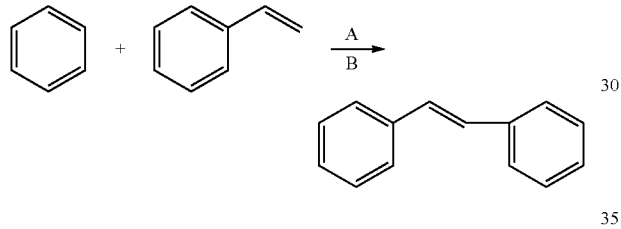

wherein A is a Rh catalyst or Rh pre-catalyst material, wherein the Rh catalyst selectively functionalizes CH bond on the arene compound, wherein B is an oxidant, wherein the Rh catalyst is a composition comprising: a rhodium (I) catalyst having the following structure:

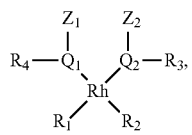

wherein $Q_1$ and $Q_2$ are independently selected from the group consisting of: N, O, P, S, Si, and C, wherein $Z_1$ and $Z_2$ are independently selected from the group consisting of: a halide, an alkyl, an alkenyl, a carbocycle group, a heterocyclo, an aryl, a heteroaryl, an acetate, a nitrile, a phosphite, a carbonyl, and a carboxylate, optionally, $Z_1$ and $Z_2$ are joined together with a bond to form a 5, 6, or 7-membered ring, wherein $R_1$ and $R_2$ are independently selected from the group consisting of: hydrogen, an alkyl, an aryl, an acetate, a cyano group, an olefin, an imine, an ether, a nitrile, a ketone, water, a sulfur based ligand, a phosphine, a carbonyl, a nitrosyl, a silane, and an N-Heterocyclic carbene, wherein $R_3$ and $R_4$ are independently selected from the group consisting of: a halide, an alkyl, an alkenyl, a carbocycle group, a heterocyclo, an aryl, a heteroaryl, an acetate, a cyano group, a nitrile, and a phosphite.

19. A method of making a substituted arene, comprising:

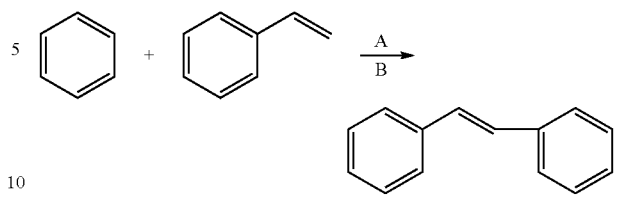

wherein A is a Rh catalyst or Rh pre-catalyst material, wherein the Rh catalyst selectively functionalizes CH bond on the arene compound, wherein B is an oxidant, wherein the Rh catalyst is a composition comprising: a rhodium (I) catalyst having the following structure:

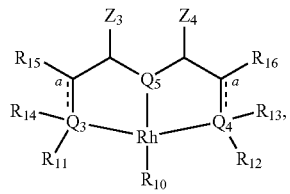

wherein $Q_3$, $Q_4$, and $Q_5$ are independently selected from the group consisting of: N, O, P, S, and Si, wherein $Z_3$ and $Z_4$ are independently selected from the group consisting of: a halide, an alkyl, an alkenyl, a carbocycle group, a heterocyclo, an aryl, a heteroaryl, an acetate, a cyano group, a carbonyl, and a silyl group, optionally, $Z_3$ and $Z_4$ are joined together with a bond to form a 5, 6, or 7-membered ring, wherein $R_{11}$ and $R_{12}$ are independently selected from the group consisting of: hydrogen, an alkyl, an aryl, an acetate, a cyano group, an olefin, an imine, an ether, a nitrile, a ketone, water, a sulfur based ligand, a phosphine, a silyl group, and an N-heterocyclic carbene, wherein $R_{10}$, $R_{13}$, $R_{14}$ $R_{15}$, and $R_{16}$ are independently selected from the group consisting of: a halide, an alkyl, an alkenyl, a carbocycle group, a heterocyclo, an aryl, a heteroaryl, an acetate, a cyano group, a nitrile, and a phosphite wherein, optionally, $R_{15}$ and $R_{14}$, $R_{14}$ and $R_{11}$, or $R_{11}$, $R_{14}$, and $R_{15}$ are joined together with a bond(s) to form a 5, 6, or 7-membered ring, wherein, optionally, $R_{16}$ and $R_{13}$, $R_{13}$ and $R_{12}$, or $R_{12}$, $R_{13}$, and $R_{16}$ are joined together with a bond(s) to form a 5, 6, or 7-membered ring.

20. A method of making a substituted arene, comprising:

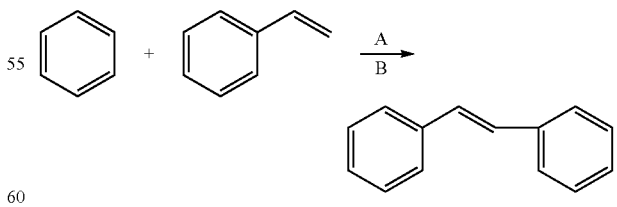

wherein A is a Rh catalyst or Rh pre-catalyst material, wherein the Rh catalyst selectively functionalizes CH bond on the arene compound, wherein B is an oxidant, wherein the Rh pre-catalyst material comprises Rh nanoparticles on a support or single atom Rh material on the support.

21. A method of making a substituted arene, comprising:

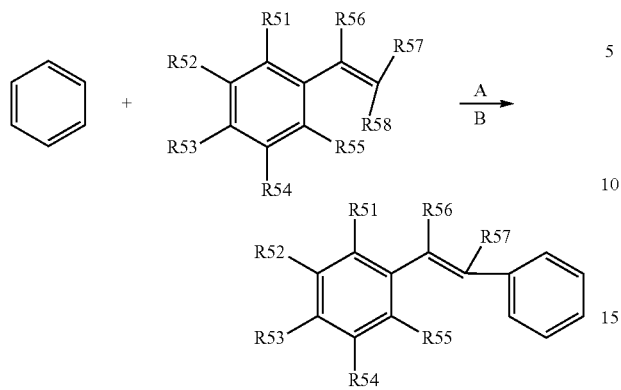

wherein A is a Rh catalyst or Rh pre-catalyst material, wherein the Rh catalyst selectively functionalizes CH bond on the benzene compound, wherein B is an oxidant, wherein R51 to R58 are each independently selected from the group consisting of: hydrogen, a halide, an alkyl, an alkenyl, a —O—R', a carbocycle group, a heterocyclo, an aryl, a heteroaryl, —$NO_2$, —C(O)OR', —CN, $SiR'_3$, and —OR', wherein each R' is independently selected from H and an alkyl, wherein the Rh catalyst is a composition comprising: a rhodium (I) catalyst having the following structure:

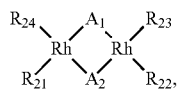

wherein $A_1$ and $A_2$ are independently selected from the group consisting of: a halogen, an acetate group, a sulfur-based ligand, a carbon-based ligand, hydroxyl, alkoxy, oxide, an amido, a phosphide, a phosphido, a nitride, a hydride, a phosphate ($PF_6$), and a borate ($BPh_4$), wherein $R_{21}$, $R_{22}$, $R_{23}$, and $R_{24}$ are independently selected from the group consisting of: an alkyl, an aryl, an acetate, a cyano group, an olefin, an imine, an ether, a nitrile, a ketone, water, a sulfur based ligand, a phosphine, a carbonyl, a phosphite, and a silicon based ligand.

22. A method of making a substituted arene, comprising:

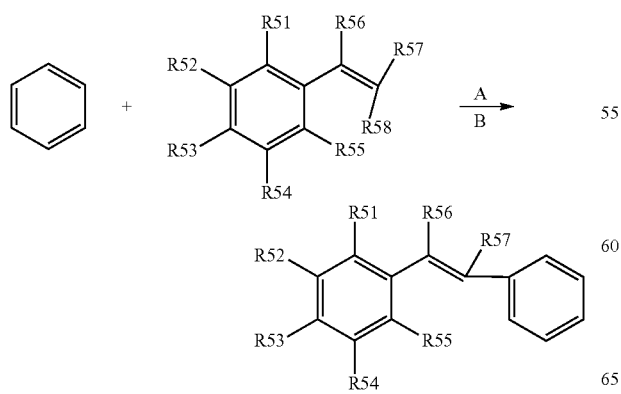

wherein A is a Rh catalyst or Rh pre-catalyst material, wherein the Rh catalyst selectively functionalizes CH bond on the benzene compound, wherein B is an oxidant, wherein R51 to R58 are each independently selected from the group consisting of: hydrogen, a halide, an alkyl, an alkenyl, a —O—R', a carbocycle group, a heterocyclo, an aryl, a heteroaryl, —$NO_2$, —C(O)OR', —CN, $SiR'_3$, and —OR', wherein each R' is independently selected from H and an alkyl, wherein the Rh catalyst is a composition comprising: a rhodium (I) catalyst having the following structure:

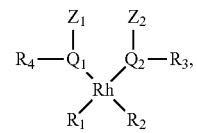

wherein $Q_1$ and $Q_2$ are independently selected from the group consisting of: N, O, P, S, Si, and C, wherein $Z_1$ and $Z_2$ are independently selected from the group consisting of: a halide, an alkyl, an alkenyl, a carbocycle group, a heterocyclo, an aryl, a heteroaryl, an acetate, a nitrile, a phosphite, a carbonyl, and a carboxylate, optionally, $Z_1$ and $Z_2$ are joined together with a bond to form a 5, 6, or 7-membered ring, wherein $R_1$ and $R_2$ are independently selected from the group consisting of: hydrogen, an alkyl, an aryl, an acetate, a cyano group, an olefin, an imine, an ether, a nitrile, a ketone, water, a sulfur based ligand, a phosphine, a carbonyl, a nitrosyl, a silane, and an N-Heterocyclic carbene, wherein $R_3$ and $R_4$ are independently selected from the group consisting of: a halide, an alkyl, an alkenyl, a carbocycle group, a heterocyclo, an aryl, a heteroaryl, an acetate, a cyano group, a nitrile, and a phosphite.

23. A method of making a substituted arene, comprising:

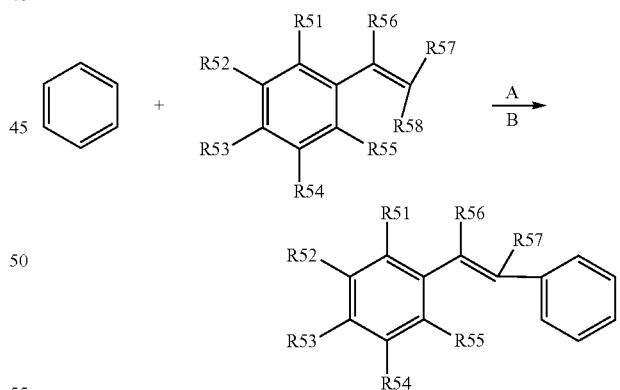

wherein A is a Rh catalyst or Rh pre-catalyst material, wherein the Rh catalyst selectively functionalizes CH bond on the benzene compound, wherein B is an oxidant, wherein R51 to R58 are each independently selected from the group consisting of: hydrogen, a halide, an alkyl, an alkenyl, a —O—R', a carbocycle group, a heterocyclo, an aryl, a heteroaryl, —$NO_2$, —C(O)OR', —CN, $SiR'_3$, and —OR', wherein each R' is independently selected from H and an alkyl, wherein the Rh catalyst is a composition comprising: a rhodium (I) catalyst having the following structure:

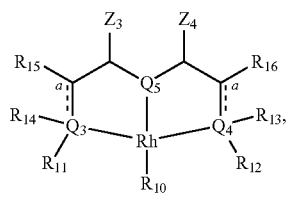

wherein $Q_3$, $Q_4$, and $Q_5$ are independently selected from the group consisting of: N, O, P, S, and Si, wherein $Z_3$ and $Z_4$ are independently selected from the group consisting of: a halide, an alkyl, an alkenyl, a carbocycle group, a heterocyclo, an aryl, a heteroaryl, an acetate, a cyano group, a carbonyl, and a silyl group, optionally, $Z_3$ and $Z_4$ are joined together with a bond to form a 5, 6, or 7-membered ring, wherein $R_{11}$ and $R_{12}$ are independently selected from the group consisting of: hydrogen, an alkyl, an aryl, an acetate, a cyano group, an olefin, an imine, an ether, a nitrile, a ketone, water, a sulfur based ligand, a phosphine, a silyl group, and an N-heterocyclic carbene, wherein $R_{10}$, $R_{13}$, $R_{14}$, $R_{15}$, and $R_{16}$ are independently selected from the group consisting of: a halide, an alkyl, an alkenyl, a carbocycle group, a heterocyclo, an aryl, a heteroaryl, an acetate, a cyano group, a nitrile, and a phosphite wherein, optionally, $R_{15}$ and $R_{14}$, $R_{14}$ and $R_{11}$, or $R_{11}$, $R_{14}$, and $R_{15}$ are joined together with a bond(s) to form a 5, 6, or 7-membered ring, wherein, optionally, $R_{16}$ and $R_{13}$, $R_{13}$ and $R_{12}$, or $R_{12}$, $R_{13}$, and $R_{16}$ are joined together with a bond(s) to form a 5, 6, or 7-membered ring.

24. A method of making a substituted arene, comprising:

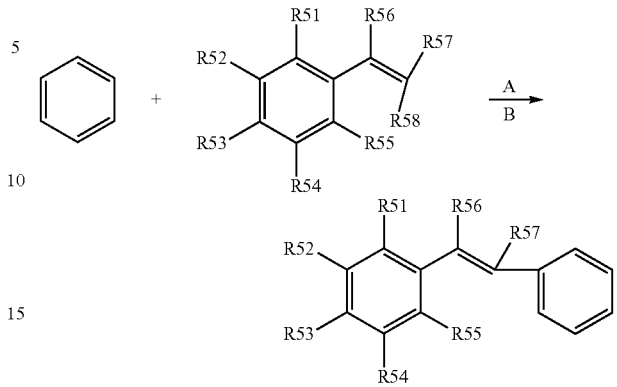

wherein A is a Rh catalyst or Rh pre-catalyst material, wherein the Rh catalyst selectively functionalizes CH bond on the benzene compound, wherein B is an oxidant, wherein R51 to R58 are each independently selected from the group consisting of: hydrogen, a halide, an alkyl, an alkenyl, a —O—R', a carbocycle group, a heterocyclo, an aryl, a heteroaryl, —NO$_2$, —C(O)OR', —CN, SiR'$_3$, and —OR', wherein each R' is independently selected from H and an alkyl, wherein the Rh pre-catalyst material comprises a Rh nanoparticles on a support or single atom Rh material on the support.

* * * * *